(12) United States Patent
D'Amour et al.

(10) Patent No.: US 11,623,023 B2
(45) Date of Patent: Apr. 11, 2023

(54) PDX1 PANCREATIC ENDODERM CELLS IN CELL DELIVERY DEVICES AND METHODS THEREOF

(71) Applicant: Viacyte, Inc., San Diego, CA (US)

(72) Inventors: Kevin Allen D'Amour, San Diego, CA (US); Evert Kroon, San Diego, CA (US); Michael Scott, San Diego, CA (US); Laura Martinson, San Diego, CA (US); Craig McGreevy, San Diego, CA (US)

(73) Assignee: ViaCyte, Inc., San Diego, CA (US)

( * ) Notice: Subject to any disclaimer, the term of this patent is extended or adjusted under 35 U.S.C. 154(b) by 358 days.

(21) Appl. No.: 16/347,790

(22) PCT Filed: Nov. 10, 2016

(86) PCT No.: PCT/US2016/061442
§ 371 (c)(1),
(2) Date: May 6, 2019

(87) PCT Pub. No.: WO2018/089011
PCT Pub. Date: May 17, 2018

(65) Prior Publication Data
US 2019/0328934 A1    Oct. 31, 2019

(51) Int. Cl.
*A61L 27/38* (2006.01)
*A61L 27/56* (2006.01)

(52) U.S. Cl.
CPC ........... *A61L 27/3804* (2013.01); *A61L 27/56* (2013.01)

(58) Field of Classification Search
CPC ..... A61K 9/0024; A61K 9/70; A61L 27/3804; A61L 27/56; A61F 2/022; C12N 5/0677; C12N 2535/00
See application file for complete search history.

(56) References Cited

U.S. PATENT DOCUMENTS

| | | |
|---|---|---|
| 3,616,930 A | 11/1971 | Muir |
| 4,298,002 A | 11/1981 | Ronel et al. |
| 4,723,953 A | 2/1988 | Rosenbaum et al. |
| 4,968,733 A | 11/1990 | Muller et al. |

(Continued)

FOREIGN PATENT DOCUMENTS

| | | |
|---|---|---|
| NO | 328180 B1 | 12/2009 |
| WO | 1991002498 A1 | 3/1991 |

(Continued)

OTHER PUBLICATIONS

European Search Report dated May 7, 2020, for Application No. 16921167.9-1122/3537986; Applicant is ViaCyte, Inc.

(Continued)

*Primary Examiner* — Sean C. Barron
(74) *Attorney, Agent, or Firm* — Klarquist Sparkman, LLP

(57) ABSTRACT

Disclosed are devices and methods for transplanting cells, such as pancreatic endoderm cells, into a host. The devices include a non-woven fabric external to a cell-excluding membrane, and the non-woven fabric and/or cell-excluding membrane can be perforated. Treatment of the host with immunosuppressive reagents, required to inhibit allograft rejection due to perforations in the cell delivery device, does not compromise maturation or function of transplanted pancreatic endoderm cells.

18 Claims, 19 Drawing Sheets

(56) References Cited

U.S. PATENT DOCUMENTS

| | | |
|---|---|---|
| 4,976,859 A | 12/1990 | Wechs |
| 5,002,661 A | 3/1991 | Chick et al. |
| 5,011,494 A | 4/1991 | Recum et al. |
| 5,026,365 A | 6/1991 | Rossini et al. |
| 5,100,392 A | 3/1992 | Orth et al. |
| 5,116,493 A | 5/1992 | Chick et al. |
| 5,158,881 A | 10/1992 | Aebischer et al. |
| 5,219,361 A | 6/1993 | Recum et al. |
| 5,284,761 A | 2/1994 | Aebischer et al. |
| 5,314,471 A | 5/1994 | Brauker et al. |
| 5,324,518 A | 6/1994 | Orth et al. |
| 5,344,454 A | 9/1994 | Clarke et al. |
| 5,453,278 A | 9/1995 | Chan et al. |
| 5,453,357 A | 9/1995 | Hogan |
| 5,500,167 A | 3/1996 | Degen |
| 5,545,223 A | 8/1996 | Neuenfeldt et al. |
| 5,549,675 A | 8/1996 | Neuenfeldt et al. |
| 5,554,148 A | 9/1996 | Aebischer et al. |
| 5,569,462 A | 10/1996 | Martinson et al. |
| 5,593,440 A | 1/1997 | Brauker et al. |
| 5,626,561 A * | 5/1997 | Butler ............... A61F 2/022 604/500 |
| 5,653,756 A | 8/1997 | Clarke et al. |
| 5,670,372 A | 9/1997 | Hogan |
| 5,690,926 A | 11/1997 | Hogan |
| 5,713,888 A | 2/1998 | Neuenfeldt et al. |
| 5,733,336 A | 3/1998 | Neuenfeldt et al. |
| 5,738,673 A | 4/1998 | Mills et al. |
| 5,741,330 A | 4/1998 | Brauker et al. |
| 5,782,912 A | 7/1998 | Brauker et al. |
| 5,787,900 A | 8/1998 | Butler et al. |
| 5,800,529 A | 9/1998 | Brauker et al. |
| 5,807,406 A | 9/1998 | Brauker et al. |
| 5,843,780 A | 12/1998 | Thomson |
| 5,882,354 A | 3/1999 | Brauker et al. |
| 5,902,745 A | 5/1999 | Butler et al. |
| 5,913,998 A | 6/1999 | Butler et al. |
| 5,964,261 A | 10/1999 | Neuenfeldt et al. |
| 5,964,804 A | 10/1999 | Brauker et al. |
| 5,980,889 A | 11/1999 | Butler et al. |
| 6,060,640 A | 5/2000 | Pauley et al. |
| 6,156,305 A | 12/2000 | Brauker et al. |
| 6,365,385 B1 | 4/2002 | Opara |
| 6,702,857 B2 | 3/2004 | Brauker et al. |
| 6,773,458 B1 | 8/2004 | Brauker et al. |
| 7,192,450 B2 | 3/2007 | Brauker et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 7,625,753 B2 | 12/2009 | Kelly et al. |
| 7,695,963 B2 | 4/2010 | Agulnick et al. |
| 7,695,965 B2 | 4/2010 | Martinson et al. |
| 7,704,738 B2 | 4/2010 | D'Amour et al. |
| 7,993,916 B2 | 8/2011 | Agulnick et al. |
| 7,993,920 B2 | 8/2011 | Martinson et al. |
| 8,008,075 B2 | 8/2011 | Green et al. |
| 8,118,877 B2 | 2/2012 | Brauker et al. |
| 8,129,182 B2 | 3/2012 | D'Amour et al. |
| 8,211,699 B2 | 7/2012 | Robins et al. |
| 8,216,836 B2 | 7/2012 | D'Amour et al. |
| 8,278,106 B2 | 10/2012 | Martinson et al. |
| 8,334,138 B2 | 12/2012 | Robins et al. |
| 8,338,170 B2 | 12/2012 | Kelly et al. |
| 8,425,928 B2 | 4/2013 | Martinson et al. |
| 8,623,645 B2 | 1/2014 | D'Amour et al. |
| 8,859,286 B2 | 10/2014 | Agulnick |
| 8,895,300 B2 | 11/2014 | Schulz |
| D726,306 S | 4/2015 | Green |
| D726,307 S | 4/2015 | Green |
| D728,095 S | 4/2015 | Green |
| D734,847 S | 7/2015 | Green |
| 9,109,245 B2 | 8/2015 | Agulnick et al. |
| 9,526,880 B2 | 12/2016 | So et al. |
| 2007/0134305 A1* | 6/2007 | Zilberman ............. A61K 38/44 424/443 |
| 2010/0124564 A1 | 5/2010 | Martinson et al. |
| 2010/0196439 A1 | 8/2010 | Beck et al. |
| 2012/0245705 A1 | 9/2012 | Hasilo et al. |
| 2013/0139691 A1 | 6/2013 | Goldbach et al. |
| 2013/0261568 A1 | 10/2013 | Martinson et al. |
| 2014/0014226 A1* | 1/2014 | Green ............... A61F 2/022 141/18 |
| 2014/0257515 A1 | 9/2014 | So et al. |
| 2018/0125632 A1 | 5/2018 | Gore et al. |

FOREIGN PATENT DOCUMENTS

| | | |
|---|---|---|
| WO | 1991010425 A1 | 7/1991 |
| WO | 1992019195 A1 | 11/1992 |
| WO | 1993000439 A1 | 1/1993 |
| WO | 1993021902 A1 | 11/1993 |
| WO | 1995005452 A2 | 2/1995 |
| WO | 1995018584 A1 | 7/1995 |
| WO | 1996010966 A1 | 4/1996 |
| WO | 1996032076 A1 | 10/1996 |
| WO | 1996039100 A1 | 12/1996 |
| WO | 1999053021 A9 | 5/2000 |
| WO | 2000043052 A1 | 7/2000 |
| WO | 2003059072 A1 | 7/2003 |
| WO | 2003011354 A3 | 8/2003 |
| WO | 2008112190 A1 | 9/2008 |
| WO | 2010057039 A2 | 5/2010 |
| WO | 2012115619 A1 | 8/2012 |
| WO | 2014138671 A2 | 9/2014 |
| WO | 2014173441 A1 | 10/2014 |
| WO | 2015160348 A1 | 10/2015 |

OTHER PUBLICATIONS

Brauker et al., "Local inflammatory response around diffusion chambers containing xenografts. Nonspecific destruction of tissues and decreased local vascularization", Transplantation 61(12):1671-1677; 1996.

Brauker et al., "Neovascularization of synthetic membranes directed by membrane microarchitecture", Journal of Biomedical Materials Research, 29:1517-1524; 1995.

Brauker, James H et al., Neovascularization of synthetic membranes directed by membrane microarchitecture, Baxter Healthcare Corp., Baxter Technology Park, Round Lake, Illinois 60073; Journal of Biomedical Materials Research, vol. 29, 1517-1524 1995.

D'Amour et al., "Efficient differentiation of human embryonic stem cells to definitive endoderm" Nature Biotechnology. 23:1534-41, 2005.

Docherty et al., "Embryonic stem cell therapy for diabetes mellitus", Semin Cell Dev Biol. (2007) 18(6):827-38.

Extended European Search Report dated Jul. 23, 2013 from European Patent Application No. EP 09826863.4, 7 pages.

Gardner, "Stem cells and regenerative medicine: principles, prospects and problems," C.R. Biol. (2007) 330(6-7):465-73.

Guo, et al., "Stem Cells to Pancreatic .beta.-Cells: New Sources for Diabetes Cell Therapy," (2009), Endocrine Review, 30:214-227.

International Preliminary Examination Report from International Patent Application No. PCT/US02/16830, dated Sep. 21, 2004.

International Preliminary Report on Patentability from International Patent Application No. PCT/US2005/022604, dated Jan. 9, 2007.

International Preliminary Report on Patentability from International Patent Application No. PCT/US2005/024161, dated Jan. 9, 2007.

International Preliminary Report on Patentability dated Sep. 17, 2015, issued in connection with corresponding International Application No. PCT/US14/022109 (6 pages total).

International Search Report and Written Opinion dated Jun. 26, 2014 for International Application No. PCT/US2014/022109, 9 pages.

International Search Report and Written Opinion from International Application No. PCT/US2007/080589, dated Jun. 17, 2008.

International Search Report and Written Opinion from International Application No. PCT/US2009/064459, dated Oct. 4, 2010.

International Search Report and Written Opinion from International Patent Application No. PCT/US/2006/042413, dated Apr. 16, 2007.

(56) References Cited

OTHER PUBLICATIONS

International Search Report and Written Opinion from International Patent Application No. PCT/US2005/014239, dated Aug. 31, 2006.
International Search Report and Written Opinion from International Patent Application No. PCT/US2005/047175, dated Jul. 5, 2006.
International Search Report and Written Opinion issued in PCT/US2007/155336, dated Jan. 3, 2008.
International Search Report from International Patent Application No. PCT/US2004/043696, dated Aug. 11, 2005.
Korsgren et al., "Current Status of Clinical Islet Transplantation", Transplantation 79(10):1289-1293; 2005.
Kumagai-Braesch et al., "The TheraCyte.sup.IM Device Protects against Islet Allograft Rejection in Immunized Hosts", Cell Transplantation, 22:1137-1146; 2013.
Loudovaris et al., "CD4+ T cell mediated destruction of xenografts within cell-impermeable membranes in the absence of CD8+ T cells and B cells", Transplantation 61:1678-1684; 1996.
Loudovaris et al., "Destruction of Xenografts But Not Allografts Within Cell Impermeable Membranes", Transplantation Proceedings 24:2291-2292; 1992.
Madsen, "Stem Cells and Diabetes Treatment," APIMIS (2005) 113(11-12):858-875.
Madsen, "Towards cell therapy for diabetes," Nature Biotechnology, (2006) 24(12):1481-83.
Soon-Shiong, P., "Treatment of Type I Diabetes using Encapsulated Islets" Advanced Drug Delivery Reviews (1999) 35: 259-270.
Supplementary Partial European Search Report from EP 02739480, dated Feb. 1, 2005.

\* cited by examiner

PDX1 PANCREATIC ENDODERM CELLS IN CELL DELIVERY DEVICES AND METHODS THEREOF

CROSS REFERENCE TO RELATED APPLICATION

This is the U.S. National Stage of International Application No. PCT/US2016/061442, filed Nov. 10, 2016. The prior application is incorporated herein in its entirety.

FIELD

This relates to the field of devices for the delivery of cells, such as pancreatic endoderm cells, and their use.

STATEMENT OF SUPPORT

This invention was funded in part by the California Institute of Regenerative Medicine.

BACKGROUND

Several approaches have been attempted for implanting living cells or tissue in devices. For example, perforated cell delivery devices have been previously reported. See U.S. application Ser. No. 12/618,659 and WO 1993002635 which are herein incorporated by reference in their entirety. In these disclosures each layer of the cell delivery device is perforated, i.e., perforations traverse each wall of the device or the entire device (all layers). When each layer of the device is perforated, cells may escape from the device.

Valentini et al., U.S. Pat. No. 4,877,029, which is herein incorporated by reference in its entirety, describes a semipermeable nerve guidance channel or tube which is composed of a cell impermeable smooth inner membrane face and an outer surface with pores that form a trabeculae configuration, which pores are in the size range of 1 to 20 microns. This trabeculae configuration does not include holes (pores) which traverse the thickness of the tube and thus the configuration does not allow vascular growth into the inner compartment.

Non-woven fabrics have been used inside cell delivery devices. The non-woven fabrics provide an inert scaffold within the delivery device that provides a structure for adhering and distributing the cells within the device. See U.S. Pat. No. 5,853,717 (incorporated by reference in its entirety).

Non-woven fabrics have also been used to surround glucose monitoring devices. U.S. Pat. No. 8,527,026, which is herein incorporated by reference in its entirety, describes a sensor surrounded by an angiogenic layer of expanded polytetrafluoroethylene (ePTFE) and an NWF can be laminated over the ePTFE. In the '026 patent, the patient's blood glucose levels are being measured by the sensor.

Although many strategies have been developed to encapsulate cells and promote their survival in vivo only mixed results have been reported. Thus, there remains a need for a device and methods for transplanting cells that promote maturation or function of the transplanted cells.

SUMMARY OF THE INVENTION

Medical devices for delivering cells, and methods to promote cell survival, differentiation, and maturation of implanted cells are provided. Specifically, embodiments described herein improve the interface between the host's tissue and the delivery device by providing a non-woven fabric (NWF), for example, non-woven polyester fabric (NWPF), external to the cell excluding membrane to improve graft vascularization. Embodiments described herein include perforations in just the NWF and cell-excluding membrane to improve graft vascularization. Embodiments described herein regulate the host immune response which improves cell survival.

In some embodiments, disclosed is a combination product that includes (a) a cell delivery device comprising a non-woven fabric layer and (B) PDX1-positive pancreatic endoderm cells.

In other embodiments, methods are disclosed for producing insulin in a mammal. The method includes a) administering to a mammalian host an immunosuppressive drug; b) implanting a perforated device comprising pancreatic endoderm cells into the mammalian host; and c) maturing the pancreatic endoderm cell population in the perforated device in the mammalian host such that the progenitor cell population produces insulin secreting cells.

BRIEF DESCRIPTION OF THE DRAWINGS

FIG. 10A shows a complete lack of endogenous rat beta cell function in animals receiving cyclosporine A at 12 weeks. FIG. 10B shows that the CsA treated rats have slightly elevated human c-peptide levels due to the CsA toxicity of endogenous beta cells.

DETAILED DESCRIPTION

Figure 1A:
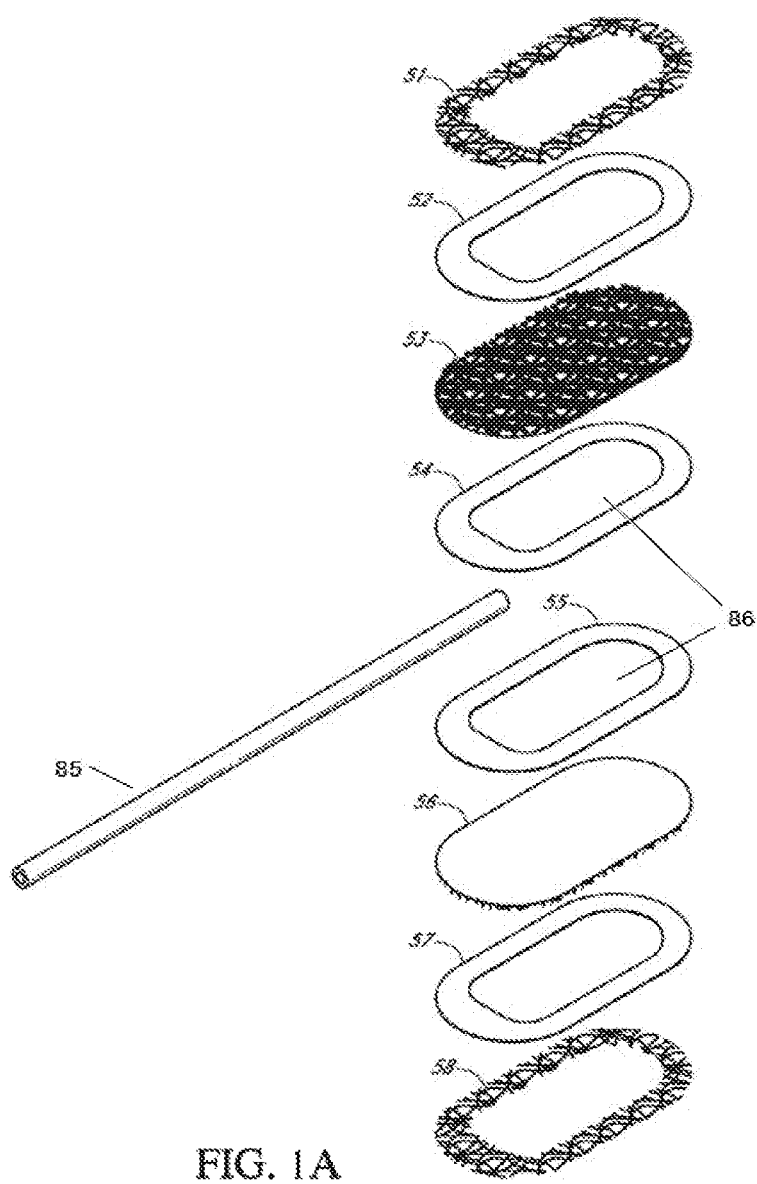
FIGS. 1A-1D illustrate a delivery device consistent with the present disclosure.

Reference will now be made in detail to embodiments of this disclosure, examples of which are illustrated in the accompanying drawings. Wherever possible, the same reference numbers will be used throughout the drawings to refer to the same or like parts.

Explanation of Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Therapeutic Agent: In some embodiments, the cell delivery device includes a therapeutic agent. The term "therapeutic agent" refers to any agent which provides a therapeutic or prophylactic result against a given disease or disease-causing agent such as a microbe. Preferably, the therapeutic agent is encapsulated cells, cell aggregates, organoids, clusters, clumps, tissues or a toxin directed against cancer cells such as doxorubicin, daunomycin, epirubicin, vinblastine, vincristine, mitoxantrone, bleomycin, mitomycin, mechlorethamine and the like. The therapeutic agent may be an antibody or fragment thereof, a DNA molecule or an RNA molecule. Additionally, the therapeutic agent may further comprise an anti-viral agent, an antibacterial agent, an antifungal agent, or any other agent which further facilitates the treatment or prophylaxis of the cellular disease or disorder. In some embodiments, the therapeutic agent is a cell to be implanted as defined below.

Implanted Cells: In one embodiment, the transplant site or delivery device is loaded with "cells" also referred to as "implanted cells" or "exogenous cells" or "a cell suitable for transplant" or "transplanted cells" or "implanted cells" or "therapeutic cells" or "implanted encapsulated cells" or "encapsulated cells" or "therapeutic allogeneic cells" or "therapeutic autologous cells." A wide variety of cells may be used in the disclosed methods. The implanted cells can be homogenous or heterogeneous cell populations, or cells producing one or more biologically active substances of interest. Implanted cells may not initially be therapeutically active when first implanted, e.g. pancreatic progenitors or PDX1-positive pancreatic endoderm, but once transplanted they further develop and mature and have a therapeutic effect. As used herein, a "cell to be implanted" refers to a cell or a population of cells sufficiently viable and/or functional or will become functional for in vivo treatment of a metabolic disorder "Induced pluripotent stem cells," or "iPS cells" or "iPSCs", refer to a type of pluripotent stem cell artificially prepared from a non-pluripotent cell, typically an adult somatic cell, or terminally differentiated cell, such as a fibroblast, a hematopoietic cell, a myocyte, a neuron, an epidermal cell, or the like, by inserting certain genes or gene products, referred to as reprogramming factors. See Takahashi et al., Cell 131:861-872 (2007); Wernig et al., Nature 448:318-324 (2007); Park et al., *Nature* 451:141-146 (2008) see also PCT Publication No. WO 2010048567, PCT Application No. PCT/US2009/061935, PCT Application No. PCT/JP2009/063906 and U. S. Published Patent Application Nos. 2011/0039338US, 2011/0039338, which are all herein incorporated by reference in their entirety. These and other known methods for making iPSC are well known, and the manner in which iPSC are derived or produced is not limiting to the disclosed methods. Human iPSC provide a source of pluripotent stem cells without the associated use of embryos.

Implanted cells include reprogrammed cells. As used herein, the term "reprogramming", "reprogrammed" or equivalents thereof, refers to a process that confers on a cell a measurably increased capacity to form progeny of at least one new cell type, either in culture or in vivo, then it would have under the same conditions without reprogramming.

Implanted cells include differentiated, dedifferentiated and transdifferentiated cells. Hence, as used herein, the phrase "differentiation" refers to the process by which a less specialized cell becomes a more specialized cell type. In contrast, the phrase "dedifferentiation" refers to a cellular process in which a partially or terminally differentiated cell reverts to an earlier developmental stage, such as a cell having pluripotency or multipotency. In further contrast, the phrase "transdifferentiation" refers to a process of transforming one differentiated cell type into another differentiated cell type.

Implanted cells include singly hormonal or polyhormonal cells. As used herein, "singly hormonal" cells or equivalents thereof, refers to cells that express only one hormone (e.g. immature beta cells and beta cells express only insulin protein, and not glucagon or somatostatin protein). As used herein "polyhormonal" cells express more than one or multiple hormones (e.g. endocrine precursors or progenitor cells have subpopulations of cells that express 2, 3 or 4 or more hormones on the same cell).

Implanted cells include mesendoderm cells. The term "mesendoderm cell" or equivalents thereof, refers to a multipotent cell having relative high expression levels of brachyury, FGF4, SNAH MIXL1 and/or WNT3 marker genes, as compared to SOX17 low, CXCR4 low, FOXA2 low, SOX7 low and SOX1 low.

Implanted cells include definitive endoderm cells. The term "definitive endoderm" or "DE" or "definitive endoderm lineage" or equivalents thereof, refers to a multipotent endoderm lineage cell that can differentiate into cells of the gut tube or organs derived from the gut tube.

Implanted cells include PDX1-negative foregut endoderm cells. The term "PDX1-negative foregut endoderm cells" or "foregut endoderm cells" or equivalents thereof, are cells that express SOX17, HNF1β (HNF1B), HNF4alpha (HNF4A) and FOXA1 markers but do not substantially express PDX1, AFP, SOX7, or SOX1. PDX1-negative foregut endoderm cell populations and methods of production thereof are described in U.S. application Ser. No. 11/588,693, entitled PDX1-expressing dorsal and ventral foregut endoderm, filed Oct. 27, 2006, which is incorporated by reference in its entirety.

Implanted cells include PDX1-positive, dorsally-biased, foregut endoderm cells. The term "PDX1-positive, dorsally-biased, foregut endoderm cells" (dorsal PDX1-positive foregut endoderm cells) are cells that express one or more markers selected from Table 1 of U.S. application Ser. No. 13/761,078, filed Feb. 6, 2013, no U.S. Pat. No. 9,109,245 which is incorporated by reference in its entirety.

Implanted cells include pancreatic endoderm cells. The term, "pancreatic endoderm," "pancreatic epithelial," "pancreatic epithelium" (all can be abbreviated "PE"), "pancreatic progenitor," "PDX1-positive pancreatic endoderm" or "PEC cell product" or equivalents thereof, such as "pancreatic endoderm cells" (PEC), are all precursor or progenitor pancreatic cells. PEC, as described herein, is a progenitor cell population after stage 4 differentiation (about day 12-14) and includes at least two major distinct populations: i) pancreatic progenitor cells that express PDX1 and NKX6.1 but do not express CHGA (or CHGA negative, CHGA−), or "non-endocrine multipotent progenitor sub-populations (CHGA−)", or "non-endocrine (CHGA−) sub-populations" or "non-endocrine (CHGA−) cells" or equivalents thereof; and ii) polyhormonal endocrine cells that express CHGA (CHGA positive, CHGA+), or "endocrine multipotent progenitor sub-populations (CHGA+)", or "endocrine (CHGA+) sub-populations" or "endocrine (CHGA+) cells" or equivalents thereof. The PEC pancreatic progenitor subpopulation that express PDX1 and NKX6.1 but not CHGA is also referred to as "non-endocrine multipotent pancreatic progenitor sub-population (CHGA−)" or "non-endocrine progenitor sub-population," "non-endocrine (CHGA−) sub-population," "non-endocrine (CHGA−) sub-population," "multipotent progenitor sub-population" and the like. The PEC polyhormonal endocrine cell subpopulation that expresses CHGA is also referred to as "cells committed to the endocrine lineage (CHGA+)," or endocrine cells" or "CHGA+ cells" and the like. Without being bound by theory, the cell population that expresses NKX6.1 but not CHGA is hypothesized to be the more active or therapeutic component of PEC, whereas the population of CHGA-positive polyhormonal endocrine cells is hypothesized to further differentiate and mature in vivo into glucagon-expressing islet cells. See Kelly et al. (2011) Cell-surface markers for the isolation of pancreatic cell types derived from human embryonic stem cells, *Nat Biotechnol.* 29(8):750-756, published online 31 Jul. 2011 and Schulz et al. (2012), A Scalable System for Production of Functional Pancreatic Progenitors from Human Embryonic Stem Cells, PLosOne 7(5): 1-17, e37004 which are herein incorporated by reference in their entirety.

Still, sometimes, pancreatic endoderm cells are used without reference to PEC as described above, but to refer to at least stages 3 and 4 type cells in general. The use and meaning will be clear from the context. Pancreatic endoderm have high levels of expression of markers selected from PDX1, NKX6.1, PTF1A, CPA1, cMYC, NGN3, PAX4, ARX and NKX2.2 markers, but do not substantially express genes which are hallmark of pancreatic endocrine cells, for example, CHGA, INS, GCG, GHRL, SST, MAFA, PCSK1 and GLUT1. Additionally, some "endocrine progenitor cells" expressing NGN3 can differentiate into other non-pancreatic structures (e.g., duodenum). Pancreatic endoderm or endocrine progenitor cell populations and methods thereof are also described in U.S. patent application Ser. No. 11/773,944, entitled Methods of producing pancreatic hormones, filed Jul. 5, 2007, and U.S. patent application Ser. No. 12/107,020, entitled METHODS FOR PURIFYING ENDODERM AND PANCREATIC ENDODERM CELLS DERIVED FORM HUMAN EMBRYONIC STEM CELLS, filed Apr. 21, 2008, which are herein incorporated by reference in their entirety.

Implanted cells include endocrine progenitor/precursor cells. An "endocrine progenitor/precursor cell" or equivalents thereof, as used herein, refers to a multipotent cell of the definitive endoderm lineage that expresses at least a marker from the list consisting of neurogenin 3 (NEUROG3), PDX1, PTF1A, SOX9, NKX6.1, HNF1b, GATA4, HNF6, FOXA1, FOXA2, GATA6, MYT1, ISLET1, NEUROD, SNAIL2, MNX1, IA1, RFX6, PAX4, PAX6, NKX2.2 and MAFB which can further differentiate into cells of the endocrine system including, but not limited to, pancreatic islet hormone-expressing cells. Endocrine progenitor/precursor cells are described in detail in at least Applicant's U.S. Pat. No. 8,129,182 issued Mar. 6, 2012, entitled ENDOCRINE PRECURSOR CELLS, PANCREATIC HORMONE-EXPRESSING CELLS AND METHODS OF PRODUCTION and U.S. Pat. No. 8,859,286 issued Oct. 14, 2014, entitled IN VITRO DIFFERENTIATION OF PLURIPOTENT STEM CELLS TO PANCREATIC ENDODERM CELLS (PEC) AND ENDOCRINE CELLS which are herein incorporated by reference in their entirety.

Implanted cells include endocrine cells. The term, "endocrine cell" or "pancreatic islet hormone-expressing cell," "pancreatic endocrine cell," "pancreatic islet cell", "pancreatic islets", "stem-cell derived beta cell", "beta cells" ("β cells") or "SC-beta cell" or equivalents thereof, are pancreatic endocrine cells capable of expressing insulin, but not glucagon, somatostatin, ghrelin, and pancreatic polypeptide. Pancreatic endocrine cells expressing markers characteristic of β cells can be characterized by their expression of insulin and at least one of the following transcription factors: PDX1, NKX2.2, NKX6.1, NeuroD1, ISL1, HNF3β, HB9, MAFA, and PAX6.

Implanted cells properly specified endocrine cells. As used herein the phrase "properly specified endocrine cells" or "stage 7 cultures" or "immature endocrine cells" including "immature beta cells" or equivalents thereof, refers to endocrine cell populations made in vitro which are capable of functioning in vivo, e.g., immature beta cells when transplanted secrete insulin in response to blood glucose.

Properly specified endocrine cells or stage 7 cultures may have additional characteristics including the following. In one embodiment, when transplanted, properly specified endocrine cells develop and mature to functional pancreatic islet cells. In one embodiment, a properly specified endocrine cell population is enriched for endocrine cells (or depleted of non-endocrine cells). In one embodiment, greater than about 50% of the cells in the properly specified endocrine cell population are CHGA+. In one embodiment, greater than about 60% or 70% or 80% or 90% or 95% or 98% or 100% of the cells in the properly specified endocrine cell population are CHGA+. In one embodiment, less than about 50% of the cells in the properly specified endocrine cell population are CHGA−. In one embodiment, less than about 15% of the cells in the properly specified endocrine cell population are CHGA−. In one embodiment, less than about 10% or 5% or 3% or 2% or 1% or 0.5% or 0% of the cells in the properly specified endocrine cell population are CHGA−. Further, expression of certain markers may be suppressed in properly specified endocrine cells such as NGN3 expression during stage 3. In one embodiment, properly specified endocrine cells have increased expression of NGN3 at stage 5. In one embodiment, properly specified endocrine cells are singly-hormonal (e.g. INS only, GCG only or SST only). In one embodiment, properly specified endocrine cells co-express other immature endocrine cell markers including NKX6.1 and PDX1. In one embodiment, properly specified endocrine cells may be both singly-hormonal and co-express other immature endocrine cell markers including NKX6.1 and PDX1. In one embodiment, properly specified endocrine cells may have more singly hormone-expressing INS cells as a percentage of the total INS population. In one embodiment, properly specified endocrine cells have at least 50% singly hormone-expressing INS cells as a percentage of the total INS population. In one embodiment, properly specified endocrine cells are CHGA+/INS+/NKX6.1+(triple positive). In one embodiment, greater than about 25% of the cells in the cell population are CHGA+/INS+/NKX6.1+(triple positive). In one embodiment, greater than about 30% or 40% or 50% or 60% or 70% or 80% or 90% or 95% 100% of the cells in the cell population are CHGA+/INS+/NKX6.1+(triple positive).

Implanted cells include immature endocrine cells. The term "immature endocrine cell,", specifically an "immature beta-cell," or equivalents thereof, refer to a cell derived from any other endocrine cell precursor including an endocrine progenitor/precursor cell, a pancreatic endoderm (PE) cell, a pancreatic foregut cell, a definitive endoderm cell, a mes-endoderm cell or any earlier derived cell later described, that expresses at least a marker selected from the group consisting of INS, NKX6.1, PDX1, NEUROD, MNX1, NKX2.2, MAFA, PAX4, SNAIL2, FOXA1 or FOXA2. Preferably, an immature beta-cell described herein expresses, INS, NKX6.1 and PDX1, and more preferably it co-expresses INS and NKX6.1. The terms "immature endocrine cell," "immature pancreatic hormone-expressing cell," or "immature pancreatic islet" or equivalents thereof refer for example to at least a unipotent immature beta cell or pre-beta cell as described in FIG. 45 of U.S. Pat. No. 8,859,286, which is herein incorporated by reference in its entirety, and do not include other immature cells, for example, the terms do not include an immature alpha (glucagon) cell, or an immature delta (somatostatin) cell, or an immature epsilon (ghrelin) cell, or an immature pancreatic polypeptide (PP). Methods of differentiating pluripotent cells to pancreatic endocrine precursor cells and pancreatic endocrine cells are further described in U.S. Pat. Nos. 9,012,218, 9,181,528, 9,234,178, 9,150,833, 9,096,832, 9,062,290 each of which is herein incorporated by reference in their entirety.

Implanted cells include functional beta-cells. The term, "functional beta-cells" or "mature beta cells" or equivalents thereof are pancreatic endocrine cells that display the well-established processes that ensure rapid and regulated glucose-stimulated insulin secretion ("GSIS"), specifically an increase in mitochondrial respiration/activity followed by the first phase and second phase of insulin secretion ("biphasic GSIS"). In detail, functional beta-cells exhibit at least one of the following characteristics of biphasic GSIS: (i) coupling of mitochondrial respiration/activity with insulin secretion; (ii) rapid insulin secretion response to heightened demand (here defined as high glucose concentration); (iii) ability to rapidly turn off insulin secretion after demand has subsided; (iv) ability for multiple rounds of "on-off" switching of insulin secretion; (v) ability to secrete the correct amount of insulin as dictated by demand; and (vi) ability to respond to multiple insulin secretagogues (for example, Exendin-4, or amino acids -L-Glutamine and L-Arginine). Functional beta-cells can be characterized by their expression of insulin and at least one of the following transcription factors: PDX1, NKX2.2, NKX6.1, NeuroD1, ISL1, HNF3β, HB9, PAX6, MAFA, SLC2A1, UCN3, and GLP1R.

As used herein, the terms "develop from pluripotent cells", "differentiate from pluripotent cells", "mature from pluripotent cells" or "produced from pluripotent cells", "derived from pluripotent cells", "differentiated from pluripotent cells" and equivalent expressions refer to the production of a differentiated cell type from pluripotent cells in vitro or in vivo.

Implanted cells include cell aggregates. The cell aggregates can be an aggregate of any of the cell types identified above. The aggregate may be substantially one cell type or may be a mixed cell population. As used herein, the terms "cluster" and "clump" or "aggregate" or any equivalent thereof can be used interchangeably, and generally refer to a group of cells that have been dissociated into single cells and then aggregated to form clusters or, have close cell-to-cell contact. The term "re-aggregated" as used herein refers to when clusters, clumps and/or aggregates are dissociated into smaller clusters, clumps and/or aggregates or single cells and then form new cell-to-cell contacts by re-aggregating into clusters, clumps and/or aggregates. This dissociation is typically manual in nature (such as using a Pasteur pipette), but other means of dissociation are contemplated. Aggregate suspension pluripotent or multipotent cell cultures are substantially as described in International Publications PCT/US2007/062755, titled COMPOSITIONS AND METHODS FOR CULTURING DIFFERENTIAL CELLS and PCT/US2008/082356, titled STEM CELL AGGREGATE SUSPENSION COMPOSITIONS AND METHODS OF DIFFERENTIATION THEREOF.

Implanted cells include single cell suspensions. The term, "single cell suspension" or equivalents thereof refers to a pluripotent, multipotent or terminally differentiated single cell suspension, or a single cell suspension derived from a pluripotent or multipotent cell, by any mechanical or chemical means. Which are described in more detail in U.S. Pat. No. 7,964,402 entitled Methods for culture and production of single cell populations of human embryonic stem cells and filed Jun. 21, 2011.

"Cells" refers to individual cells, cell lines, or cultures derived from such cells. A "culture" refers to a composition comprising isolated cells of the same or a different type. "Culture," "population" or "cell population" as used herein can be and are used interchangeably and its meaning will be clear depending on the context. For example, the term "population" can be a cell culture of more than one cell having the same identifying characteristics or it can be a culture of more than one cell types having different identifying characteristics. The term "sub-population" refers to a subset of a cell culture or population when used to describe certain cell types within the cell culture or cell population.

The term "cell lineage" as used herein refers to all of the stages of the development of a cell type, from the earliest precursor cell to a completely mature cell (i.e. a specialized cell). For example, a "definitive endoderm lineage cell" or a "PDX1-negative endoderm lineage cell" or a "PDX1-positive pancreatic endoderm lineage cell" or an "endocrine precursor lineage cell" or an "endocrine lineage cell" or an "immature beta lineage cell" and the like refer to cells derived from or differentiated from a definitive endoderm cell, a PDX1-negative endoderm cell, a PDX1-positive pancreatic endoderm cell and the like. A definitive endoderm cell is a lineage of a mesendoderm cell, one of its precursors. A PDX1-positive pancreatic endoderm cell is a lineage of a definitive endoderm cell, one of its precursors. An endocrine precursor in lineage of a PDX1-positive pancreatic cell, a definitive endoderm cell and a mesendoderm cell, all are its precursors. An immature beta cell in a lineage of an endocrine precursor cell, PDX1-positive pancreatic cell, a definitive endoderm cell and a mesendoderm cell, all are its precursors. A beta cell is the only lineage for example of an immature beta cell. Yet, all the endoderm lineage cells described herein are hES lineage cells.

The term "treating" or "ameliorating" or "healing" or equivalents thereof refers to a therapeutic intervention that ameliorates a sign or symptom. "Ameliorating" refers to the reduction in the number or severity of signs or symptoms.

The term "patient" or "host" or "mammalian host" or "subject" or equivalents thereof refers to living multi-cellular vertebrate organisms, a category that includes both human and non-human mammals. In some embodiments, the subject is a human subject. The preferred patient for treatment is a human. Patients implanted with a perforated combination product are "high-risk insulin-requiring patients", and exemplar populations include hypoglycemia-unaware, labile (brittle) T1D and transplant patients. The target patient populations may change over time of clinical use/experience in ways that are independent of the perforated combination product itself, but rather related to the nature of the immunosuppression regimen. For example, the perforated combination product might be used in 'all T1D' population using an ISD regimen that achieves operational tolerance.

The term "effective amount" or "therapeutically effective amount" or equivalents thereof refers to a quantity of an agent sufficient to achieve a desired effect in a subject or a cell being treated. For instance, this can be the amount of cells necessary to inhibit or to measurably reduce blood glucose levels and ultimately achieve homeostatic glycemic control. It can also mean an effective amount of an agent to change the function or structure of a cell or subject. A therapeutically effective amount of an agent may be administered in a single dose, or in several doses. However, the effective amount will be dependent on the particular agent applied, the subject being treated, the severity and type of the affliction, and the manner of administration.

As used herein, "biofouling" or "device fouling" or equivalents thereof refers to a process at the interface of an implantable biomedical device with the biological environment (e.g. host environment including but not limited to subcutaneous environment and the like), caused, in part, by non-specific adsorption of proteins to the device materials which promotes subsequent adhesion of host cells such as macrophages and fibroblasts on to the device surface. This process is commonly referred to as the foreign body response. Therefore, embodiments described herein are encapsulation devices that comprise biofouling-resistant surfaces. Such surfaces can be created or used based on surface hydrophilicity and charge, biomolecule functionalization, and drug elution. Reducing biofouling of the device generally, reduces the foreign body response and restores or maintains the cell survival, development, maturation and function. Embodiments herein discuss the use of non-woven fabrics for the purpose of inhibiting or decreasing device surface fouling, promote vascularization and therefore integration of the device and cells therein.

As used herein, "reduced hypoglycemia" means a reduction in the number of hypoglycemic episodes together with no deterioration in glycemic control, defined by <0.2% increase in HbA1c As used herein "reduced insulin dependence" means a reduction in the number and/or dose of exogenous insulin injections together with no deterioration in glycemic control, defined by <0.2% increase in HbA1c As used herein "retention" means the amount of PEC cells that remain within the perforated combination product. The perforated device shall retain the cell product during formulation, shelf life, surgical implantation, maturation and function.

As used herein "tissue capsule" means the foreign body capsule that forms around an implant. The perforated device and majority of its cellular contents are intended to be retained within the capsule during the implant period. The device shall retain cell product within its lumen during initial engraftment, prior to capsule formation.

"Engraftment" refers to differentiation of a progenitor or immature cell population into a mature cell type. For example, engraftment of a PDX1-positive pancreatic endoderm cell population maturing into a pancreatic endocrine cell population.

"Graft" refers to a differentiated cell population encapsulated or delivered in the devices herein. For example, a mature pancreatic endocrine cell graft.

The term "essentially" or "substantially" means mostly or a de minimus or a reduced amount of a component or cell present in any cell population or culture, e.g., immature beta cell cultures are "essentially or substantially immature beta cells expressing INS, NKX6.1 and PDX1 and not essentially or substantially expressing NGN3". Other examples include but not limited to "essentially or substantially hES cells", "essentially or substantially definitive endoderm cells", "essentially or substantially foregut endoderm cells", "essentially or substantially PDX1-negative foregut endoderm cells", "essentially or substantially PDX1-positive pancreatic endoderm cells", "essentially or substantially pancreatic endocrine precursor cells", "essentially or substantially pancreatic endocrine cells" and the like.

With respect to cells in cell cultures or in cell populations, the term "substantially free of" means that the specified cell type of which the cell culture or cell population is free, is present in an amount of less than about 10%, less than about 9%, less than about 8%, less than about 7%, less than about 6%, less than about 5%, less than about 4%, less than about 3%, less than about 2% or less than about 1% of the total number of cells present in the cell culture or cell population.

The term "non-woven fabric" or equivalents thereof, includes, but is not limited to, bonded fabrics, formed fabrics, or engineered fabrics, that are manufactured by processes other than, weaving or knitting.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Cell Delivery Devices

Cell delivery devices also called cell encapsulation devices or cell retention devices or cell containment devices or bioartificial organs are devices which provide a housing that entirely or partially encapsulates the cells from the host including but not limited to the host immune system.

The cells can be any cells of interest. The cells can be homogenous or heterogeneous cell populations, or cells producing one or more biologically active substances of interest. Implanted cells may not initially be therapeutically active when first implanted, e.g. pancreatic progenitors or PDX1-positive pancreatic endoderm, but once transplanted they further develop and mature and have a therapeutic effect. The implanted cells can be individual cells in suspension or cell aggregates.

For example, diabetes, or one or more symptoms thereof, can be ameliorated or reduced for a period of time following implantation of a cell suitable for transplantation into a subject suffering from diabetes. In one embodiment, the cell delivery device is loaded with PDX1-positive pancreatic endoderm cells. In one embodiment, the cell delivery device is loaded with pancreatic progenitor cells. In one embodiment, the cell delivery device is loaded with pancreatic endocrine precursor cells. In one embodiment, the cell delivery device is loaded with pancreatic endocrine cells. In one embodiment, the cell delivery device is loaded with mature beta cells.

In one embodiment, the implanted cells include totipotent cells. In one embodiment, the implanted cells include pluripotent cells. In one embodiment, the implanted cells include multipotent cells. Multipotent cells include endocrine precursor cells, PDX1-positive pancreatic endoderm cells, definitive endoderm cells, or mesendoderm cells which can give rise to each of the pancreatic alpha, beta, delta and gamma islet cells. In one embodiment, the implanted cells include unipotent cells. Unipotent cells include immature beta cells which have the capacity to differentiate into only insulin beta cells but not glucagon (alpha) cells, somatostatin (delta) cells and pancreatic polypeptide (gamma) cells for example. In one embodiment, the implanted cells include terminally differentiated cells.

In one embodiment, the implanted cells are well known, publicly available immortalized cell lines. The invention described herein is useful with all hES cell lines, and at least hESC and iPSC, e.g., CyT25, CyT203, CyT212, BG01, BG02, B G03, which are available for commercial purchase from WiCell on the world wide web at wicell.org/home/stem-cell-lines/order-stem-cell-lines/obtain-stem-cell-lines.cmsx. Cells suitable for the practice of this invention are any now known or later made pluripotent cells. WiCell lists hundreds of other commercially available hES stem cell lines. A skilled artisan knows how to locate and purchase commercially available stem cells for use in this invention from the literature and publically available databases including for example the National Institutes of Health (NIH) Stem Cell Registry, the Human Embryonic Stem Cell Registry and the International Stem Cell Registry located at the University of Massachusetts Medical School, Worcester, Mass., USA. These databases are periodically updated as cell lines become available and registration obtained. There are at least 254 iPSC commercially available lines listed with the International Stem Cell Registry and 1211 commercially available hESC lines. In one embodiment, the pluripotent implanted cells are human embryonic stem (hES) cells, human embryonic germ (hEG) cells, induced pluripotent stem cells (aka "iPS cells" or "iPSCs cells), parthenogenic cells, embryos derived by somatic cell nuclear transfer and the like. In one embodiment, the implanted cells are differentiated cells derived from pluripotent cells such as human embryonic stem (hES) cells, human embryonic germ (hEG) cells, induced pluripotent stem cells (aka "iPS cells" or "iPSCs cells), parthenogenic cells, embryos derived by somatic cell nuclear transfer and the like. Pluripotency can also be determined through characterization of the cells with respect to surface markers, transcriptional markers, karyotype, and ability to differentiate to cells of the three germ layers. These characteristics are well known to those of ordinary skill in the art. For example, human pluripotent stem cells can be defined or characterized by the presence of several transcription factors and cell surface proteins including transcription factors Oct-4, Nanog, and Sox-2, which form the core regulatory complex ensuring the suppression of genes that lead to differentiation and the maintenance of pluripotency; and cell surface antigens, such as the glycolipids SSEA3, SSEA4 and the keratin sulfate antigens, Tra-1-60 and Tra-1-81, and alkaline phosphatase.

As such a skilled person could perform the disclosed methods and use the disclosed devices without the need to use human embryos and without presupposing a destructive use of human embryos to have taken place at any earlier point in time. Indeed, the derivation of hES cell lines from parthenogenetically activated oocytes would be one such way to carry out the invention (e.g. according to WO 03/046141 which is herein incorporated by reference in its entirety). Other methods exist for deriving pluripotent stem cells, such as mammalian ES cells, without destruction of the embryo. Briefly, Advanced Cell Technology (Worcester, Mass., USA) published 3 scientific journal articles describing the derivation of mouse and human ES cells from single blastomeres leaving the embryo intact and thus not causing its destruction. In late 2005, Chung et al. first described methods for making mouse ES cells from a single blastomere. See Chung et al. (2006) *Nature* 439: 216-219, published online Oct. 16, 2005. Chung et al. (2006) described taking biopsies from an embryo using micromanipulation techniques similar to techniques used for pre-implantation genetic diagnosis (PGD); see page 217. At the time, Chung et al. (2006) co-cultured the blastomere cell lines with other embryonic stem cells. See Chung et al. (2008) Human Embryonic Stem Cell Lines Generated without Embryo Destruction, *Cell Stem Cell* 2: 113-117. But a later 2008 study by the same Chung. et al., supra, demonstrated that hES cell lines did not require co-culturing with ES cells at all because culturing the isolated blastomeres in medium with laminin enhanced their ability to give rise to hESCs. See Chung et al. (2008), Human Embryonic Stem Cell Lines Generated without Embryo Destruction, *Cell Stem Cell* (2):113-117, p. 116, published online Jan. 10, 2008. Further, that hES cells obtained in this manner had the same characteristics as other human pluripotent stem cells including hES cells including being capable of maintaining an undifferentiated state for over six (6) months, and showed normal karyotype and expression of markers of pluripotency, including Oct-4, SSEA-3, SSEA-4, TRA-1-60, TRA-1-81, Nanog and Alkaline Phosphatase; and can differentiate and form derivatives of all three (3) embryonic germ layers both in vitro and form in teratomas in vivo.

The implanted cells can include differentiated, dedifferentiated and transdifferentiated cells. In additional embodiments, the implanted cells can include singly hormonal or polyhormonal cells. In further embodiments, the implanted cells include reprogrammed cells. In some embodiments, the implanted cells include mesoderm cells.

In yet other embodiments, the implanted cells include definitive endoderm cells. In accordance with certain embodiments, the definitive endoderm cells are mammalian cells, and in a preferred embodiment, the definitive endoderm cells are human cells. In some embodiments, one or more markers selected from SOX17, CXCR4, MIXL1, GATA4, HNF3β, GSC, FGF17, VWF, CALCR, FOXQ1, CMKOR1 and CRIP1 are expressed in definitive endoderm cells. In other embodiments, one or more markers selected from OCT4, alpha-fetoprotein (AFP), Thrombomodulin (TM), SPARC, SOX7, and HNF4alpha are not expressed or significantly expressed in definitive endoderm cells. Definitive endoderm cell populations and methods of production thereof are also described in U.S. application Ser. No. 11/021,618, entitled DEFINITIVE ENDODERM, filed Dec. 23, 2004, which is incorporated by reference in its entirety.

In some embodiments, the implanted cells include endocrine progenitor/precursor cells. In other embodiments, the implanted cells include functional beta-cells. In further embodiments, the implanted cells include, but are not limited to, islets such as human islets of Langerhans, pig islets, and rat islets. They can include terminally differentiated alpha (α), beta (β), delta (δ) and/or pancreatic peptide (PP) cells. In one aspect, an embodiment consistent with the present disclosure is used for transplantation of islets of Langerhans cells. In some embodiments, the implanted cells include other cell types, such as hepatocytes, spleen, pancreas, gall bladder, kidney, and other tissues having exocrine function. In some embodiments, the implanted cells include neuroendocrine cells, proliferating cells and cell lines that secrete hormones, cytokines, lymphokines, cell growth regulators, or other cells having metabolic functions. As would be apparent to one of ordinary skill in the art, these cells and tissue can be obtained from mammalian tissue, primary cultured cells, cultured cell lines producing biological products and genetically engineered cultured cell lines. The implanted cells can also be genetically engineered to produce a desired molecule such as a protein, peptide, nucleic acid or other biologically active agent. Examples include cells engineered to express an enzyme missing or defective in the recipient or which express a therapeutic agent such as a toxin directed against cancer cells.

In some embodiments, the implanted cells include PDX1-negative foregut endoderm cells, such as cells that express SOX17, HNF1β (HNF1B), HNF4alpha (HNF4A) and FOXA1 markers but do not substantially express PDX1, AFP, SOX7, or SOX1. In other embodiments, the implanted cells include PDX1-positive, dorsally-biased, foregut endoderm cells.

In embodiments, the implanted cells are in a media free of animal-sourced products. In another embodiment, the implanted cells are in a xeno-free media. The implanted cells can be in a media supplemented with growth factors. The term "supplemental growth factor" is used in its broadest context and refers to a substance that is effective to promote the growth of a pluripotent cell, maintain the survival of a cell, stimulate the differentiation of a cell, and/or stimulate reversal of the differentiation of a cell. Such substances include, but are not limited to, cytokines, chemokines, small molecules, neutralizing antibodies, and proteins. Growth factors may also include intercellular signaling polypeptides, which control the development and maintenance of cells as well as the form and function of tissues. In preferred embodiments, the supplemental growth factor is selected from the group comprising steel cell factor (SCF), oncostatin M (OSM), ciliary neurotrophic factor (CNTF), Interleukin-6 (IL-6) in combination with soluble Interleukin-6 Receptor (IL-6R), a fibroblast growth factor (FGF), a bone morphogenetic protein (BMP), tumor necrosis factor (TNF), and granulocyte macrophage colony stimulating factor (GM-CSF).

In one embodiment, the implanted cells are substantially similar to that described in D'Amour et al. "Production of Pancreatic Hormone-Expressing Endocrine Cells From Human Embryonic Stem Cells" (Nov. 1, 2006) Nature Biotechnology 24, 1392-1401 which is herein incorporated by reference in its entirety. D'Amour et al. describe a 5 step differentiation protocol: stage 1 (results in mostly definitive endoderm production), stage 2 (results in mostly PDX1-negative foregut endoderm production), stage 3 (results in mostly PDX1-positive foregut endoderm production), stage 4 (results in mostly pancreatic endoderm also called multipotent pancreatic progenitor or pancreatic endocrine progenitor production) and stage 5 (results in mostly hormone-expres sing endocrine cell production).

In one embodiment, the implanted cells are substantially similar to that described in Schulz et al. A Scalable System for Production of Functional Pancreatic Progenitors from Human Embryonic Stem Cells PLoS One 7:5 1-17 (2012) which is herein incorporated in its entirety by reference. Schulz et. al. describe hESC expansion and banking methods and a suspension-based differentiation system. Specifically, undifferentiated pluripotent cells were aggregated into clusters in dynamic rotational suspension culture, followed by differentiation en masse for two weeks with a four-stage protocol. Briefly, to from hES cell aggregate suspensions, hESC monolayers are dissociated with Accutase (Innovative Cell Technologies), collected and resuspended at $1 \times 10^6$ cells/mL in StemPro hESC SFM (Life Technologies; combined DMEM/F12 containing Glutamax, StemPro hESC supplement, BSA, and 1% (v/v) Penicillin/streptomycin; omitted FGF-2 and 2-Mercaptoethanol). The single cell suspensions were dispensed to non-TC treated 6-well plates (5.5 mL/well) and rotated at 95 rpm on an Innova 2000 rotator (New Brunswick Scientific), or dispensed to 500 mL Nalgene filter receiver storage bottles (150 mL/bottle) and rotated at 65 rpm on a Sartorius Certomat RM-50 rotator (configured with a 5 cm axis of rotation). Cells were rotated overnight in a 37° C./8% CO2 incubator and formed aggregates of approximately 100-200 µm. For aggregate diameters between 100-200 µm rotation speeds between 60-140 rpm for a 6-well dish can be used; rotation speeds between 5-20 rpm for a 500 mL bottle can be used. Differentiation of suspension aggregates involved only a few modifications from D'Amour. The TGF-βRI kinase Inhibitor IV was included during Stage-2, and retinoic acid was replaced with a more stable retinoid analog, TTNPB (3 nM), during Stage-3. The growth factors KGF (50 ng/mL) and EGF (50 ng/mL) were added to Stage-4 to preserve cell mass. Noggin (50 ng/mL) was also included at Stage-4.

In one embodiment, implanted cells are substantially similar to that described in Agulnick et al. Insulin-Producing Endocrine Cells Differentiated In Vitro From Human Embryonic Stem Cells Function in Macroencapsulation Devices In Vivo *Stem Cells Translationalmedicine* 4:1-9 (2015) which is herein incorporated in its entirety by reference. Agulnick et al. describe a modified the protocol for making pancreatic progenitors cells such that 73%-80% of the cell population consisted of PDX1-positive (PDX1+) and NKX6.1+ pancreatic progenitors. The pancreatic progenitor cells were further differentiated into islet-like cells (ICs) that reproducibly contained 73%-89% endocrine cells, of which approximately 40%-50% expressed insulin. A large fraction of these insulin-positive cells were single hormone-positive and expressed the transcription factors PDX1 and NKX6.1. We modified the protocol for making pancreatic progenitors cells such that 73%-80% of the cell population consisted of PDX1-positive (PDX1+) and NKX6.1+PPs. The PPs were further differentiated into islet-like cells (ICs) that reproducibly contained 73%-89% endocrine cells, of which approximately 40%-50% expressed insulin. A large fraction of these insulin-positive cells were single hormone-positive and expressed the transcription factors PDX1 and NKX6.1. Agulnick et al. describe a protocol wherein the Schulz et al. 2012 protocol was modified by additionally treating with activin A, Wnt3A, and heregulin β1 at stage 3 (days 5-7) and with activin A and heregulin β1 at stage 4 (days 7-13).

Various cell compositions derived from pluripotent stem cells are described herein and can be found in Applicant's U.S. patent application Ser. No. 10/486,408, entitled METHODS FOR CULTURE OF HESC ON FEEDER CELLS, filed Aug. 6, 2002; Ser. No. 11/021,618, entitled DEFINITIVE ENDODERM, filed Dec. 23, 2004; Ser. No. 11/115,868, entitled PDX1 EXPRESSING ENDODERM, filed Apr. 26, 2005; Ser. No. 11/165,305, entitled METHODS FOR IDENTIFYING FACTORS FOR DIFFERENTIATING DEFINITIVE ENDODERM, filed Jun. 23, 2005; Ser. No. 11/573,662, entitled METHODS FOR INCREASING DEFINITIVE ENDODERM DIFFERENTIATION OF PLURIPOTENT HUMAN EMBRYONIC STEM CELLS WITH PI-3 KINASE INHIBITORS, filed Aug. 15, 2005; Ser. No. 12/729,084 entitled PDX1-EXPRESSING DORSAL AND VENTRAL FOREGUT ENDODERM, filed Oct. 27, 2005; Ser. No. 12/093,590, entitled MARKERS OF DEFINITIVE ENDODERM, filed Nov. 14, 2005; Ser. No. 11/993,399, entitled EMBRYONIC STEM CELL CULTURE COMPOSITIONS AND METHODS OF USE THEREOF, filed Jun. 20, 2006; Ser. No. 11/588,693, entitled PDX1-EXPRESSING DORSAL AND VENTRAL FOREGUT ENDODERM, filed Oct. 27, 2006; Ser. No. 11/681,687, entitled ENDOCRINE PROGENITOR/PRECURSOR CELLS, PANCREATIC HORMONE-EXPRESSING CELLS AND METHODS OF PRODUCTION, filed Mar. 2, 2007; Ser. No. 11/807,223, entitled METHODS FOR CULTURE AND PRODUCTION OF SINGLE CELL POPULATIONS OF HESC, filed May 24, 2007; Ser. No. 11/773,944, entitled METHODS OF PRODUCING PANCREATIC HORMONES, filed Jul. 5, 2007; Ser. No. 11/860,494, entitled METHODS FOR INCREASING DEFINITIVE ENDODERM PRODUCTION, filed Sep. 24, 2007; Ser. No. 12/099,759, entitled METHODS OF PRODUCING PANCREATIC HORMONES, filed Apr. 8, 2008; Ser. No. 12/107,020, entitled METHODS FOR PURIFYING ENDODERM AND PANCREATIC ENDODERM CELLS DERIVED FORM HUMAN EMBRYONIC STEM CELLS, filed Apr. 21, 2008; Ser. No. 12/618,659, entitled ENCAPSULATION OF PANCREATIC LINEAGE CELLS DERIVED FROM HUMAN PLURIPOTENT STEM CELLS, filed Nov. 13, 2009; Ser. Nos. 12/765,714 and 13/761,078, both entitled CELL COMPOSITIONS FROM DEDIFFERENTIATED REPROGRAMMED CELLS, filed Apr. 22, 2010 and Feb. 6, 2013; Ser. No. 11/838,054, entitled COMPOSITIONS AND METHODS USEFUL FOR CULTURING DIFFERENTIABLE CELLS, filed Aug. 13, 2007; Ser. No. 12/264,760, entitled STEM CELL AGGREGATE SUSPENSION COMPOSITIONS AND METHODS OF DIFFERENTIATION THEREOF, filed Nov. 4, 2008; Ser. No. 13/259,15, entitled SMALL MOLECULES SUPPORTING PLURIPOTENT CELL GROWTH, filed Apr. 27, 2010; PCT/US11/25628, entitled LOADING SYSTEM FOR AN ENCAPSULATION DEVICE, filed Feb. 21, 2011; Ser. No. 13/992,931, entitled AGENTS AND METHODS FOR INHIBITING PLURIPOTENT STEM CELLS, filed Dec. 28, 2010; and U.S. Design application No. 29/408,366 filed Dec. 12, 2011; Ser. No. 29/408,368 filed Dec. 12, 2011; Ser. No. 29/423,365 filed May 31, 2012; and Ser. No. 29/447,944 filed Mar. 13, 2013; and U.S. application Ser. No. 14/201,630 entitled 3-DIMENSIONAL LARGE CAPACITY CELL ENCAPSULATION DEVICE ASSEMBLY, filed Mar. 7, 2014; and U.S. application Ser. No. 14/106,330 entitled IN VITRO DIFFERENTIATION OF PLURIPOTENT STEM CELLS TO PANCREATIC ENDODERM CELLS (PEC) AND ENDOCRINE CELLS, filed Dec. 13, 2013 all of which are herein incorporated by reference in their entirety.

Various cell compositions derived from pluripotent stem cells are described herein and can be found in applications exclusively licensed by Applicant: U.S. Patent Publication no. 2009/0269845 entitled Pluripotent cells filed Aril 24, 2008; U.S. Patent Publication no. 2011/0014703 entitled Differentiation of Human Embryonic Stem Cells filed Jul. 20, 2010; U.S. Patent Publication no. 2011/0014702 entitled Differentiation of Human Embryonic Stem Cells filed Jul. 19, 2010; U.S. Patent Publication no. 2011/0151561 entitled Differentiation of Human Embryonic Stem Cells filed Dec. 16, 2010; U.S. Patent Publication no. 2010/0112692 entitled Differentiation of Human Embryonic Stem Cells filed Oct. 22, 2009; U.S. Patent Publication no. 2012/0052576 entitled Differentiation of Pluripotent Stem Cells filed Aug. 17, 2011; U.S. Patent Publication no. 2010/0112693 entitled Differentiation of human pluripotent stem cells filed Oct. 23, 2009; U.S. Patent Publication no. 2011/0151560 entitled Differentiation of human embryonic stem cells filed Dec. 16, 2010; U.S. Patent Publication no. 2010/0015100 entitled Differentiation of human embryonic stem cells filed Jul. 31, 2008; U.S. Patent Publication no. 2009/0170198 entitled Differentiation of human embryonic stem cells filed Nov. 25, 2008; U.S. Patent Publication no. 2015/0329828 entitled Use of Small Molecules to Enhance Mafa Expression in Pancreatic Endocrine Cells filed May 7, 2015; U.S. Patent Publication no U.S. 2013/0330823 entitled Differentiation of Human Embryonic Stem Cells into Pancreatic Endocrine Cells filed Jun. 6, 2013; International patent publication no. WO 2013/192005 entitled Differentiation of human embryonic stem cells into pancreatic endocrine cells filed Jun. 13, 2013; U.S. Patent Publication no U.S. 2014/0242693 entitled Suspension and clustering of human pluripotent stem cells for differentiation into pancreatic endocrine cells filed Dec. 30, 2013; U.S. Patent Publication no U.S. 2014/0295552 entitled Suspension and clustering of human pluripotent stem cells for differentiation into pancreatic endocrine cells filed Jun. 17, 2014; International patent publication no. WO 2015/065524 entitled Suspension and clustering of human pluripotent stem cells for differentiation into pancreatic endocrine cells filed May 21, 2014; U.S. Patent Publication no U.S. 2013/0330823 entitled Differentiation of Human Embryonic Stem Cells into Pancreatic Endocrine Cells filed Jun. 6, 2013; U.S. Patent Publication no U.S. 2014/0186953 entitled Differentiation of Human Embryonic Stem Cells Into Pancreatic Endocrine Cells Using HB9 Regulators filed Dec. 18, 2013; U.S. application Ser. No. 14/963,730 filed Dec. 9, 215; U.S. application Ser. No. 14/898,015 filed Dec. 11, 2015 all of which are herein incorporated by reference in their entirety.

In one embodiment, the implanted cells are encapsulated using a bio-compatible polyethylene glycol (PEG). PEG-based encapsulation is described in more detail in U.S. Pat. No. 7,427,415, entitled IMPLANTATION OF ENCAPSULATED BIOLOGICAL MATERIALS FOR TREATING DISEASES; U.S. Pat. No. 6,911,227, entitled GELS FOR ENCAPSULATION OF BIOLOGICAL MATERIALS; and U.S. Pat. Nos. 6,911,227, 5,529,914, 5,801,033, 6,258,870, entitled GELS FOR ENCAPSULATION OF BIOLOGICAL MATERIALS, which are all herein incorporated by reference in their entireties.

In another embodiment, the delivery device is a TheraCyte (formerly Baxter) device (Irvine, Calif.). TheraCyte cell delivery devices are further described in U.S. Pat. Nos. 6,773,458; 6,156,305; 6,060,640; 5,964,804; 5,964,261; 5,882,354; 5,807,406; 5,800,529; 5,782,912; 5,741,330; 5,733,336; 5,713,888; 5,653,756; 5,593,440; 5,569,462; 5,549,675; 5,545,223; 5,453,278; 5,421,923; 5,344,454; 5,314,471; 5,324,518; 5,219,361; 5,100,392; and 5,011,494, which are all herein incorporated by reference in their entireties.

In another embodiment, the delivery device is a device as substantially described in U.S. Pat. No. 8,278,106, and as described in U.S. application Ser. No. 14/201,630 filed Mar. 7, 2014, and in U.S. Design Nos. 29/447,944, 29/509,102, 29/484,363, 29/484,360, 29/484,359, 29/484,357, 29/484,356, 29/484,355, 29/484,362, 29/484,358, 29/408,366, 29/517,319, 29/408,368, 29/518,513, 29/518,516, 29/408,370, 29/517,144, 29/423,365, 29/530,325, which are all herein incorporated by reference in their entireties.

The embodiments of the cell delivery devices described herein are not intended to be limited to certain size, shape, design, volume capacity, and/or materials used to make the cell delivery devices, so long as the implanted cells are able to produce insulin in response to blood glucose.

The tissue, graft or cells in the core (also called the cell chamber or lumen) of the cell delivery device may be immobilized on an immobilizing matrix, such as a hydrogel or extracellular matrix components. In addition, the core of the cell delivery device may contain an insert to create a "cell free" zone in the center of the core, so as to further reduce the possibility of a necrotic core of cells in the center of the device.

The cell delivery device can have any configuration appropriate for maintaining biological activity and providing access for delivery of the product or function, including for example, cylindrical, rectangular, disk-shaped, patch-shaped, ovoid, stellate, or spherical. Moreover, the cell delivery device can be coiled or tubular or wrapped into a mesh-like or nested structure. If the cell delivery device is to be retrieved at some time after it is implanted, configurations which tend to lead to migration of the cell delivery devices from the site of implantation (such as spherical devices small enough to travel in the recipient's blood vessels) should be avoided. Embodiments of this invention include shapes that offer high structural integrity and are easy to retrieve from the host. Such shapes include rectangular patches, disks, cylinders, and flat sheets.

In other embodiments, cell delivery device or large capacity assembly consist of one or two or more seals that further partition the lumen of the cell delivery device, i.e., a partition seal. See, e.g. Applicant's U.S. Design applications 29/408366, 29/408368, 29/408370 and 29/423,365.

The cell delivery device may be implanted subcutaneously but other locations may be suitable for implantation, such as the intraperitoneal cavity or wall, an intramuscular site, an abdominal fat pad, or another suitable location. Alternatively, the cell delivery device disclosed can be implanted partially intraperitoneally in a host body, including into the omentum or other appropriate site and extend into the subcutaneous environment. In one embodiment the cells may be loaded into the portion of the device extending into the subcutaneous environment while the rest of the device is in the intraperitoneal environment. In another embodiment, the cell delivery device may be implanted into the brain, spinal cord area or any other organ as required to elicit a therapeutic effect from transplanted cells. In most instances, the host is a human, but may be another mammal or non-mammalian animal.

Expanded devices: In one embodiment, there is provided cell delivery devices or large capacity assemblies that are expandable.

Refillable devices: Exchange of the cells within the implanted cell delivery device may be accomplished by removing cells from the cell delivery device and subsequently injecting a therapeutic agent or cells directly into the reservoir, chamber, lumen, container or compartment of the implanted cell delivery device, e.g., subdermally or subcutaneously. Injection of cells/therapeutic agent can be achieved using a syringe inserted into a port.

Alternatively, in another embodiment, the devices or assemblies provided herein contain no ports of entry or exit, i.e. the devices are said to be port-less; and cells are loaded into the delivery devices prior to implanting them into the implant site.

Multi-Chamber Modular Devices

In one embodiment, the implanted cells are delivered in a macro cell encapsulation/delivery device also referred to as a large capacity assembly or large capacity device. As used herein, the terms "large capacity assembly" or "large capacity device" refers to a cell encapsulation device consisting of multiple or a plurality of cell chambers. In one embodiment, the large capacity assembly consists of at least 1, 2, 4, 5, 6, 7, 8, 9, 10 or more cell chambers. In another embodiment, the large capacity assembly is made such that a large capacity assembly can consist of any number of cell chambers (or a modular unit). For example, a modular unit can consist of 1, 2, 3, 4, 5, 6, 7, 8, 9, 10 or more cell chambers, which can depend on the number or dose of cells required for the treatment of the disease as described in U.S. Pat. No. 8,278,106 which is herein incorporated in its entirerty by reference. The number of chambers in the delivery device is determined based on the volume and/or number of cells that are to be transplanted.

3-dimensional large capacity devices: In one embodiment the cell delivery devices or large capacity assemblies are provided containing a plurality or multiplicity of cell chambers interconnected by cell-free zones, e.g. folds and bends as described in U.S. application Ser. No. 14/201,630 filed Mar. 7, 2014. In one embodiment, the large capacity assembly comprises at least two cell chambers and at last two configurations folded and unfolded wherein the folded configuration has a smaller footprint than the unfolded configuration. Hence, as used herein, the term "cell encapsulation device" or "cell delivery device" can mean a single device consisting of one cell chamber or one device consisting of multiple cell chambers as in a large capacity device or multiple cell chambers in a 3-dimensional device or device assemblies described in U.S. Pat. No. 8,278,106 and U.S. application Ser. No. 14/201,630 filed Mar. 7, 2014, which are both herein incorporated by reference in their entireties. Thus, cell delivery device, large capacity assembly, and 3-dimensional device can be used interchangeably.

Various Cell Delivery Device Configurations

Cell delivery devices include various layers each of which serves a function or multiple functions. In some embodiments, the cell delivery device includes both a cell-excluding membrane and a non-woven fabric.

Cell-excluding membrane: This layer inhibits cellular components of the immune system such as T-cells and the like from entering the device. This layer also serves to keep the therapeutic cells from exiting the device. This layer allows the encapsulated biologically active substance of interest to pass (e.g., insulin, glucagon, pancreatic polypeptide and the like), making the active substance available to the target cells outside the cell delivery device and in the patient's body. This layer ideally allows nutrients naturally present in the host to pass through the membrane to provide essential nutrients to the encapsulated cells. Cell-excluding membranes have been described in the art including those patents previously described above by Baxter including, U.S. Pat. Nos. 6,773,458; 6,520,997; 6,156,305; 6,060,640; 5,964,804; 5,964,261; 5,882,354; 5,807,406; 5,800,529; 5,782,912; 5,741,330; 5,733,336; 5,713,888; 5,653,756; 5,593,440; 5,569,462; 5,549,675; 5,545,223; 5,453,278; 5,421,923; 5,344,454; 5,314,471; 5,324,518; 5,219,361; 5,100,392; and 5,011,494 which are all incorporated herein by reference in their entirety. In some embodiments this layer is perforated.

Film: In some embodiments, the cell delivery device includes a film layer, film ring or film weld. The film is a binding or adhesive layer that is only present in the weld that helps adhere or bond at least two or more layers together. In some embodiments the film is only on the interior face (chamber facing) of the non-woven fabric (see below), to eliminate the smooth surface that it creates if it were on the outer face (host facing), which inhibits anchoring. In some embodiments, the film is on the interior face (chamber facing) of the cell-excluding membrane. The film is not part of the chamber; it is located in the weld.

Mesh: A woven mesh provides structural rigidity to each device and protects the cell excluding membrane by serving as a protective exoskeleton. In some embodiments, the non-woven mesh is not included in the device configuration. To address the loss of rigidity resulting from not including woven mesh from the device design, a double layer of non-woven fabric and/or a ring of non-woven fabric on the outside of the device may be used.

Non-woven fabric: A cell encapsulation device that becomes well-integrated into the host after implantation is provided. To this end, reducing, inhibiting or decreasing biofouling at the device-host interface is critical for device integration. In one embodiment, a non-woven fabric is used to explore whether, along with providing structural integrity, it can increase vascularization and decrease or inhibit biofouling. It one embodiment, the non-woven fabric provides protection to the cell-excluding membrane from direct contact with the woven mesh, and additional material for device anchoring to the host or device integration. There are numerous types of non-woven fabrics, varying in tightness of weave and thickness of the sheet. In one embodiment, the filament cross section is trilobal. The non-woven fabric can be a bonded fabris, formed fabric, or engineered fabric, that is manufactured by processes other than, weaving or knitting. In some embodiments, the non-woven fabric is a porous, textile-like material, usually in flat sheet form, composed primarily or entirely of fibers, such as staple fibers assembled in a web, sheet or batt. The structure of the non-woven fabric is based on the arrangement of, for example, staple fibers that are typically arranged more or less randomly.

Non-woven fabrics can be created by a variety of techniques known in the textile industry. Various methods may create carded, wet laid, melt blown, spunbonded, or air laid nonwovens. Exemplary methods and substrates are described in U.S. Application Publication No. 2010/0151575, the teachings of which are incorporated herein by reference. In one embodiment the non-woven fabric is polytetrafluoroethylene (PTFE). In one embodiment the non-woven fabric is a spunbound polyester.

The density of the non-woven fabric may be varied depending upon the processing conditions. In one embodiment the non-woven fabric is a spunbound polyester with a basic weight from about 0.40 to about 1.00 (oz/yd$^2$) a nominal thickness of about 127 to about 228 µm and a fiber diameter of about 0.5 to about 26 µm. In one embodiment, the filament cross section is trilobal. In some embodiments, the non-woven fabrics are biocompatible and/or bioabsorbable.

Historically, cell delivery devices have a simple configuration, including just the cell-excluding membrane for therapeutic cell containment, film for welding, and the woven mesh (EN-A configuration).

FIGS. 1 A-D are exploded views of certain embodiments of a cell delivery device. The figures depict an EN20, which is short-hand for a drug delivery device that has the capacity to support about twenty microliters (20 µl) of implanted cells upon maturation, in an unperforated form. As shown in FIGS. 1 A-D, the device can have additional various layers of mesh, film, membrane, and non-woven fabric. Each configuration is manufactured as a "sandwich" that is assembled as a stack of materials and sealed.

Table 1 below describes cell delivery device configurations. Each wall of the device may be comprised of identical number of layers and type of materials, or different number and type of layers depending on the function required and imparted by the layer. The device chamber or housing is created by welding or bonding the periphery and loading the chamber is accomplished by the port tubing. The first row and the bottom row of Table 1 are the layers exposed to or would be in contact with the host upon implantation.

TABLE 1

Variations in cell delivery device materials

| Device | EN20B1 | EN20B2 | EN20B3 | EN20B4 |
|---|---|---|---|---|
| Material | Non-woven fabric | NWF | Mesh | Mesh |
| Layer | Film | Film | Film | Film |
| Configuration | Heat Laminated Non-woven fabric (×2) to Cell-Excluding Membrane | Mesh Heat Laminated Non-woven fabric to Cell-Excluding Membrane | Heat Laminated Non-woven fabric to Cell-Excluding Membrane | Heat Laminated Non-woven fabric to Cell-Excluding Membrane |
| | Film | Film | Film | Film |
| | Tubing | Tubing | Tubing | Tubing |
| | Film | Film | Film | Film |
| | Heat Laminated Non-woven fabric ×2 | Heat Laminated Non-woven fabric | Heat Laminated Non-woven fabric | Heat Laminated Non-woven fabric |
| | Membrane | Membrane | Membrane | Membrane |
| | Film | Mesh | Film | Film |
| | Non-woven fabric | Film Non-woven fabric | Mesh | Mesh |

For example in FIG. 1A: the delivery device (EN20B1) has a non-woven fabric ring 51, film ring 52, a membrane layer wherein two layers of non-woven fabric are laminated, such as heat laminated, to the cell-excluding membrane (53) the non-woven fabric layer faces out toward the host while the cell-excluding membrane layer faces in toward the chamber or the implanted cells, and a film ring (54) at the periphery or weld. This pattern is then repeated for the other device wall. The opposing side of the device includes a non-woven fabric ring 58, film ring 57, a membrane layer wherein two layers of non-woven fabric are laminated, such as heat laminated, to the cell-excluding membrane (56) the non-woven fabric layer faces out toward the host while the cell-excluding membrane layer faces in toward the chamber or the implanted cells. As noted above, there is a film ring (55) at the periphery or weld. That is, the two sides or walls of the chamber are mirror images of each other, with the port (85) for loading cells in between forming a lumen (86) where the therapeutic agent resides. See FIG. 1A. In this embodiment, the mesh layer is not included. In some embodiments rather than a non-woven fabric ring, the entire surface of the delivery device is covered in non-woven fabric (compare FIGS. 1A and 1B, 51 and 59).

Figure 1B:
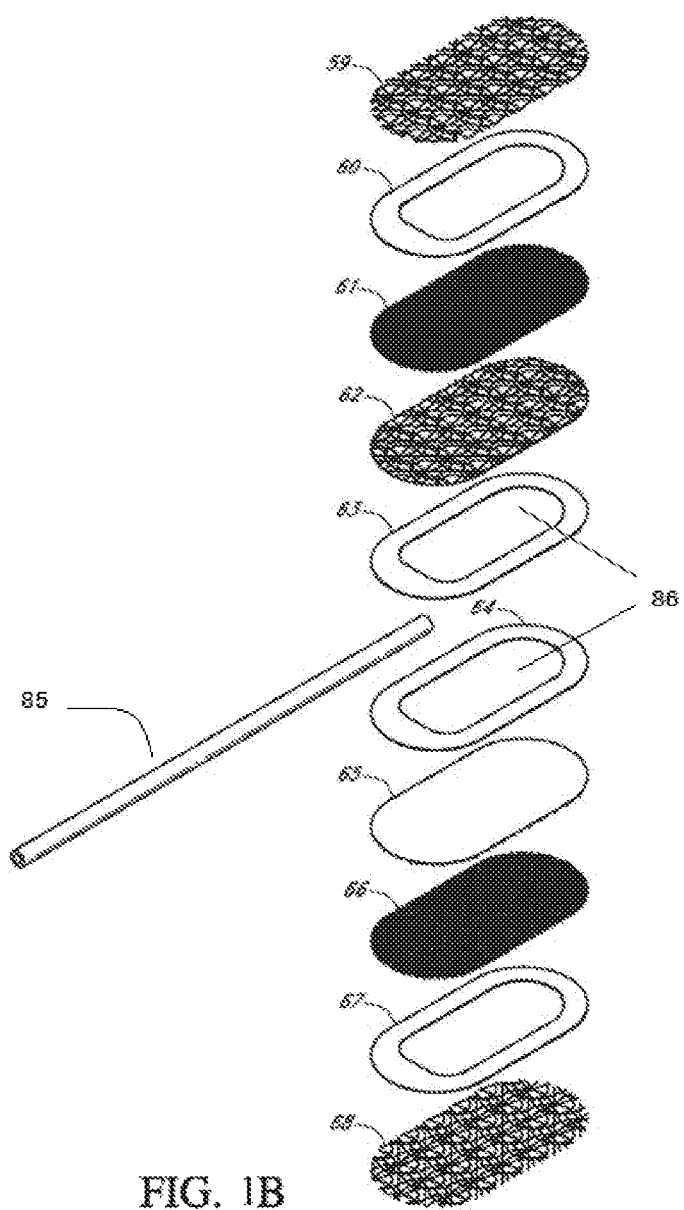

FIG. 1B is one embodiment showing an delivery device (EN20B2) with a non-woven fabric layer (59), a film ring (60), a mesh layer (61), a cell-excluding membrane layer wherein a non-woven fabric layer is laminated, such as heat laminated, to the membrane (62), and a film rings (63) at the periphery of the weld. The two sides or walls of the chamber are mirror images of each other, with the port (85) for loading cells in between forming a lumen (86) where the therapeutic agent resides. Thus, the opposing side of the device includes a non-woven fabric layer (68), a film ring (67), a mesh layer (66), a cell-excluding membrane layer wherein a non-woven fabric layer is laminated, such as heat laminated, to the membrane (65), and a film ring (64) at the periphery of the weld. Similar to FIG. 1A, the two sides of the chamber are mirror images of each other.

Figure 1C:
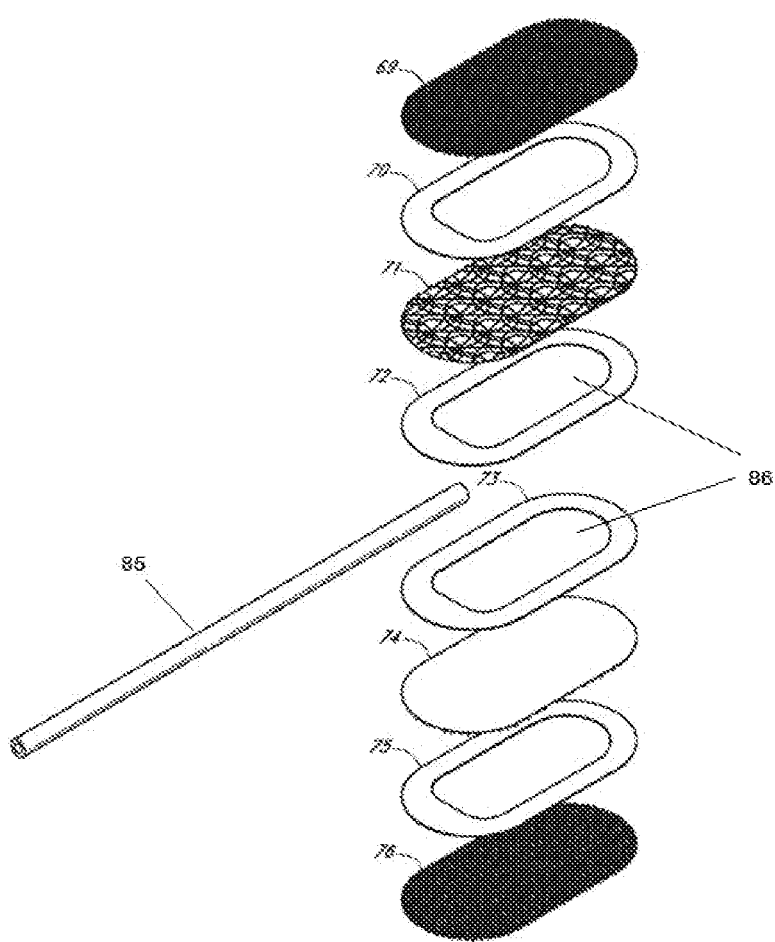

FIG. 1C is one embodiment showing a delivery device (EN20B3) with a mesh layer (69) a film ring (70), a cell-excluding membrane layer wherein a non-woven fabric layer is laminated, such as heat laminated, to the membrane (71), a film ring (72) at the periphery of the weld. Thus, another mesh layer (76), film ring (75), cell-exluding membrane layer wherein a non-woven fabric is laminated, such as heat laminated, to the membrane (74), and a film ring (73) is shown. The two sides or walls of the chamber are mirror images of each other, with the port (85) for loading cells in between forming a lumen (86) where the therapeutic agent resides. Similar to FIGS. 1A-B, the two sides of the chamber are mirror images of each other.

Figure 1D:
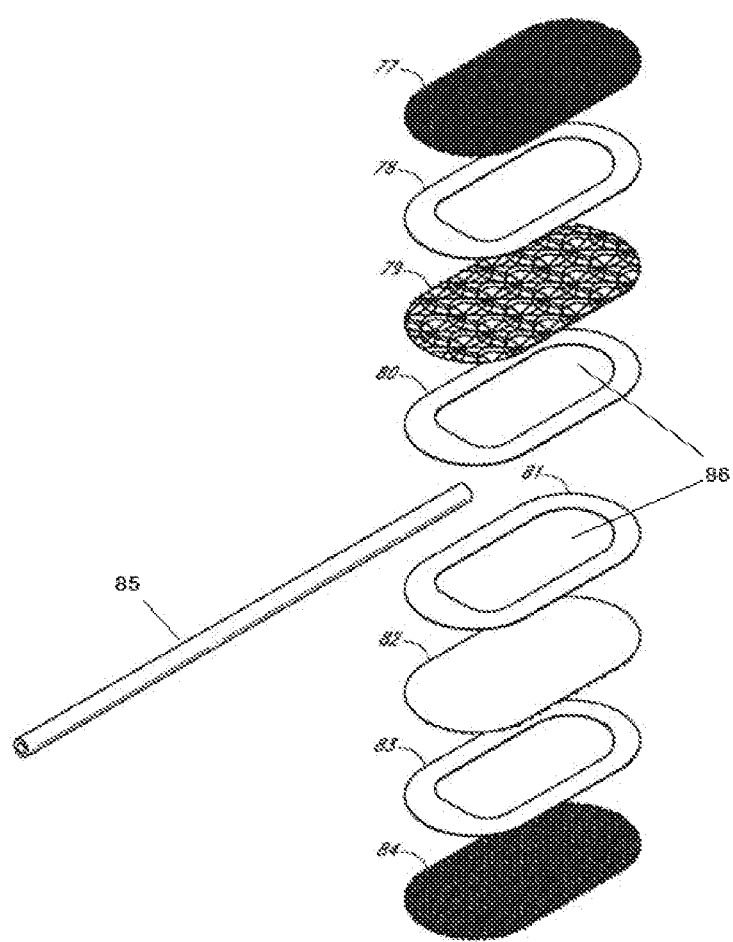

FIG. 1D is one embodiment showing a delivery device (EN20B4) which has the same configuration as the EN20B3 but the non-woven fabric layers (79 and 82) have a different density than the density of the non-woven fabric layers in EN20B3. The mesh layers (71 and 84), film rings (78, 80, 81 and 83) are similar to the respective elements shown in FIG. 1C.

In one embodiment, the non-woven fabric and cell-excluding membrane may be laminated, such as using heat lamination or heat press (e.g. an ARB Arbor Press from Plastic Assembly Systems). The press is heated to between about 305-320 Farenheit. A pressure of between 0-6 PSI is applied to the non-woven fabric and membrane at a rate of 3 feet/minute or 10 feet/minute. However, the non-woven fabric and cell-excluding membrane need not be laminated.

In one embodiment, the non-woven fabric layer faces out toward the host while the cell-excluding membrane layer faces in toward the chamber or implanted cells, but a skilled artisan can envision different configurations using the present disclosure, for example, that the non-woven fabric layer can face in toward the chamber or implanted cells while the cell-excluding membrane layer faces out toward the host. In some embodiments, the non-woven polyester fabric is on the outside of the cell-excluding membrane and is laminated to the membrane.

In some embodiments, the cell-excluding membrane and/or non-woven fabric are laminated together and then perforated. In some embodiments, the cell-excluding membrane is first perforated and then laminated to a non-woven fabric. In some embodiments, just the non-woven fabric is perforated and then laminated to the cell-excluding membrane. When the cell-excluding membrane is perforated the mammalian host is either immunocompromised or treated with immunosuppressant drugs.

The non-woven fabric used in the cell delivery device as shown in FIGS. 1A-D as being substantially flat but it can be further manipulated to provide thickness. For example, the non-woven fabric can be pleated, contoured or embossed. Additionally, fabrics with pile, a looped fabric, tufting as in carpet manufacturing may be utilized to produce a fabric with pile and other three-dimensional structures. See e.g., U.S. Pat. No. 7,754,937 which is herein incorporated in its entirety by reference.

The device contemplated herein can have many different configurations and different capacities for holding the therapeutic agent. ENCAPTRA EN20 or EN20 or EN20 device or small delivery device refers to a device with a functional volume of about 20 µl and can contain about 2,500 to 3,500 IEQ of beta cell mass or greater than 80,000 IEQ per kg in a mouse. ENCAPTRA EN250 or EN250 or EN250 device or large delivery device has a functional volume of about 250 µL and is about 12.5 times (12.5×) greater than the EN20 device and can contain up to about −30,000 to 45,000 IEQ per kg in a mouse. ENCAPTRA EN100 or EN100 or EN100 device has a functional volume of about 100 µL is about 6.5 times (6.5×) greater than the EN20 device and can contain up to about 16,250 to 22,750 IEQ per kg in a mouse. EN-large capacity or EN-LC device is about 48.4 times (48.4×) greater than the EN20. An EN-LC device containing 4 cell chambers, can contain up to about 121,000 to 169,400 IEQ, and so on. Hence, in order for the therapeutic effective dose to be delivered to a patient, it is anticipated that encapsulation using at least about 4, about 5, about 6, about 7, about 8 EN250 devices or about 2 EN-LC devices will be required to deliver sufficient PEC quantities.

In addition to increasing the size of the device to increase the dosing capacity, perforating the device increases the dosing capacity. A perforated EN20 device has a dosing capacity (meaning the beta cell mass achieved at maturation) about 5× that of an unperforated EN20 device. Stated another way dosing of a perforated device is about ⅕ of an intact device.

Perforated Cell Delivery Devices

To promote vascularization shortly after implant, cells are implanted in a perforated cell delivery device which provides direct cell-to-cell contact between host vasculature and the encapsulated cells. In some embodiments, not all the layers of the device are perforated. For example, a perforated cell delivery device is provided with perforations in just one layer, for example, the cell-excluding membrane; or, in just the cell-excluding membrane and the non-woven fabric layer. This helps retain the implanted cells/tissue while at the same time allowing exchanges with the host such as ingress of the vasculature, macrophages and the like.

By laser drilling the perforations, the perforation size, number and location can be selected. The perforations are of sufficient size to allow host vascular tissue (such as capillaries) and stromal cells that support pancreatic cell types to enter the device lumen. In one embodiment, the perforations are sized such that host macrophages and other phagocytes can also enter the device and remove necrotic debris from the perforated device lumen. In one embodiment, the perforations are also sized to allow therapeutic agents such as insulin produced by the graft to exit the cell delivery device. Perforations allowing for vascular structures to grow into the device lumen help anchor the device to the host and inhibit movement of the device. In one embodiment, the perforations are also sized based on cell aggregate diameter to maximize cell retention.

In some embodiments, the device includes a cell housing made of a biocompatible material adapted to be implanted in a host, and to substantially contain therapeutic agents which can be immunologically compatible or incompatible with the host, the chamber having a wall comprising cell-excluding membrane and optionally a mesh layer or layers and film weld, said wall having holes traversing just the cell-excluding membrane; where the holes have an inner diameter at the narrowest point large enough to permit a host capillary to traverse the thickness of the wall, and where said holes are numerous enough to permit said host capillary to support the viability of the therapeutic agents which may be contained therein.

In one embodiment, a perforated delivery device is provided wherein one or more layers of the delivery device is perforated. In one embodiment, a perforated delivery device is provided wherein one or more layers of the delivery device is not perforated. In one embodiment, only the cell-excluding membrane is perforated. In one embodiment, a cell delivery device comprises holes which do not traverse each wall of the device is provided. In one embodiment, perforations in the cell delivery device consist of holes which do not traverse each wall of the device but host vasculature growth into the inner lumen of the cell delivery device still occurs. In one embodiment, a cell delivery device that does not comprise a non-woven fabric is disclosed. In one embodiment, a cell delivery device that does not comprise a non-woven fabric but the cell-exclduing memebrane is perforated is disclosed. In such embodiments, the hole diameter in the cell-excluding membrane is used to retain the cells, i.e., the holes in the device are smaller than the cell aggregates contained therein.

In one embodiment, the cells in the perforated delivery device consists of PDX1/NKX6.1 co-positive pancreatic progenitor cells. In one embodiment, the cells in the perforated delivery devices consists of immature beta cells expressing insulin (INS) and NKX6.1 or immature beta cells expressing INS, NKX6.1 and MAFB. In one embodiment, the cells in the perforated delivery device consists of mature beta cells expressing INS and MAFA or INS, NKX6.1 and MAFA. In one embodiment, the cells in the perforated delivery device consists of pancreatic endocrine cells. In one embodiment, the cells in the perforated delivery device consists of pancreatic insulin secreting cells. In one embodiment, cells in the perforated delivery devices consist of pancreatic beta or insulin cells capable of secreting insulin in response to blood glucose levels.

Perforated Devices Surrounded By A Non-Woven Fabric

In these embodiments, the non-woven fabric is on the outside of the cell delivery device. Rather than affecting implanted cells, the non-woven fabric enhances host vascularization surrounding the cell housing.

In one embodiment, a cell delivery device comprising a non-woven fabric is disclosed. In one embodiment, a cell delivery device comprising a non-woven polyester fabric (NWPF) is disclosed. Polypropylene, polyethylene, nylon, polyurethane, polyamide are some examples of a non-woven polyester fabric that can be used. In one embodiment, the cell-excluding membrane is surrounded (or coated) with a non-woven fabric, i.e., the non-woven fabric is external to the cell-excluding membrane. Stated another way, the non-woven fabric faces the host not the implanted cells. In one embodiment, the non-woven fabric forms a jacket around the cell excluding membrane. In one embodiment, only the cell-excluding membrane is perforated, the other layers of the device including the non-woven fabric are not perofrated. In one embodiment, just the cell-excluding membrane and the non-woven fabric are perforated and the other layers of the device are not perforated.

In one embodiment, the holes/perforations are smaller than cell aggregates contained in the device, such as the hPSC-derived aggregates, e.g. definitive endoderm lineage cell aggregates, contained therein. In one embodiment, the holes are smaller than the PDX1-positive pancreatic endoderm cell aggregates contained therein. In one embodiment, the holes are smaller than the pancreatic progenitor cell aggregates contained therein. In one embodiment, the holes are smaller than the pancreatic endocrine cell aggregates contained therein. In one embodiment, the holes are smaller than the mature beta cell aggregates contained therein.

In one embodiment, the hole diameter is small enough to retain the cells but large enough to ensure that the desired therapeutic effect is achieved. For example, in the case of a diabetic patient the hole diameter is determined by the ability of the implanted cells to mature and/or produce insulin in response to blood glucose levels.

In one embodiment, a perforated cell delivery device is implanted into a rat or human. In one embodiment, a perforated cell delivery device implanted into a rat or human contains perforations in just the cell-excluding membrane and the non-woven polyester fabric (the other layers of the device are not perforated) and wherein the holes are separated by about 2 mm (measuring center to center from the holes) or more and wherein the hole diameter is less than about 100 microns is provided. In one embodiment, a perforated cell delivery device implanted into a rat or human contains perforations in just the cell-excluding membrane and the non-woven polyester fabric (the other layers of the device are not perforated) and wherein the holes are separated by about 2 mm or more. In one embodiment, a perforated cell delivery device implanted into a rat or human contains perforations in just the cell-excluding membrane and the non-woven polyester fabric (the other layers of the device are not perforated) and wherein the hole diameter is less than about 100 microns is provided.

In one embodiment, a perforated cell delivery device implanted into a rat or human contains perforations in just the cell-excluding membrane (the other layers of the device are not perforated) and wherein the holes are separated by about 2 mm or more and wherein the hole diameter is less than about 100 microns is provided.

In one embodiment, a cell delivery device comprises a perforated cell-excluding membrane and PDX1-positive pancreatic endoderm cells, which can be implanted into a human patient wherein the PDX1-positive pancreatic endoderm cells mature in vivo to insulin-producing cells. In one embodiment, a cell delivery device comprises just a perforated cell-excluding membrane and perforated NWF layer and PDX1-positive pancreatic endoderm cells, wherein the cell delivery device can be implanted into a human patient wherein the PDX1-positive pancreatic endoderm cells mature in vivo to insulin-producing cells.

Laminated Devices

In one embodiment, the cell-excluding membrane is laminated to the non-woven fabric. In one embodiment, the cell-excluding membrane is laminated to the NWF. When the cell-excluding membrane is laminated to a non-woven fabric the cell-excluding membrane remains flat. Without lamination, the cell-excluding membrane can deform out of plane which creates dams which may lead to an uneven distribution of cells. An uneven distribution of cells can lead to necrotic regions, cell death and otherwise may reduce efficacy. Control of cell distribution within the chamber or lumen of the cell delivery device is also referred to as the spatial location of cells within the cell delivery device. In one embodiment, a method for controlling the distribution of cells (cell location) within a cell delivery device is provided comprising laminating the cell-excluding membrane to a non-woven fabric. In one embodiment, a method for controlling the distribution of cells (cell location) within a cell delivery device is provided comprising laminating the cell-excluding membrane to a NWF.

By achieving an even distribution of cells inside the lumen of the cell delivery device fewer cells need to be implanted. The use of fewer cells results in less cellular debris. Another benefit is the enhanced diffusion of nutrients to the cells because the cells are evenly distributed and in closer contact with the membrane. Enhanced diffusion of nutrients to the cells leads to improved cell survival.

Complete filling of the lumen can be achieved consistently with devices incorporating laminated membranes resulting in maximizing therapeutic efficacy of the implanted cells. Longer and larger lumens can be filled with devices incorporating laminated membranes.

Perforated and Laminated Devices

Perforations are also referred to as holes, pores, openings, punctures, apertures or channels.

It is to be understood that the foregoing devices are non-limiting disclosures and that other devices in keeping with the embodiments described herein are embodied by this disclosure. This disclosure envisions combinations of the above-described devices. For example, in one embodiment, a cell-excluding membrane, and non-woven fabric are laminated together and then perforated. In one embodiment, a perforated cell-excluding membrane and a non-perforated NWF are laminated together.

The potential therapeutic value of a perforated device loaded with therapeutic cells has significant value for the Type 1 Diabetes (T1D) population where the side-effects of chronic immunosuppression are acceptable or immunosuppression is already needed due to prior organ transplantation (e.g., kidney transplant). Importantly, therapeutic cells which are derived from pluripotent stem cells overcome the limitations associated with use of deceased organ donors, which are principally: (1) severely limited supply of suitable cadaveric islets relative to the demand, and (2) patient risks associated with donated organs (e.g., donor-derived pathogens with limited ability to screen donated tissues prior to transplantation). Moreover, the delivery device and subcutaneous implantation route of administration provide several advantages over current clinical islet transplantation, including the ability to non-invasively monitor and image the graft site, surgical ease of implant and explant/biopsy, and elimination of portal thrombotic events. Indeed, the islet transplantation field has long sought alternatives to the intraportal transplantation site. Cantarelli et al., Alternative transplantation sites for pancreatic islet grafts *Curr Diab Rep*. 2011 October; 11(5):364-74.

To determine desirable device perforation geometries, the diameter, quantity, and distribution of holes were characterized. FIGS. 2A-D are each an embodiment depicting a device with a certain density of holes. While the holes shown in this figure are uniform in shape and size, studies showed that: i) the holes need not be uniform in size or shape and; ii) the holes on both sides of the device do not need to line up (be in an ordered array) when the device is assembled; iii) the number or density of holes in each device can be a de minimus number and still promote direct host-implant cell-to-cell contact and vascularization; iv) and the diameter of the hole will depend on the cell or tissue encapsulated therein, e.g. size of the cell cluster or aggregate, but that encapsulated cells do not necessarily leak out of the devices through the perforations, rather there are more host-derived cells found in the interior of the device as compared to transplanted cells on the exterior of the device; and v) the holes in the cell-excluding membrane and non-woven fabric do not need to line up when the device is assembled and may form irregular pathways from the exterior to the interior of the device chamber. Moreover, while the device is shown as ovoid shaped, the device can be any shape such as a circle, rectangle, square, triangle etc.

In one embodiment, the perforations are of circular shape or oval shape or elliptical shape. It should be noted that the perforations can have other shapes such as rectangular or hexagonal or polygonal, or slits. In one embodiment, the perforations have a uniform shape. In one embodiment, the perforations do not have a uniform shape. In one embodiment, the perforations are uniformly distributed on the cell excluding membrane. In one embodiment, the perforations are variably spaced on the cell excluding membrane, for example, they may be clustered at the center of the device or at the ends of the device. In one embodiment, the plurality of perforations is spaced in a series of rows and columns forming a grid arrangement or concentric circles or any other geometric configuration or combinations of such configurations. In one embodiment, the plurality of perforations is randomly distributed. In one embodiment, perforations are not on each cell-excluding membrane but only on one side of the device.

In one embodiment, a cell delivery device comprises layers wherein only the cell-excluding membrane is perforated with holes. In one embodiment, a cell delivery device comprises a film ring, a mesh and cell-excluding membrane wherein only the cell-excluding membrane is perforated with holes. In one embodiment, a cell delivery device comprises a film ring, a mesh, non-woven fabric and cell-excluding membrane wherein only the cell-excluding membrane and non-woven fabric layer are perforated with holes. In one embodiment, a cell delivery device comprises non-woven fabric and cell-excluding layers wherein only the cell-excluding membrane and non-woven fabric layer are perforated with holes. In one embodiment, a cell delivery device comprises a non-woven fabric external to the cell-excluding membrane wherein only the cell-excluding membrane and non-woven fabric layer are perforated with holes. In one embodiment, a cell delivery device comprises non-woven fabric and cell-excluding layers laminated to each other wherein only the cell-excluding membrane and non-woven fabric layer are perforated with holes. In one embodiment, a cell delivery device comprises a non-woven fabric external to the cell-excluding layer and laminated to the cell-excluding membrane wherein only the cell-excluding membrane and non-woven fabric layer are perforated with holes.

In one embodiment, a cell delivery device comprises layers wherein only the cell-excluding membrane and non-woven fabric layer are perforated with holes wherein the holes are made with a laser.

Diameter of the Perforation

The use of perforated cell delivery devices has certain disadvantages such as cellular escape and lesser so, tumorigenicity. The aperture of the perforations should therefore enable the cell-excluding membrane to retain the encapsulated elements, while at the same time allowing exchanges with the host such as ingress of vasculature, macrophages and other phagocytes that can remove necrotic debris from the perforated device lumen and stromal cells that support pancreatic cell types. In one embodiment, the perforations are less than about 100 µM in diameter to allow capillary ingrowth. Applicants have previously disclosed that pancreatic progenitor cell aggregates average approximately 180 µm in diameter with quartile range approximately 100-200 µm (Schulz et al. (2012) supra), therefore hole diameters of about 100 µm or less provide substantial retention of the cell product, while still achieving the other benefits described above and, thus, facilitate both delivery and retrieval of the cells as well as allow capillary ingrowth. Hence, the cells are exposed to the host tissue, e.g., host blood vessels, but due to their larger size, the risk of cell escape is low to de minimus. In one embodiment, the holes have an inner diameter large enough to allow the ingrowth and egress of host capillaries and large enough to allow the hormone produced by the therapeutic agent to exit the device lumen/chamber.

Figure 2A:
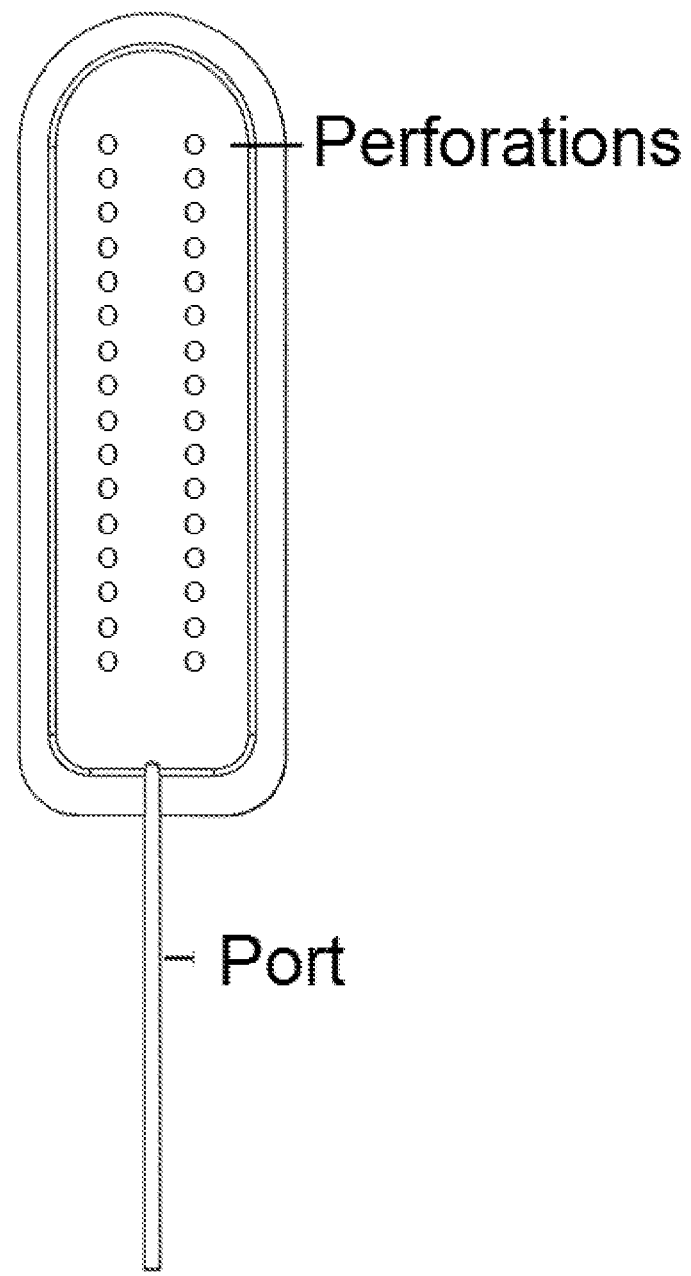
FIGS. 2A-2D are each an embodiment of a perforated cell delivery device.
Figure 2B:
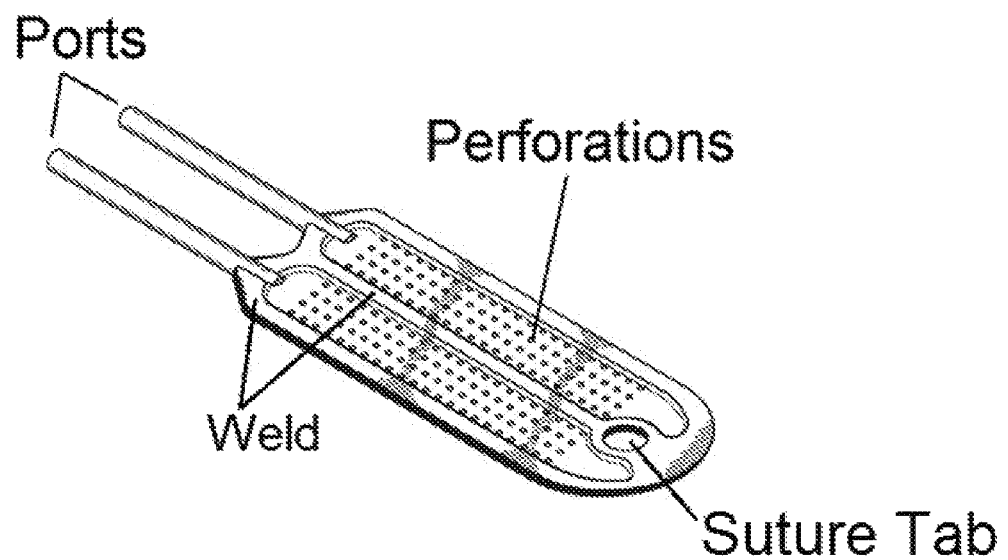
Figure 2C:
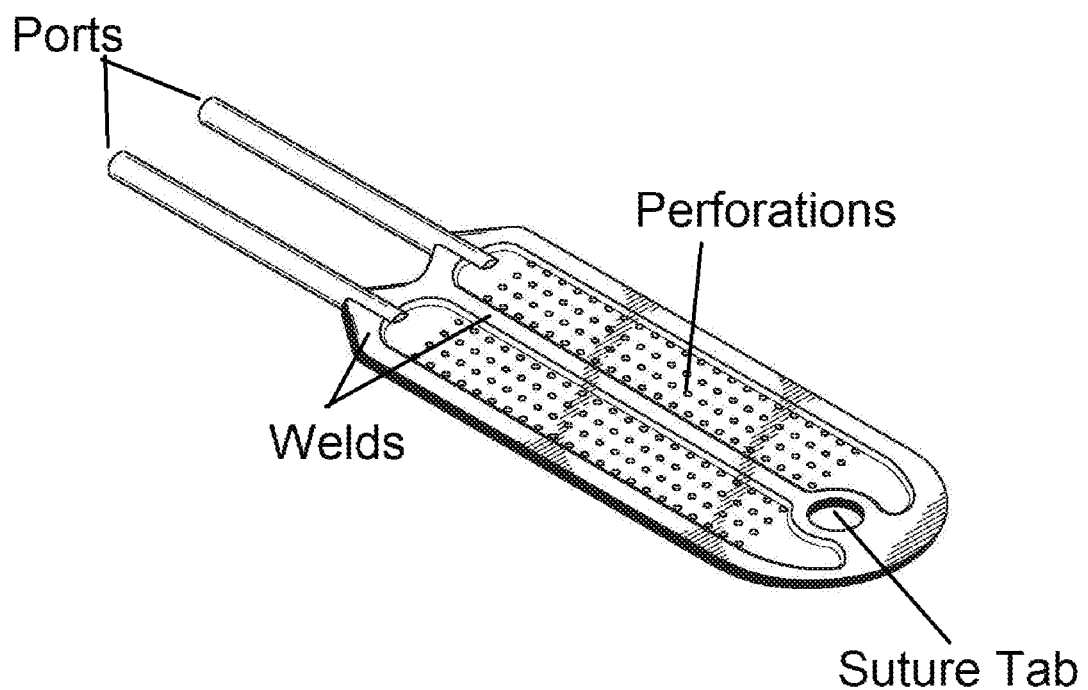
Figure 2D:
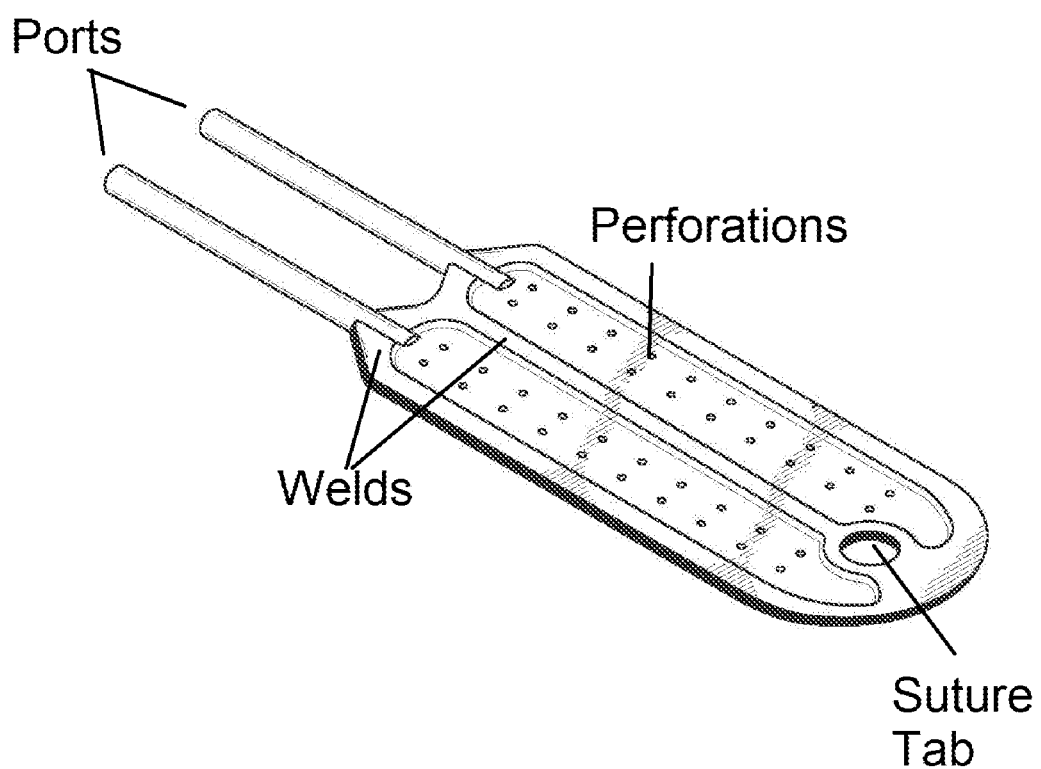

The hole size (diameter) may be varied depending on the cell function. For example, if complete cell containment is not necessary, then there is less restriction with regard to hole diameter and density. The holes in a particular device may have the same diameter, or may have different diameters in different parts of the device. For example, if the majority of the encapsulated cells, cell aggregates, organoids, clusters, clumps, and tissues tend to be located approximately in the center of the device, then more holes may be necessary for cell survival in that region of the device as compared to the proximal and distal ends of the device which may have fewer and/or smaller holes. As such, there is a lot of flexibility in the size, density ad distribution of perforations, so long as host-implant cell-to-cell vascularization is established shortly after transplantation. Again FIGS. 2A and 2B show embodiments of a perforated device. FIG. 2B shows a double lumen and a double port which reduces areas of cell pooling.

In other embodiments, pancreatic progenitor cell aggregates which are larger in size as compared to the average hole diameter of the perforation in a device. In one embodiment, the cell delivery device is perforated with holes less than about 300 microns, less than about 200 microns, less than about 150 microns, less than about 100 microns, or less than about 75 microns, or less than about 60 microns, or less than about 50 microns in diameter. In one embodiment, the cell delivery device is perforated with holes between about 300-50 microns or about 200-50 microns, or about 200-75 microns or about 70-80 µm in diameter. In one embodiment, the hole diameter is greater than about 200 microns. In one embodiment, the hole diameter is about 200-400 microns.

In one embodiment, the perforations have a diameter between about 40 and 150 µm. In one embodiment, the perforations have a uniform diameter. In one embodiment, the perforations do not have a uniform diameter.

Density of Perforations

In one embodiment, less than 0.4% of the device's surface area is perforated and the holes are separated by about 2 mm (measuring center to center of the holes); however, they can be separated by less or more than 2 mm and still promote host-implant cell-to-cell vascularization. In some embodiments, less than about 5.0%, less than about 4.0%, less than about 3.0%, less than about 2.0%, less than about 1.0%, less than about 0.8%, less than about 0.3%, less than about 0.2%, less than about 0.1%, less than about 0.05% of the device's surface area is perforated. In some embodiments about 5.0-0.5%, about 5.0-3.5%, about 4.0-2.0% of the device's surface area is perforated.

In one embodiment perforations are avoided by replacing the cell-excluding membrane with a highly permeable membrane. For example, a membrane that consists of 80-120 micron pores in the membrane, such pores occurring at a density much like that described herein.

Example 1 shows that the perforations can be relatively few and still provide the desired benefit of direct host vascularization while enhancing cell survival. Glucose-stimulated insulin secretion (GSIS) testing (as described in Example 1) at 12 and 34 weeks post-implant indicates that holes approximately 100 μm in diameter and spaced approximately 1, 1.5 or 2 mm apart (measuring center to center of the holes) from each other produce functional grafts in athymic nude rats. Indeed, even the lowest density of holes, i.e., 2 mm spacing, showed direct vascularization and robust c-peptide levels. From a clinical safety perspective, fewer holes reduces the risk, if any, of cells escaping from the cell delivery device, hence the lowest density of holes (2 mm spacing) for the perforated device is preferred.

In one embodiment, a cell delivery device comprises a perforated cell-excluding membrane with holes separated by about 0.5 mm, 1.0 mm, 1.5 mm, 2 mm, 4 mm, 8 mm or more (measuring center to center of the holes). In one embodiment, a cell delivery device comprises a perforated cell-excluding membrane and perforated NWF layer with holes separated by about 0.5 mm, 1.0 mm, 1.5 mm, 2 mm, 4 mm, 8 mm or more. In one embodiment, a cell delivery device comprises a perforated cell-excluding membrane laminated to a perforated NWF layer with holes separated by about 0.5 mm, 1.0 mm, 1.5 mm, 2 mm, 4 mm, 8 mm or more. In one embodiment, a cell delivery device consisting of holes or perforations, wherein the holes are separated by about 0.5 mm-4 mm, or by about 0.5 mm-2 mm, or by about 1.0 mm-2 mm is provided.

The number/density of holes can be from 5-200 or from 20-100 holes per device and will depend in part of the size of the device (lumen surface area). Indeed, the number/density of holes can be from 20 to 50 to 100 holes per device lumen. The number/density of holes can be from 5-200 or from 20-100 holes per device lumen. A skilled artisan can determine the number/density of holes to achieve the desired effect. In the case of a diabetic patient, the number/density of holes is determined by the ability of the implanted cells to mature and/or produce insulin in response to blood glucose levels.

In one embodiment, a cell delivery device comprising holes or perforations, wherein the holes are separated by about 0.5 mm, 1.0 mm, 1.5 mm, 2 mm or more is provided and wherein the hole diameter is less than about 200 microns, less than about 150 microns, less than about 100 microns, or less than about 75 microns. In one embodiment, a cell delivery device comprising perforations, wherein the holes are separated by about 2 mm or more and wherein the hole diameter is less than about 200 microns is provided. In one embodiment, a cell delivery device comprising holes or perforations, wherein the holes are separated by about 2 mm or more and wherein the hole diameter is less than about 100 microns (measuring center to center of the holes) is provided.

Manufacturer of Perforated Cell Delivery Devices

Manufacturing methods known in the art can be used to produce the disclosed perforated devices. Historically, devices were assembled, loaded with cells, and then a needle was used to manually add perforations to an intact device. As such, all layers of the device were perforated. See U.S. application Ser. No. 12/618,659 and PCT Application No. WO/1993/002635. Additionally, because the cells were inside the device when the perforations were made some portion of encapsulated cells are in the path of the needle upon perforation and the needle could damage some of the encapsulated cells. This method can also lead to inadvertent contamination (cells leaving the device) as the needle is inserted to make the hole and then removed.

Embodiments herein describe using a laser that provides control over hole size and distribution and does not perforate each layer of the device; and does not perforate the device after the cells are loaded. In this way, no cells are injured or destroyed by forming the perforations, potential contamination is reduced and just the cell-excluding membrane (or just the cell-excluding membrane and non-woven fabric layer) is perforated so that the other layers can help retain the encapsulated cells in the delivery device upon implant.

Perforated cell delivery devices can be constructed in multiple size configurations such as for preclinical rodent models (with nominal 20 μL capacity) and larger devices for clinical studies (EN250). Perforated and unperforated cell delivery devices share identical materials, manufacturing techniques and thickness.

By using lasers instead of a needle, disclosed is the manufacture of perforated cell delivery devices wherein only the cell-excluding membrane is perforated. In some embodiments, the non-woven fabric is laminated to the cell-excluding membrane and only these two layers are perforated. In one embodiment, the manufacture of holes in the device layers is automated.

In one embodiment, the perforations are of circular shape or oval shape or elliptical shape. It should be noted that the perforations can have other shapes such as rectangular or hexagonal or polygonal, or slits. In one embodiment, the perforations have a uniform shape. In one embodiment, the perforations do not have a uniform shape. In one embodiment, the perforations are uniformly distributed on the cell excluding membrane. In one embodiment, the perforations are variably spaced on the cell excluding membrane, for example, they may be clustered at the center of the device or at the ends of the device. In one embodiment, the plurality of perforations is spaced in a series of rows and columns forming a grid arrangement or concentric circles or any other geometric configuration or combinations of such configurations. In one embodiment, the plurality of perforations is randomly distributed. In one embodiment, perforations are not on each cell-excluding membrane but only on one side of the device.

In one embodiment, there are a plurality of different cell populations in the device. In one embodiment, there are a plurality of chambers in the device and each chamber is separated by a cell-free zone or island and each chamber is perforated. In one embodiment, there are a plurality of chambers in the device and each chamber is separated by a cell free zone and not all chambers are perforated. In one embodiment, pancreatic progenitors are encapsulated in one chamber and a different therapeutic agent is encapsulated in another chamber. In this instance, only the chamber comprising the pancreatic progenitors will be perforated.

Improved Dosing Profile

One advantage of using perforated devices for delivering pancreatic endoderm lineage cells is the proliferative capacity of the cells increases. The holes allow cell-to-cell contact with the host vasculature which improves their survival. The holes also allow increased expansion of the device chamber, thus, there is room for more cells within perforated devices. This increase in cell proliferative capacity results in an increase in cell mass, and an increase in cell mass correlates to an increase cell volume. Applicant's have shown that when an approximate cell volume is loaded into the same size device (e.g. EN20, EN100, EN250 etc.), the final cell volume (mature cells approximately 12-16 weeks post implant) is significantly higher in the perforated device as compared to the intact or non-perforated device. In fact, the final (mature) cell volume is about 5-6× more in the perforated device as compared to the non-perforated or intact devices. This significantly improves the dosing capacity of the otherwise same size cell delivery devices.

In islet transplant procedures, islet number or volume is often expressed as islet equivalents, or IEQ. One IEQ is considered equivalent to a pancreatic islet with a diameter of 150 μm. It is assumed that healthy people have about 1 Million IEQs and patients diagnosed with T1D have about 80% islet cell loss. A thereapuetic need not restore complete islet mass/function. It has been shown that restoring about 20% of islet cell mass/function, i.e., about 200,000 IEQs, is a functional cure for T1D patients. Gillard et al Minimal functional β-cell mass in intraportal implants that reduces glycemic variability in type 1 diabetic recipients Diabetes Care 2013 (11)3483-8 shows recipients with functioning β-cell implants exhibited an average functional β-cell mass corresponding to 18% of that in normal control subjects (interquartile range 10-33%).

Applicants sought to calculate the IEQ based on the c-peptide released by implanted mature PEC grafts as previously described Kroon et al. (2008), supra. Applicants showed there is a linear scale corrolating the c-peptide produced in the devices to the relative IEQ number. See FIG. 3. To generate this graph, Applicants purchased cadaveric islets aliquoted in specific quantities. Six different islet preparations were ground up and total c-peptide was measured from each sample. Measurements of c-peptide for each islet sample were graphed and the relationship of the levels of c-peptide versus the amount of human islet equivalents was shown to have a linear relationship. See FIG. 3. The equation below defines the linear relationship between c-peptide levels (picomoles) and human islet numbers (IEQ):

$$c\text{-peptide}=0.3889x+245.53$$

This equation has a correlation of determination $R^2$ of 0.9852. The $R^2$ coefficient of determination is a statistical measure of how well the regression line approximates the real data points. An $R^2$ of 1 indicates that the regression line perfectly fits the data. Thus, the correlation between c-peptide and IEQ as represented by the equation has a strong or high confidence level.

In one embodiment, the number of IEQs can be extrapolated or deduced by the linear relationship of the c-peptide levels to islet IEQs; and the number of IEQs is a relative measure of the cell dose achieved in any one perforated or non-perforated device containing the therapeutic cells. Thus, for example, 2000 picomoles of c-peptide is about 4500 IEQs or human islets as follows:

$$2000=0.3889x+245.53 \rightarrow (2000-245.53)/0.3889=x \rightarrow x=4511.36 \text{ IEQs}$$

In one embodiment, a perforated cell delivery device improves the dosing capacity as compared to wholly (non-perforated) cell delivery devices by at least 2-fold, by at least 3-fold, by at least 4-fold, by at least 5-fold or more. For example, a perforated EN20 device or small delivery device has a nominal fill volume of about 20 μl and can contain about 7,000 to 47,000 IEQ of beta cell mass (mean of about 23,000) or greater than 250,000 IEQ per kg in a rat. A larger delivery device with a nominal fill volume of 300 μl can contain up to 700,000 IEQ of beta cell mass. Hence, in order for the therapeutic effective dose to be delivered to a patient, it is anticipated that just one or two large perforated devices will be required to deliver sufficient PEC quantities.

In one embodiment, c-peptide production in a mammal after implantation with a perforated cell delivery device does not plateau until after about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks.

In one embodiment, c-peptide production in a mammal after implantation with a perforated cell delivery device plateaus at about 30 weeks after implantation, about 31 weeks after implantation, about 32 weeks after implantation, about 33 weeks after implantation, about 34 weeks after implantation, about 35 weeks after implantation, about 36 weeks after implantation, about 37 weeks after implantation, about 38 weeks after implantation, about 39 weeks after implantation, about 40 weeks after implantation. In one embodiment, c-peptide production in a mammal after implantation with a perforated cell delivery device plateaus at about 30-40 weeks after implantation. In one embodiment, c-peptide production in a mammal after implantation with a perforated cell delivery device plateaus at about 35-45 weeks after implantation, at about 30-45 weeks after implantation.

It is hypothesized that perforated cell delivery devices may provide a type of protective niche within the device lumen to shield implanted cells from what would otherwise be a harsh subcutaneous host environment immediately post-implantation. Indeed, when Applicant compared perforated devices versus no cell encapsulation at all (i.e. no device/"naked cells" transplanted under the epididymal fat pad), there was improved cell function in the perforated devices as compared to the naked cells (data not shown). Thus, more direct host-implant cell-to-cell contact (e.g. direct vascularization) of the cells alone was not the solution to improved cell function in vivo otherwise it would have been expected that the naked cells would have improved function over cells in a perforated device. See Example 1 of Applicant's U.S. Ser. No. 12/618,659, supra.

The delivery device may be used for tissue or cell replacement in the correction of disease states. Allograft implants of cellular organelles or free cells to correct a disease state are currently performed most commonly by infusion into the portal circulation to allow the cells to lodge in the liver. The instant invention allows the use of an alternate implant site that can be easily accessed and the delivery device with its contents may be removed if necessary. The delivery device allows the host to provide adequate nutritional support for the implanted tissue to correct a disease state. Accordingly, the delivery device may be used for allograft transplant of human tissue.

The delivery device may also be used to implant a patient's own cells which have been genetically altered so that they produce a therapeutic product. Once cells have been transformed to express a gene and secrete a therapeutic product, a removable container for those cells is desirable. This delivery device may also be used to construct a hybrid bioartificial organ. The delivery device allows the host to supply the bioartificial organ with an intimate vasculature so that nutrients are delivered to the organ, metabolic wastes are removed, and the therapeutic product made by the organ is delivered to the host.

Additional development work on biological immunoprotective strategies could remove the need for chronic immunosuppression in the future. See Rong, An effective approach to prevent immune rejection of human ESC-derived allografts *Cell Stem Cell* 2014 14(1): 121-130 which is herein incorporated in its entirety by reference.

Unless otherwise stated, non-perforated devices or intact devices mean a device without perforations (holes).

Combination Product

The embodiments described herein disclose a combination product, which refers to a device loaded with cells or therapeutic agent, i.e. each alone may be a candidate medical device or cell product, but used together they make a combination product. In one embodiment, the combination product refers to a perforated device loaded with cells. This is referred to as a "perforated combination product." The device (perforated or not) can be any macro cell delivery device described herein including but not limited to the EN20, EN100, EN250, or the EN-large capacity. The combination product may specify the device size for example VC-01-20 means the EN20 loaded with cells. The cells loaded into the device (perforated or not) may be any cells discussed above including but not limited to definitive endoderm, PDX1-positive endoderm, PDX1-positive foregut endoderm, pancreatic endoderm, pancreatic endoderm cells expressing PDX1 and NKX6.1, endocrine progenitors, endocrine progenitors expressing NKX6.1 and INS, immature beta cell, immature beta cells expressing NKX6.1, INS and MAFB, mature endocrine cells, mature endocrine cells expressing INS, GCG, SST and PP, and mature beta cells and mature beta cells expressing INS and MAFA.

Perforated delivery devices loaded with pancreatic endoderm cells ("perforated combination product") which mature when implanted in vivo are intended to reduce insulin dependence and/or reduce hypoglycemia in high-risk type I diabetic patients who are hypoglycemia unaware, labile (brittle), or have received an organ transplant and who can tolerate, or are already on, immune suppression therapy. The primary method of action is via human pancreatic endoderm cells (PEC) or pancreatic progenitor cells, contained in a permeable, durable, implantable medical device that facilitates direct host vascularization. The PEC cells differentiate and mature into therapeutic glucose-responsive, insulin-releasing cells after implantation. As such, the perforated combination product supports secretion of human insulin. The perforated combination product limits distribution (egress) of PEC cells in vivo. The perforated combination product will be implanted in a location that permits sufficient vascular engraftment to sustain the population of therapeutic cells within the device and facilitate distribution of insulin and other pancreatic products to the bloodstream. The perforated combination product is intended to be implanted and explanted with conventional surgical tools, and to provide a therapeutic dose for two years or more. The device is intended to retain an adequate dose of the PEC cell product during formulation, shelf-life, handling and surgical implant to achieve clinical efficacy and ensure the cell product is located within the tissue capsule to meet safety requirements.

The perforated combination product is comprised of a Perforated Device (PD) containing a dose of PEC, a human pancreatic progenitor cell therapy product. After implantation into a patient, the perforated combination product is designed to enable device integration and direct vascularization of the implanted cell product, to permit differentiation and maturation of PEC cells into glucose-responsive, insulin-producing cells for treatment of insulin-requiring patients.

A perforated device (PD) is defined as a durable, biocompatible, easily-removable implant device comprised of stacked material layers that are bonded together to form a cell-containing lumen. The device is comprised of biocompatible and biostable materials intended for long-term implantation. A semi-permeable membrane permits diffusion of nutrients to the lumen immediately post-implantation to sustain implanted cell viability, while in parallel, perforations in the membrane enable growth of host blood vessels into the device lumen and directly to the implanted cells, improving perfusion and release of implanted cell products, including insulin, into the bloodstream.

Because the PD contains perforations large enough to allow invasion or ingress of host blood vessels, other host cells will migrate into the device's cell-containing lumen, including immune cells, necessitating the use of immune suppression medications.

The perforated combination product is expected to be implanted for a period of five years, but is required to meet its intended use for at least two years. The design intent of the PD is to provide a defined, protected space for early survival and differentiation/maturation of implanted cells during the period of capsule formation, and retain the bulk of such cells throughout the period of engraftment. Device components must be biocompatible. Two device configurations are being developed for clinical study: a device with sufficient volume to potentially achieve therapeutic dosing, and a smaller unit suitable for easy implant and explant to assess engraftment and host tissue response via histology at intermediate time points (sentinel). The size and number of perforations in the device should be chosen to allow ingress of adequate quantities of host blood vessels directly into the implanted cells, without impairing the ability of the perforated device to retain adequate cell dose to provide efficacy. Further, the perforated device shall ensure that an adequate quantity of implanted cells is removed from the body during product explant, which will include surrounding host tissue capsule, to satisfy safety requirements.

The design of the PD and perforated combination product have additional benefits related to their similarities to the intact (without holes) cell delivery device. These include:

The PD leverages the same materials, similar manufacturing processes, and the extensive biocompatibility testing established for the intact cell encapsulation devices previously disclosed by Applicants in U.S. Pat. No. 8,278,106 and U.S. application Ser. No. 14/201,630.

Since the intact and perforated devices share similar geometry and handling characteristics, the surgical procedures for both implant and explant are intended to be the same for both products. In summary, the perforated combination product is designed to leverage existing manufacturing processes of, and clinical experience with, the intact cell encapsulation devices for cell product delivery.

Other embodiments are described with reference to the numbered paragraphs below:

A cell delivery device comprising a non-woven fabric.

The cell delivery device of paragraph 24, further comprising a cell-excluding membrane wherein the non-woven fabric is external to the cell-excluding membrane.

A cell delivery device comprising a cell-excluding membrane and a non-woven fabric external to the cell-excluding membrane wherein only the cell-excluding membrane is perforated.

The cell delivery device of paragraph 26, wherein host blood vessels come in direct contact with a lumen of the cell delivery device.

A cell delivery device comprising a cell-excluding membrane and a non-woven fabric external to the cell-excluding membrane wherein only the non-woven fabric is perforated.

The cell delivery device of paragraph 28, wherein host blood vessels come in direct contact with the outer surface of the cell delivery device.

A cell delivery device comprising a cell excluding membrane, a non-woven fabric external to the cell-excluding membrane and either a mesh layer, film weld or both wherein the non-woven fabric and cell-excluding membrane are perforated.

The cell delivery device of paragraph 30, wherein host blood vessels come in direct contact with a lumen of the cell delivery device.

A cell delivery device comprising a cell-excluding membrane and a non-woven fabric external to the cell-excluding membrane wherein only the non-woven fabric and cell-excluding membrane are perforated.

The cell delivery device of paragraph 32, wherein host blood vessels come in direct contact with the outer surface of the cell delivery device.

The cell delivery device of paragraph 32, wherein host blood vessels form entirely through the cell delivery device and come in direct contact with a therapeutic agent loaded into the cell delivery device.

The cell delivery device of paragraph 32, wherein the non-woven fabric is laminated to the cell excluding membrane.

The cell delivery device of paragraph 32, wherein the cell delivery device is implanted into a mammalian host treated with at least one immunosuppressant drug.

The cell delivery device of paragraph 36, wherein the immunosuppressive drug is selected from the group consisting of calcineurin inhibitors, anti-metabolite immunosuppressives, and combinations thereof.

The cell delivery device of paragraph 37, wherein the immunosuppressive drug is selected from the group consisting of Cyclosporine A (CsA), Mycophenolate Mofetil (MMF), Tacrolimus (TAC) and combinations thereof.

A cell delivery device comprising a perforated non-woven fabric implanted into a host treated with immunosuppressive drugs.

A cell delivery device comprising a non-woven fabric outside the cell-excluding membrane implanted into a host treated with immunosuppressive drugs.

The cell delivery device of paragraph 39 or 40, wherein the non-woven fabric is perforated.

The cell delivery device of paragraph 41, wherein the cell-excluding membrane is perforated.

The cell delivery device of paragraph 42, wherein the cell-excluding membrane and non-woven fabric are perforated.

The cell delivery device of paragraph 39 or 40, wherein the immunosuppressive drug is selected from the group consisting of calcineurin inhibitors, anti-metabolite immunosuppressives, and combinations thereof.

The cell delivery device of paragraph 44, wherein the immunosuppressive drug is selected from the group consisting of Cyclosporine A (CsA), Mycophenolate Mofetil (MMF), Tacrolimus (TAC) and combinations thereof.

The cell delivery device of paragraph 39 or 40, wherein the cell delivery device comprises a cell-excluding membrane wherein the non-woven fabric is laminated to a cell excluding membrane.

A method for promoting survival of cells transplanted in vivo in a mammal, said method comprising: a) loading cells into a perforated cell delivery device; and b) implanting the perforated device containing cells into a mammalian host thereby promoting cell survival of transplanted cells.

The method of paragraph 47, wherein the cells are pancreatic endoderm cells.

The method of paragraph 47, wherein the mammal is not a mouse.

The method of paragraph 47, wherein the mammal is a human or rat.

A method of lowering blood glucose in a mammal comprising: 1) loading cells into a cell delivery device wherein the device comprises a perforated cell-excluding membrane and a perforated non-woven fabric external to the cell-excluding membrane and no other perforated layers; b) implanting the cell delivery device into a mammalian host; and c) maturing the implanted cells thereby lowering blood glucose in a mammal.

A cell delivery device comprising a cell-excluding membrane and a non-woven fabric external to the cell-excluding membrane wherein the non-woven fabric is laminated to the cell-excluding membrane.

The cell delivery device of paragraph 52, wherein the non-woven fabric and the cell-excluding membrane are perforated.

A cell delivery device comprising a cell-excluding membrane and no NWF wherein only the cell-excluding membrane is perforated.

A cell delivery device comprising a cell-excluding membrane and no NWF implanted into a mammal treated with an ISD wherein only the cell-excluding membrane is perforated.

A cell delivery device comprising a cell-excluding membrane and no NWF implanted into a rat or human treated with an ISD wherein only the cell-excluding membrane is perforated.

A cell delivery device comprising a cell-excluding membrane and no NWF implanted into a mammal not treated with an ISD wherein only the cell-excluding membrane is perforated.

A cell delivery device comprising a cell-excluding membrane and no NWF implanted into a rat or human not treated with an ISD wherein only the cell-excluding membrane is perforated.

A cell delivery device comprising a cell-excluding membrane and NWF wherein only the cell-excluding membrane and NWF are perforated.

A cell delivery device comprising a cell-excluding membrane and NWF implanted into a mammal treated with an ISD wherein only the cell-excluding membrane and NWF are perforated.

A cell delivery device comprising a cell-excluding membrane and NWF implanted into a rat or human treated with an ISD wherein only the cell-excluding membrane and NWF are perforated.

A cell delivery device comprising a cell-excluding membrane and NWF implanted into a mammal not treated with an ISD wherein only the cell-excluding membrane and NWF are perforated.

A cell delivery device comprising a cell-excluding membrane and NWF implanted into a rat or human not treated with an ISD wherein only the cell-excluding membrane and NWF are perforated.

A cell delivery device comprising an intact cell-excluding membrane and no NWF.

A cell delivery device comprising an intact cell-excluding membrane and no NWF implanted into a mammal treated with an ISD.

A cell delivery device comprising an intact cell-excluding membrane and no NWF implanted into a rat or human treated with an ISD.

A cell delivery device comprising an intact cell-excluding membrane and no NWF implanted into a mammal not treated with an ISD.

A cell delivery device comprising an intact cell-excluding membrane and no NWF implanted into a rat or human not treated with an ISD.

A cell delivery device comprising an intact cell-excluding membrane and an intact NWF.

A cell delivery device comprising an intact cell-excluding membrane and an intact NWF implanted into a mammal treated with an ISD.

A cell delivery device comprising an intact cell-excluding membrane and an intact NWF implanted into a rat or human treated with an ISD.

A cell delivery device comprising an intact cell-excluding membrane and an intact NWF implanted into a mammal not treated with an ISD.

A cell delivery device comprising an intact cell-excluding membrane and an intact NWF implanted into a rat or human not treated with an ISD.

Immunosuppression

Implanting mature islet cells while also treating the host with an immunosuppressive compound has been previously disclosed. See U.S. Pat. No. 9,062,290 which is herein incorporated in its entirety by reference. But, it has been reported that calcineurin inhibitors are (1) diabetogenic (producing diabetes) (reviewed in Crutchlow M F, Transplant-associated hyperglycemia: a new look at an old problem *Clin J Am Soc Nephrol.* 2(2):343-55 (2007)) and (2) negatively impact endogenous pancreatic regeneration in mice (See Heit J, Calcineurin/NFAT signaling regulates pancreatic beta-cell growth and function *Nature* 21; 443 (7109):345-9 (2006) and Nir T, Recovery from diabetes in mice by beta cell regeneration *J Clin Invest* 117(9):2553-61 (2007)). As such, it was unknown and could not be predicted whether immature pancreatic progenitors could mature in vivo in the presence of calcineurin inhibitors, and if they do mature, whether the mature graft could survive and function when the host is treated with immunosuppressants.

Even treatment of type I diabetes with pancreatic islet allografts has not been effective in freeing many patients from exogenous insulin injections for long periods of time. One problem has been that the immunosuppressive reagents required to inhibit allograft rejection can severely compromise transplanted islet cell function. Cellular and Molecular Approaches to Achieving *Euglycemia* (1997), *NIH Guide* 26(38).

Embodiments described herein are directed to implanted perforated devices containing cells wherein the host is treated with immunosuppression drugs. In one embodiment, perforated devices comprising at least one layer of a non-woven fabric facing the host such as a NWF wherein the host is treated with immunosuppression drugs. In one embodiment, perforated devices comprising at least one layer of a NWF laminated to the cell excluding membrane and facing the host wherein the host is treated with immunosuppression drugs. In one embodiment, the immunosuppressive drug is selected from the group consisting of calcineurin inhibitors, anti-metabolite immunosuppressives, and combinations thereof. In one embodiment, the immunosuppressive drug is selected from the group consisting of Cyclosporine A (CsA), Mycophenolate Mofetil (MMF), Tacrolimus (TAC) and combinations thereof. In one embodiment the immunosuppression drug is administered to a host implanted with an un-perforated device.

In one embodiment, a method of administering a therapeutically effective amount of a therapeutic agent in a perforated cell delivery device to a host treated with an immunosuppression drug is disclosed.

Other embodiments are described with reference to the numbered paragraphs below:

A method for producing insulin in vivo in a mammal, said method comprising: a) administering to a mammalian host an immunosuppressive drug; b) implanting a perforated device containing pancreatic endoderm cells into a mammalian host; and c) maturing the pancreatic endoderm cell population in said perforated device in vivo such that the progenitor cell population matures to insulin-secreting cells, thereby producing insulin in vivo in the mammal.

The method of paragraph 62, wherein the immunosuppressive drug is selected from the group consisting of calcineurin inhibitors, anti-metabolite immunosuppressives, and combinations thereof.

The method of paragraph 63, wherein the immunosuppressive drug is selected from the group consisting of Cyclosporine A (CsA), Mycophenolate Mofetil (MMF), Tacrolimus (TAC) and combinations thereof.

The method of paragraph 62, wherein the perforated device comprises at least one layer of a cell-excluding membrane and a non-woven fabric external to the cell-excluding membrane.

The method of paragraph 665, wherein the non-woven fabric is laminated to a cell excluding membrane.

A perforated cell delivery device comprising pancreatic endoderm cells implanted into a host treated with immunosuppressive drugs.

The perforated cell delivery device of paragraph 67, wherein the immunosuppressive drug is selected from the group consisting of calcineurin inhibitors, anti-metabolite immunosuppressives, and combinations thereof.

The perforated cell delivery device of paragraph 68, wherein the immunosuppressive drug is selected from the group consisting of Cyclosporine A (CsA), Mycophenolate Mofetil (MMF), Tacrolimus (TAC) and combinations thereof.

The perforated cell delivery device of paragraph 67, wherein the perforated device comprises at least one layer of non-woven fabric.

The perforated cell delivery device of paragraph 70, wherein the perforated device comprises a cell-excluding membrane wherein the non-woven fabric is laminated to a cell excluding membrane.

A method of improving survival of therapeutic cells in a mammalian subject comprising administering to said subject an effective amount of therapeutic cells in a perforated cell delivery device and an effective amount of immunosuppressant, wherein the effective amount of immunosuppressant, does not compromise the ability of the therapeutic cells to survive and mature in vivo.

A method of producing insulin in a mammal, comprising the steps of: implanting the host with pancreatic endoderm; administering an effective dosage of an immunosuppressant to the host, and allowing the pancreatic endoderm to mature into insulin-producing cells in the mammal thereby producing insulin in the mammal.

A method of inhibiting or modulating an immunologic or inflammatory reaction in a host to implanted xeno or allogeneic cells comprising delivery the cells in a perforated cell delivery device and administering to the host an effective amount of anti-inflammatory factor or immunosuppressant drug wherein the cells are pancreatic endoderm.

A method of treating diabetes in a subject, comprising (a) administering to the diabetic subject an immunosuppressant drug; and (b) administering to the subject pancreatic endoderm cells in a perforated cell delivery device wherein the pancreatic endoderm cells mature into insulin-producing cells thereby treating diabetes in a subject.

Additional features and advantages of the embodiments described herein will be apparent from, the detailed description, drawings, and examples.

Use of perforated devices in normal human patients will require chronic immunosuppressant drug (ISD) therapy. Because of the adverse effects caused by ISDs, it was not known if Applicant's proprietary PDX1-positive pancreatic endoderm cells or pancreatic progenitors (aka "PEC") implanted in a host receiving ISDs would be (1) able to mature and (2) if the mature cells would remain viable and biologically active and produce insulin in response to blood glucose levels since previous work showed that certain calcineurin inhibitors were diabetogenic (producing diabetes) see Crutchlow et al (2007) supra) and negatively impact endogenous pancreatic regeneration in mice (Heit (2006) supra). Applicants surprisingly found that PEC implanted in a perforated device continued to differentiate and function in nude rats receiving ISDs as evidenced by the fact that serum levels of human c-peptide in cyclosporine A treated animals were similar to levels measured in untreated control rats. Additionally, the initial hyperglycemia observed in CsA treated rats was reversed. This remained true for at least 30 weeks after implant, indicating a lack of graft sensitivity to supra-therapeutic levels of calcineurin inhibition through cyclosporine A. A follow-on study further tested pancreatic endoderm in a perforated device and implanted in a host receiving a combination of CsA or tacrolimus (TAC) with mycophenolate mofetil (MMF). This study established pancreatic endoderm and graft tolerance to all ISD regimens tested. In summary, the function of pancreatic endoderm and grafts appeared not to be negatively affected by the combined presence of hyperglycemia and calcineurin inhibition contrary to what one would expect from previous literature reports. As such a skilled artisan would expect that the function of pancreatic endoderm and grafts would not be negatively affected by most commonly used drugs to maintain immunosuppression.

In one embodiment, the device is implanted in the pre-peritoneal.

RELEVANT LITERATURE

Encapsulation of pancreatic cells derived from human pluripotent stem cells is described by Martinson et al., U.S. Pat. No. 8,278,106, issued Oct. 2, 2012. Tools and instruments for use with implantable encapsulation devices are described in U.S. application Ser. No. 14/254,844 filed Apr. 16, 2014, and in U.S. design nos. 29/488,209, 29/488,217, 29/488,191, 29/488,204. Instruments and methods for loading cells into Implantable devices is described in PCT/US2014/060306 filed Oct. 13, 2014. LOADING SYSTEM FOR AN ENCAPSULATION DEVICES are described in U.S. application Ser. No. 14/000,864 filed Aug. 21, 2013. 3-DIMENSIONAL LARGE CAPACITY CELL ENCAPSULATION DEVICE ASSEMBLIES are described in U.S. application Ser. No. 14/201,630 filed Mar. 7, 2014, and in U.S. Design nos. 29/447,944, 29/509,102, 29/484,363, 29/484,360, 29/484,359, 29/484,357, 29/484,356, 29/484,355, 29/484,362, and 29/484,358. CELL ENCAPSULATION DEVICES are described in U.S. Design Nos. 29/408,366, 29/517,319, 29/408,368, 29/518,513, 29/518,516, 29/408,370, 29/517,144, 29/423,365, 29/530,325. CULTURING OF HUMAN EMBRYONIC STEM CELLS INTO PANCREATIC ENDOCRINE CELLS is described in Ser. Nos. 13/998,884 and 62/352,968. FORAMINOUS IMPLANT is described in WO1993/02635. Each above-referenced patent/application is incorporated by reference herein in their entirety.

All publications and patents mentioned in this specification are herein incorporated in their entireties by reference.

EXAMPLES

It should also be understood that the foregoing relates to illustrated embodiments and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the illustrated embodiments and/or the scope of the appended claims.

Example 1: Cell Delivery Device with Various Densities of a Non-Woven Fabric

EN20 devices typically consist of 3 layers: 1) an inner cell-excluding membrane; 2) a middle film ring; and 3) and an outer layer of woven mesh. During the manufacturing process, when the 3 components are ultrasonically welded (or sealed) together the cell-excluding membrane may become compressed by the stiffer mesh, especially near the transition area between the weld and the lumen. Extreme flexure of the devices can also lead to compression areas in the membrane. These compression areas can potentially lead to breaches in the membrane compromising device integrity (e.g. cell leakage out of the device). In order to improve the structural integrity of the device while at the same time maintain its functionality (cell excluding, vascularizing, biocompatible and the like), additional materials and/or layers were studied. Non-woven fabrics were identified as potential intervening buffer layers.

Figure 4:
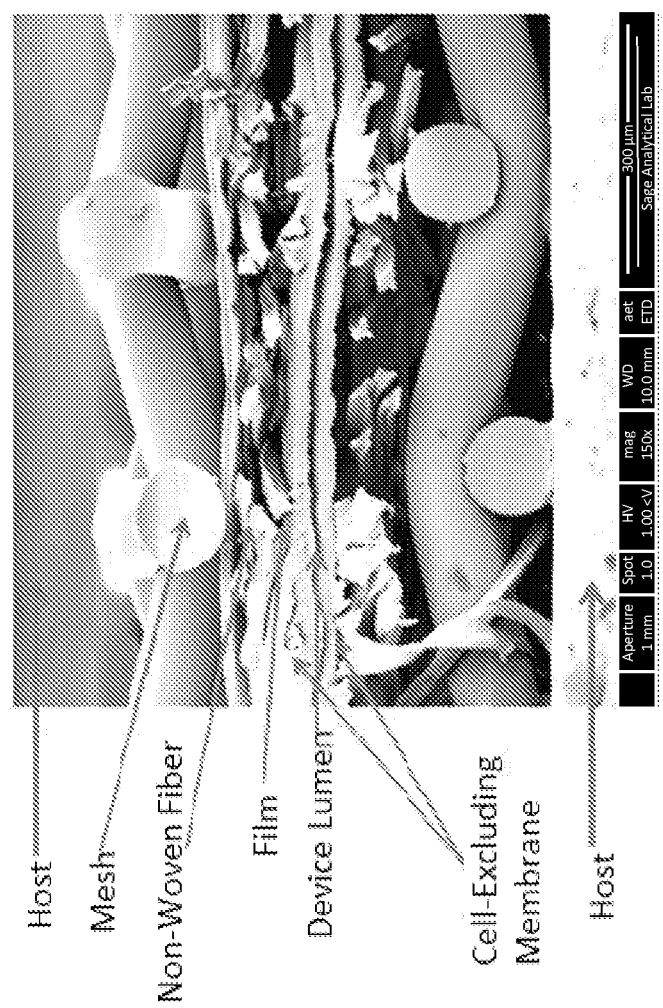
FIG. 4 is an image of a cross section of a cell delivery device with an added non-woven fabric layer.

New devices were made using a non-woven fabric. As discussed above, the device components (non-woven fabric, film, mesh, and membrane) may be arranged in various patterns. Here, the non-woven fabric was added between the outer woven mesh layer and the outer surface of the cell-excluding membrane using a variety of fiber densities: 0.40, 0.75 and 1.00 oz/yd$^2$. See FIG. 4 which shows a cross-section of a delivery device with added non-woven fabric.

The non-woven fabric was either not laminated to the cell-excluding membrane or was heat laminated using a custom polyethylene, dry adhesive web (e.g., Part Number Spunfab P04605, SpunFab, Inc.), to the cell-excluding membrane. See Table 5. This adhesive was selected for its low basic weight (0.145 oz/yd$^2$) to inhibit occlusion of the cell-excluding membrane pores during the lamination process.

This study was conducted in two cohorts of SCID-Bg mice. Cryopreserved pancreatic endoderm cells (called "PEC") were thawed, cultured in Dulbecco's media comprising DMEM/HI Glucose (27 mM) and B27 and loaded into an EN20 size device for each cohort separately.

TABLE 6

Various device configurations for Cohort 1

| Group | NWF Between Cell-Excluding Membrane And Mesh | NWF Density | Laminated To Cell-Excluding Membrane | Number Of Implants |
|---|---|---|---|---|
| EN20 Con-1 | No | N/A | N/A | n = 15 |
| EN20-NWF (2) | Yes | 0.75 oz/yd^2 | No | n = 15 |
| EN20-NWF (2)-SB | Yes | 0.75 oz/yd^2 | Yes | n = 15 |

TABLE 7

Various device configurations for Cohort 2

| Group | NWF Between Cell-Excluding Membrane And Mesh | NWF Density | Laminated To Cell-Excluding Membrane | Number Of Implants |
|---|---|---|---|---|
| EN20 Con-2 | No | N/A | N/A | n = 15 |
| EN20-NWF (3) | Yes | 0.40 oz/yd^2 | No | n = 15 |
| EN20-NWF (1) | Yes | 1.00 oz/yd^2 | No | n = 15 |

To determine the functionality of the various configurations, glucose-stimulated insulin secretion (GSIS) assays were performed about 8, 13, 16 and 22 weeks post-implant as described in Kroon et al., 2009, supra; and Agulnick eta 2015, supra. Specifically, prior to the GSIS assay, mice fasted for approximately 15-18 hours. Glucose was administered via intraperitoneal injection of about 30% dextrose (Hospira) solution at a dose of about 3.0 g/kg body weight, and blood was collected prior to (fasting) and at 30 and/or 60 minutes after glucose administration. Blood samples of approximately 50 µL were collected by retro-orbital sinus puncture under isoflurane anesthesia and transferred to microtiter tubes (BD Biosciences, cat #365956) containing blood/serum separation gel. Serum was collected after spinning these tubes at 4000-6000×g for 10 minutes. Serum from the blood samples was analyzed for human c-peptide using an ELISA assay (Mercodia Ultrasensitive Human c-peptide ELISA, cat #10-1141-01).

Table 8 shows that devices incorporating the NWF gave improved function as measured by human c-peptide in the serum after glucose stimulation compared to control devices (no NWF used).

For example, maximal c-peptide values were achieved from mice implanted with EN20-NWF (2) (0.75 oz/yd^2, not laminated to the cell-excluding membrane). c-peptide values were about 2.5 fold greater than the EN20 Control-1 devices at both 13 (1945 pM vs 841 pM) and 16 weeks (3697 pM vs 1326 pM) post-implant. Mice implanted with EN20-NWF (2)-SB (non-woven PET material was laminated with polyethylene adhesive web to the cell-excluding membrane) had about 1.5 fold higher human c-peptide serum values at both 13 (1314 pM vs 841 pM) and 16 weeks (1696 pM vs 1326 pM) post-implant.

Similarly, when other densities of non-woven PET material were used (NWF (3) and NWF (1), 0.40 and 1.00 oz/yd^2, respectively, not laminated to the cell-excluding membrane), c-peptide values were about 2.5 fold higher than mice implanted with EN20 Control-2 devices at 13 weeks (1603 pM for devices with NWF (3) vs 644 pM for EN20 Control-2 and 1482 pM for devices with NWF (1) vs 644 pM for EN20 Control-2) and at 16 weeks (2186 pM for devices with NWF (3) vs 826 pM for EN20 Control-2 and 2285 pM for devices with NWF (1) vs 826 pM for EN20 Control-2) post-implant. (See Table 8.)

TABLE 8

GSIS Data for Mice Implanted With Cell Delivery Devices Made With NWF at Various Densities

| | MAX C-pep | | | | | | | | |
|---|---|---|---|---|---|---|---|---|---|
| | 13 weeks | | | | | 16 weeks | | | |
| Group | n | Mean | SD | ≥500 pM | % Con | n | Mean | SD | ≥1000 pM | % Con |
| EN20 Con-1 | 10 | 841 | 574 | 7/10 | 100[a] | 10 | 1326 | 946 | 7/10 | 100[a] |
| EN20-NWF (2) (not laminated) | 10 | 1945 | 745 | 10/10 | 231[a] | 10 | 3697 | 1726 | 10/10 | 279[a] |
| EN20-NWF (2) - SB | 7 | 1314 | 966 | 7/7 | 156[a] | 7 | 1696 | 429 | 6/7 | 128[a] |
| EN20 Con-2 | 11 | 644 | 650 | 5/11 | 100[b] | 11 | 826 | 562 | 4/11 | 100[b] |
| EN20-NWF (3) (not laminated) | 12 | 1603 | 1195 | 11/12 | 249[b] | 12 | 2168 | 1133 | 11/12 | 262[b] |
| EN20-NWF (1) (not laminated) | 12 | 1482 | 1028 | 10/12 | 230[b] | 12 | 2285 | 1279 | 10/12 | 277[b] |

% Control value[a] relative to EN20 Control-1 Group.
% Control value[b] relative to EN20 Control-2 Group.

Histological analyses of explanted grafts indicate increased vascularization around the devices containing NWF between the cell-excluding membrane and mesh layer as compared to the control devices without the NWF, suggesting that the NWF contributed to the improved functional performance of the devices as indicated by significantly higher human-C peptide serum levels after glucose stimulation compared to the control.

Although the NWF between the cell-excluding membrane and outer mesh improved the functional performance of the EN20 device in vivo, the various different densities (basic weight) of NWF (1), (2) or (3) did not appear to significantly affect the functional performance (compare EN20-NWF (3) and EN20-NWF (1) in cohort 2 in Table 8). Surprisingly, those devices in which the NWF was not laminated to the cell-membrane layer (EN20-NWF (2) of Cohort 1; and EN20-NWF (3), EN20-NWF (1) of Cohort 2) had improved functional performance (2.5 and 1.5 folds higher of serum human c-peptide) as compared to devices in which the non-woven PET layer was laminated (EN20-NWF (2)-SB of Cohort 1) to the cell-excluding membrane with a polyethylene adhesive web. From this, it is concluded that the presence of the NWF (laminated or not) has the most significant effect on the functionality of the delivery cells.

12 and 16 weeks post-implant, respectively (compare 241% vs 100% and 185% vs 100%); while mice implanted with EN20-NWF (2)-HL (heat laminated) had about 2.8 and 2.30 fold higher values relative to the controls at 12 and 16 weeks post-implant, respectively (compare 278% vs 100% and 229% vs 100%).

This demonstrates that lamination of the non-woven fabric to the cell-excluding membrane had an improved effect on the functionality of the cells in the device (compare 241% vs 278% at 12 weeks and 185% vs 229% at 16 weeks). However, as above, it is the presence of the non-woven fabric (laminated or not) that had the most significant effect on the functionality of the cells. That is, the devices with a non-woven fabric had at least 1.9 fold greater c-peptide values than the control device without the non-woven fabric.

TABLE 9

GSIS Data for Mice Implanted With Cell Delivery Devices with Non-Woven Fabric Laminated or Not Laminated To the Cell Excluding Membrane

| | MAX c-peptide, 12 week GSIS | | | | | MAX c-peptide 16 week GSIS | | | |
|---|---|---|---|---|---|---|---|---|---|
| Group | N | Mean | SD | ≥500 pM | % Con* | N | Mean | SD | ≥1000 pM | % Con |
| EN20 Control | 11 | 500 | 570 | 2/11 | 100 | 10 | 1206 | 750 | 4/10 | 100 |
| EN20- NWF (2) | 10 | 1207 | 608 | 7/10 | 241 | 10 | 2227 | 1592 | 9/10 | 185 |
| EN20- NWF (2) - HL | 10 | 1390 | 628 | 9/10 | 278 | 9 | 2736 | 1136 | 9/9 | 229 |

*Standard deviation
**Results expressed as a percentage of control GSIS response Example 2: Lamination of the Non-Woven Fabric to the Cell-Excluding Membrane in Cell Delivery Devices The effect of lamination of the NWF layer to the cell-excluding membrane layer was investigated further. At least 3 configurations of the small 20 μL cell delivery devices were constructed ("EN20"). The control devices consisted of an innermost layer of a cell-excluding membrane and an outermost layer of mesh ("EN20 Control"). The experimental devices consisted of an innermost layer of a cell-excluding membrane, a middle NWF, and an outermost layer of mesh. In one configuration, the NWF was not laminated to the cell-excluding membrane ("EN20-NWF (2)"). In another configuration, the NWF was laminated to the cell-excluding membrane using heat and pressure ("EN20-NWF (2)-HL"). Heat lamination of the cell-excluding membrane and NWF (a.k.a. heat stacking) was performed using a standard thermal press machine (e.g., ARB Arbor Press, Plastic Assembly Systems). The press was heated to between 305-320° F., and a pressure of between 0-6 PSI was applied at a rate of 3 feet/minute or 10 feet/minute.

All finished devices were sterilized and aseptically loaded with research grade pancreatic progenitor cells derived from human pluripotent stem cells and implanted into SCID-Bg mice as previously described in detail in at least Kroon et al. 2008 supra, and Agulnick et. al. 2015 supra. To determine the functionality of the various configurations, glucose-stimulated insulin secretion (GSIS) assays were performed about 12 and 16 weeks post-implant as described in Example 1.

Maximal c-peptide values obtained from mice implanted with EN20-NWF (2) (not heat laminated) devices were about 2.4 and 1.9 fold greater than EN20 Control devices at It appears that the non-woven fabric improves engraftment of the devices by improving host vascularization of the device, thereby improving cell viability, proliferation, development, maturation and function inside the device.

Example 3: Optimization of Hole Density in Perforated Devices

Applicants seek to characterize the optimal number of perforations (density) for macro cell delivery devices. Table 2 below describes perforated cell delivery devices with and without a perforated non-woven fabric, wherein the density (number of perforations each approximately 100 micron in size per device) is varied. It should be noted that in general the NWF layer has inconsistent pores or gaps due to its non-woven structure. Hence, some pores or gaps may be less than 100 microns whereas others are greater than 100 microns. The NWF layer may have a basic weight of about 0.4 to 0.75 oz/yd$^2$, a nominal thickness of about 127 to 228 μm and fiber diameter of 26 μm. There exists various methods for perforating the device, for example, all the layers can be first layered on top of each other and then each layer of both sides or walls of the device are perforated. Alternatively, just the cell excluding layer is perforated and then combined with the other non-perforated layers of the device including the NWF layer. Perforating with a laser provides greater control over hole size (diameter) and number of perforations (density). In Groups 1-3 in Table 2 below, just the cell-excluding membrane was laser-perforated to form holes having a mean diameter of about 87 μm and ranging from about 50 to 120 μm and spaced approximately 1 mm, 1.5 mm, or 2 mm from each other. A small-gauge hypodermic needle was used to manually create holes approximately 2 mm from each other in each layer of the control groups (group 4 and group 5).

TABLE 2

Parameters for Perforated Devices

| Group Number | NWF | Cell Excluding Membrane Perforations (Type - Spacing) | Number of Articles | Number of Animals | In-Life Period (weeks) |
|---|---|---|---|---|---|
| 1 | Yes | Laser - 1 mm | 8 | 4 | 34 |
| 2 | Yes | Laser - 1.5 mm | 8 | 4 | 34 |
| 3 | Yes | Laser - 2 mm | 8 | 4 | 34 |
| 4 | Yes | Needle - 2 mm | 8 | 4 | 34 |
| Control-5 | No | Needle - 2 mm | 8 | 4 | 34 |
| | | TOTAL | 40 | 20 | |

All animals (athymic nude rats) received two subcutaneous grafts of test or control EN20 devices, each containing about 20 μL settled pancreatic progenitor cell aggregates.

Figure 5:
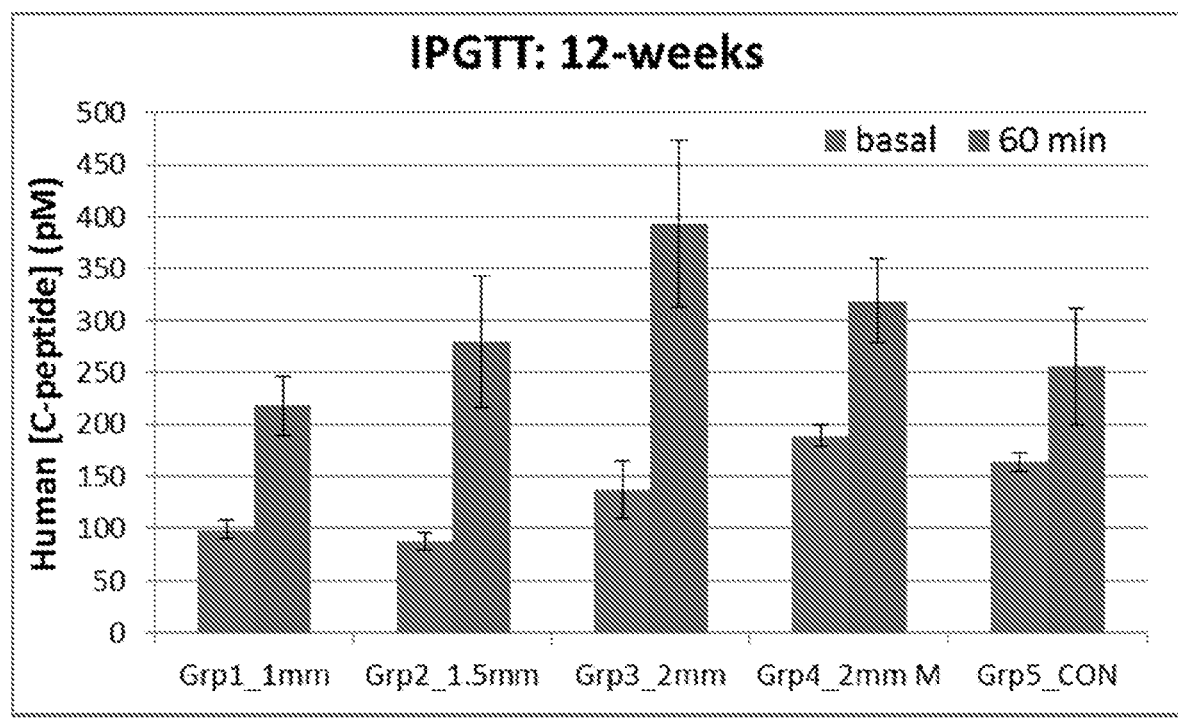
FIG. 5 is a graph showing the concentration of human c-peptide in sera of rats implanted with pancreatic progenitors delivered in a needle perforated delivery device (control, CON) and in laser perforated devices. Secreted C-peptide levels were analyzed 12 weeks post-engraftment at fasting and 60 min after intraperitoneal glucose administration. Mean c-peptide concentration (+/−SEM). "M" refers to the manual formation of holes with a needle and 2 mm spacing as approximated.
Figure 6:
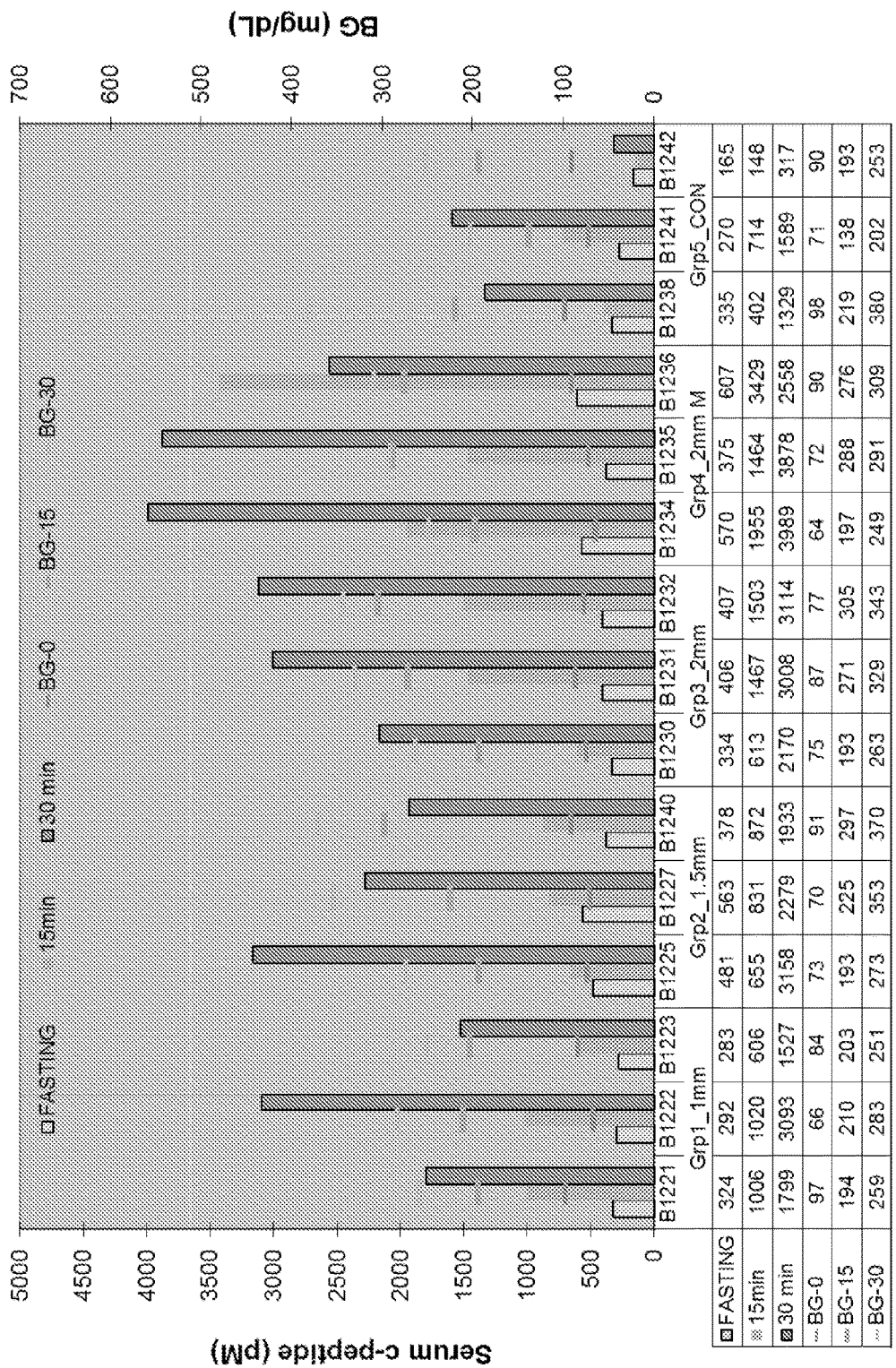
FIG. 6 is a graph showing the concentrations of human c-peptide in sera of rats implanted with pancreatic progenitors delivered in a needle (manually) perforated delivery device (control, CON) and in laser perforated devices. Secreted C-peptide levels were analyzed 34 weeks post-engraftment at fasting, 15 min, and 30 min after intraperitoneal glucose administration. "M" refers to the manual formation of holes with a needle and 2 mm spacing is approximated.

All device configurations (laser generated holes separated by about 1, 1.5 and 2 mm as well as needle holes separated by about 2 mm) allowed for survival, proliferation, development and maturation of the pancreatic progenitors into functional pancreatic endocrine cells in athymic nude rats as indicated by human c-peptide levels shown in FIG. 5. When GSIS assays (as substantially described in Kroon et al. (2008) supra; Agulnick et al (2015) supra) were performed 34 weeks post-implant, cells in all the perforated devices, independent of hole density, performed as well as the control devices 15 and 30 minutes post glucose challenge. See FIG. 6.

One of skill in the art would hypothesize that if increasing cell-to-cell contact between implanted and host cells, specifically host vasculature, leads to increase cell survival, proliferation and maturation, then the more holes in any device the better. So, it was surprising that Applicants discovered that cells in devices with lower hole density performed just as well as devices with a greater density of holes. For example, devices with holes spaced 2 mm apart (holes spaced further apart means fewer holes and lower density) performed just as well as those devices with holes spaced less than 2 mm apart (closer together means more holes and higher density). As such, Applicant discovered that hole density or number of perforations can be relatively few (approximately 20 perforations per wall of the device in a small EN20 size device which is less than about 0.4% of the device's surface area is perforated) and still provide the desired benefit of direct host vascularization and cell survival. It was surprising because one of ordinary skill in the art would expect that with more holes (greater density) means more and/or faster host vascularization, which aids in the delivery of oxygen and other nutrients to the implanted cells, thereby increasing cell survival and differentiation.

Devices with a lower hole densities may be preferred since fewer holes provides improved safety by reducing or inhibiting cell escape from the device. Further, it is desirable to retain the cells inside the device which allows for entire graft retrieval should the entire implant be removed.

Figure 3:
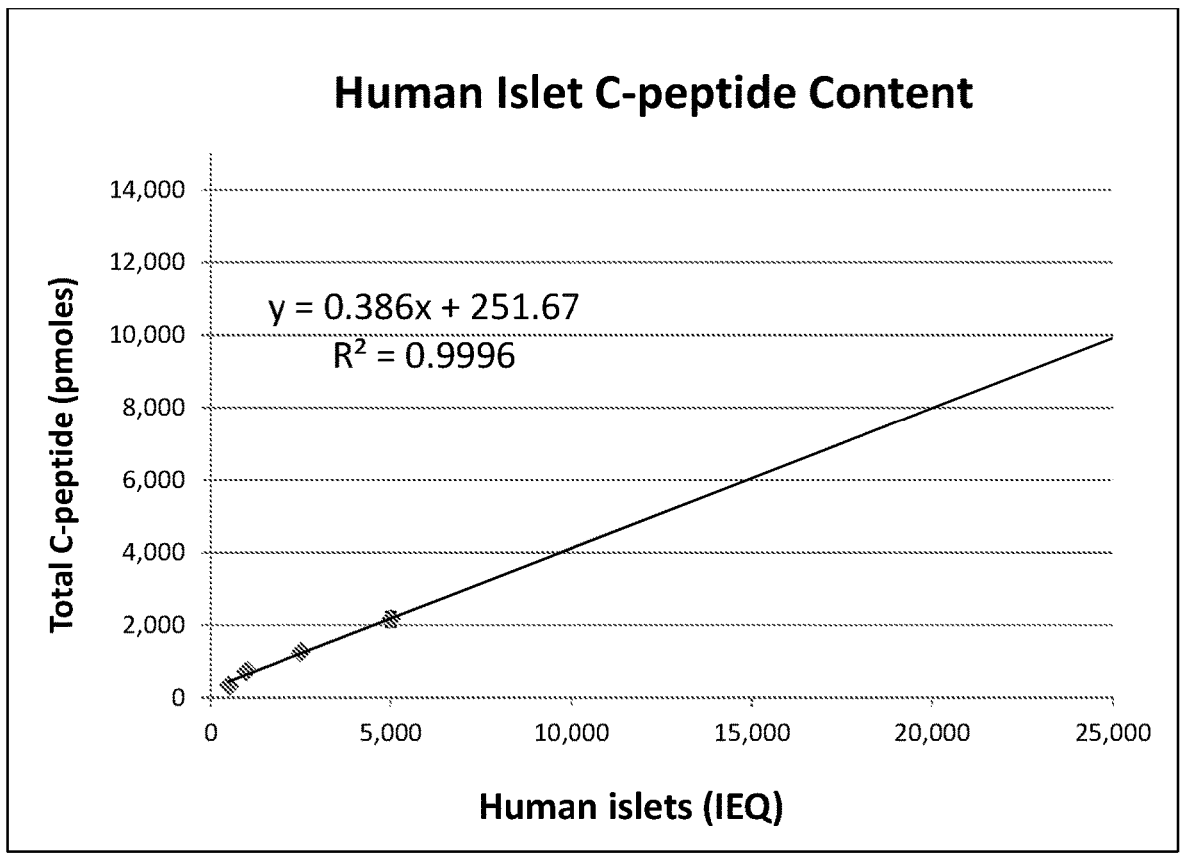
FIG. 3 is a graph showing the correlation between total C-peptide protein content and beta cell mass expressed as islet equivalents (IEQ). This graph can be used to determine the beta cell mass produced after implantation of pancreatic cells in a perforated cell encapsulation device, expressed as islet equivalents (IEQ).
Figure 7:
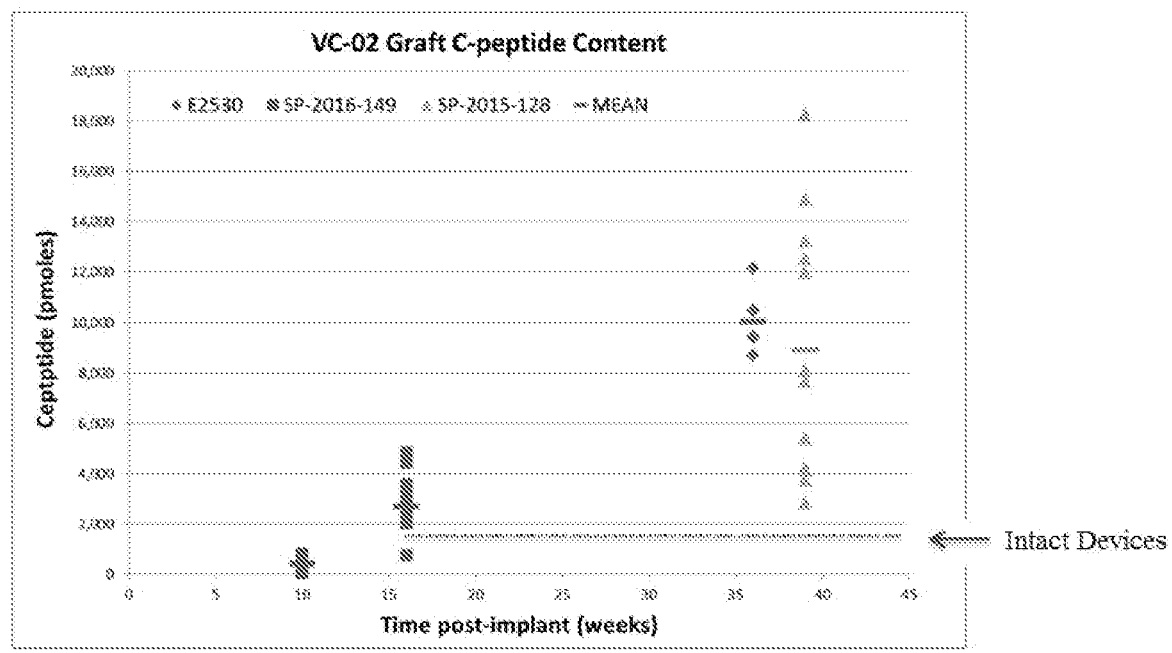
FIG. 7 is a graph showing the total C-peptide protein content in explanted grafts from rats previously implanted with pancreatic progenitors delivered in a perforated devices for 10, 16, 36 and 39 weeks post implant. The perforated device used to generate the 10 and 16 week data is similar to FIG. 1D except the NWF is not laminated to the cell-excluding membrane and has holes spaced 2 mm apart. The NWPF used has a basic weight of 1.00 oz/yd$^2$ and a nominal thickness of 228 µm and fiber diameter of 26 µm. The perforated device used to generate the 36 week data is the same as the 16 week devices except they have no NWF. The perforated device used to generate the 39 week data is the same as the 16 week devices except the NWF used has a basic weight of 0.75 oz/yd$^2$ and holes were spaced at 2 mm.

Example 4: Perforated Devices have an Improved Dosing Profile Compared to Unperforated Devices The rats implanted with perforated delivery devices described in Example 3, table 2 above showed increased human c-peptide content over time compared to intact devices in mice (see e.g. dotted line in FIG. 7 for intact devices). FIG. 7 shows the c-peptide produced by various perforated configurations and demonstrates that in perforated devices with a NWF layer the c-peptide (which is indicative of insulin content) increases over time up to about 30 or 35 or 40 weeks. At about 15 weeks the cells in a perforated device produce about 50% more c-peptide than cells implanted in a non-perforated device. At 16 weeks, the mean c-peptide produced by cells in perforated devices is 2,696 pmoles (FIG. 7, SP-2016-149), which based on the linear relationship of levels of c-peptide to IEQs as described in FIG. 3, is about 6,300 IEQ per device, i.e. the cell dose is about 6300 IEQs. By about 39 weeks, cells in a perforated device have a mean c-peptide value of 9,244 pmoles (FIG. 7, SP-2015-128), which again based on FIG. 3, is about a dose of 23,100 IEQ per device.

While the c-peptide produced in rats implanted with a cell-retained perforated device is higher than in an intact cell-contained device, it takes longer (about 35 weeks) for the c-peptide levels to plateau in the perforated device (FIG. 7, SP-2015-128). Stated another way, perforated and non-perforated (intact) cell devices have similar levels of human c-peptide until about 16 weeks, then, the intact cell devices plateau while the perforated devices continue to increase.

the higher c-peptide concentrations achieved in perforated devices are not reached until after about 16 weeks. See FIG. 7, SP-2016-149 to SP-2015-128. In comparison, c-peptide levels in mice implanted with intact devices plateau at less than 2,000 pmoles at about 16 weeks. FIG. 7 (dotted horizontal line).

Figure 8:
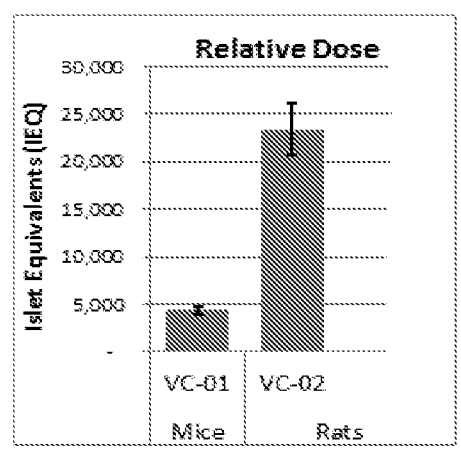
FIG. 8 is a graph showing about a 5 fold increase in the beta cell mass achieved in individual grafts by implanting pancreatic endoderm cells in perforated devices in rats for approximately 9 months compared to intact devices implanted into mice for similar periods of time.
Figure 9:
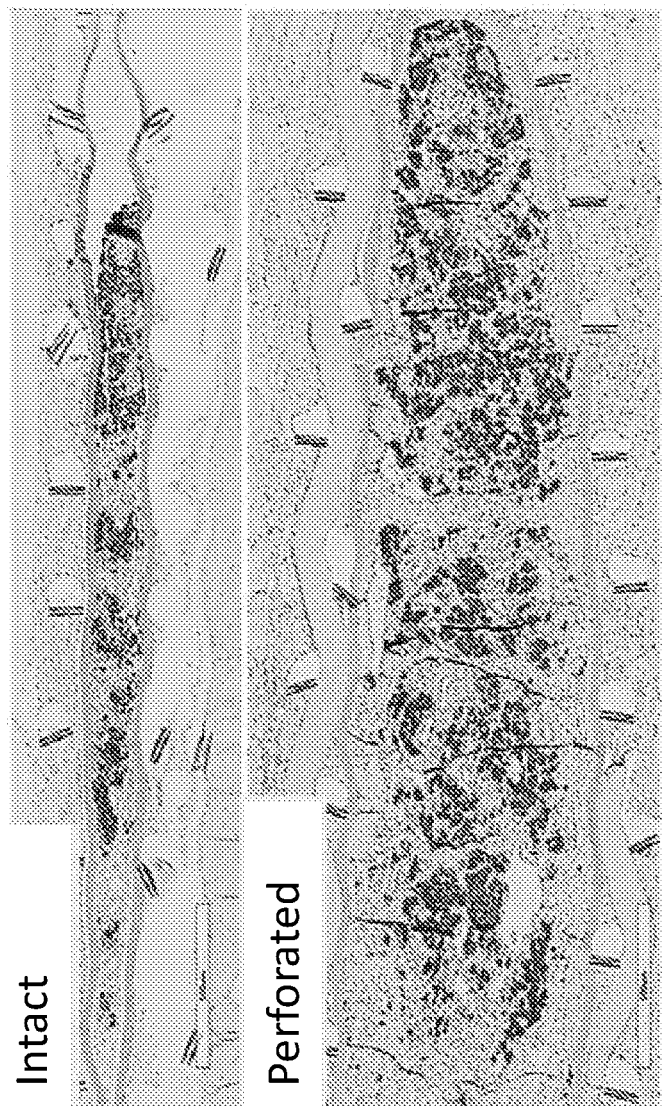
FIG. 9 is a picture of a cross section of an intact and perforated cell delivery device after the c-peptide has plateaued. The perforated device has expanded compared to the intact device and contains many more insulin-producing cells (beta cells).

The cell dose or IEQs from perforated devices implanted for 36 or 39 weeks in rats were compared to intact devices implanted in mice for the same period. There was about a 5 fold increase in the cell dose or IEQ in the perforated devices in rats as compared to the intact devices in mice. See FIG. 8. FIG. 8 shows that intact devices in mice have an IEQ of less than about 5,000 while perforated devices in rats have an IEQ of about 23,100 pmol-a 5-fold difference. This may be because the cells in the perforated devices are able to expand and therefore hold more insulin producing cells and/or cells are producing more insulin per cell. See FIG. 9 which shows a micrograph of a histological cross-section of cells in an intact (top) and perforeated (bottom) delivery device of the same size and same initial cell dosage loaded into each device. It is clear that after maturation, the cells in the perforated devices are more proliferative than the cells in the intact device. That is, there is more cell mass, or preferably more beta cell mass. Human c-peptide data as described above and in FIG. 7, demonstrate that mature cells in the perforated devices produce greater amounts of c-peptide than the cells in the intact devices. And greater c-peptide levels as shown in FIG. 7 correlates to greater islets numbers or IEQs, and greater IEQs is indicative of greater cell dose.

Because cells in perforated devices have a 5-6 fold increase in IEQ values as compared to cells in intact or non-perforated devices, a therapeutic cell dose can be achieved with fewer perforated devices or smaller perforated devices as compared to cells in intact devices. Thus, in one embodiment, cells in perforated devices provide improved dosing capacity per same size capacity device as intact or non-perforated devices.

Example 5: Pancreatic Endoderm can Mature in Nude Rats Treated with Calcineurin Inhibitors As with islet replacement therapy, transplanting therapeutic cells in a perforated device requires chronic immunosuppressant therapy. Maintenance immunosuppression for cadaver islet cell transplants use calcineurin inhibitors like tacrolimus (TAC) and less often cyclosporine (CsA), and the anti-proliferative agent, mycophenolate mofetil (MMF). It has been reported that calcineurin inhibitors are (1) diabetogenic (producing diabetes, Crutchlow et al. (2007), supra) and (2) negatively impact endogenous pancreatic regeneration in mice (Heit (2006), supra and Nir (2007), supra). As such, adverse effects resulting from immunosuppression administration may be expected for maturation of pancreatic endoderm since proliferation is an important component of encapsulated pancreatic endoderm maturation in vivo and for mature beta cells derived from pancreatic endoderm cell grafts.

To test the effects of ISDs, 5 nude rats were fed normal chow and 5 nude rates were feed chow formulated with cyclosporine A at 250 mg/kg for 18 weeks. This has the advantage of avoiding stressful daily dosing through IP injections and/or oral gavage. The resulting drug exposure levels expressed as 12-hour area under the blood concentration curve ($AUC_{0-12\ hr}$), were estimated at approximately 16 µg·hr/mL. This exposure is high compared to cyclosporine A clinical target $AUC_{0-12\ hr}$ of 6-9 µg·hr/mL in renal and liver transplant recipients.

Figure 10A:
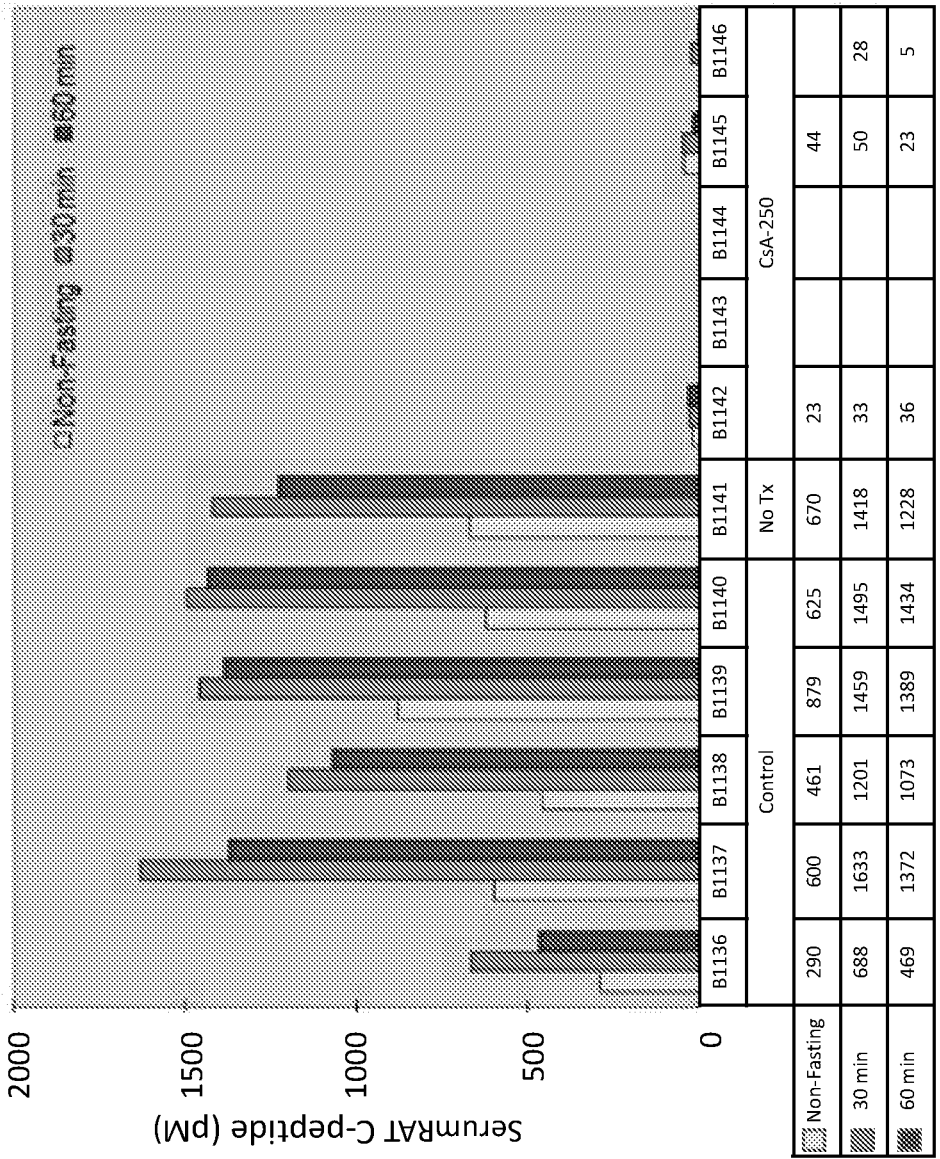
FIGS. 10A and 10B are graphs showing the concentrations of rat or human c-peptide in sera of nude rats fed normal chow (Control) or chow containing 250 mg/kg cyclosporine A (CsA-250) implanted with pancreatic endoderm delivered in a perforated delivery device.

In response to the calcineurin inhibitor, the treated rats became diabetic. Specifically, rats administered cyclosporine A at 250 mg/kg chow became hyperglycemic after approximately 10 weeks that is to say the rats produced no endogenous c-peptide. Serum rat c-peptide levels 30 and 60 minutes post-glucose challenge were well below 500 pM. See FIG. 10A. This effect was temporarily managed through the administration of exogenous insulin (Linbit pellet and Lantus). Otherwise, the cyclosporine A diet was well tolerated by the rats. Indeed, weight and food consumption rates were normal when compared to animals fed a control diet.

Figure 10B:
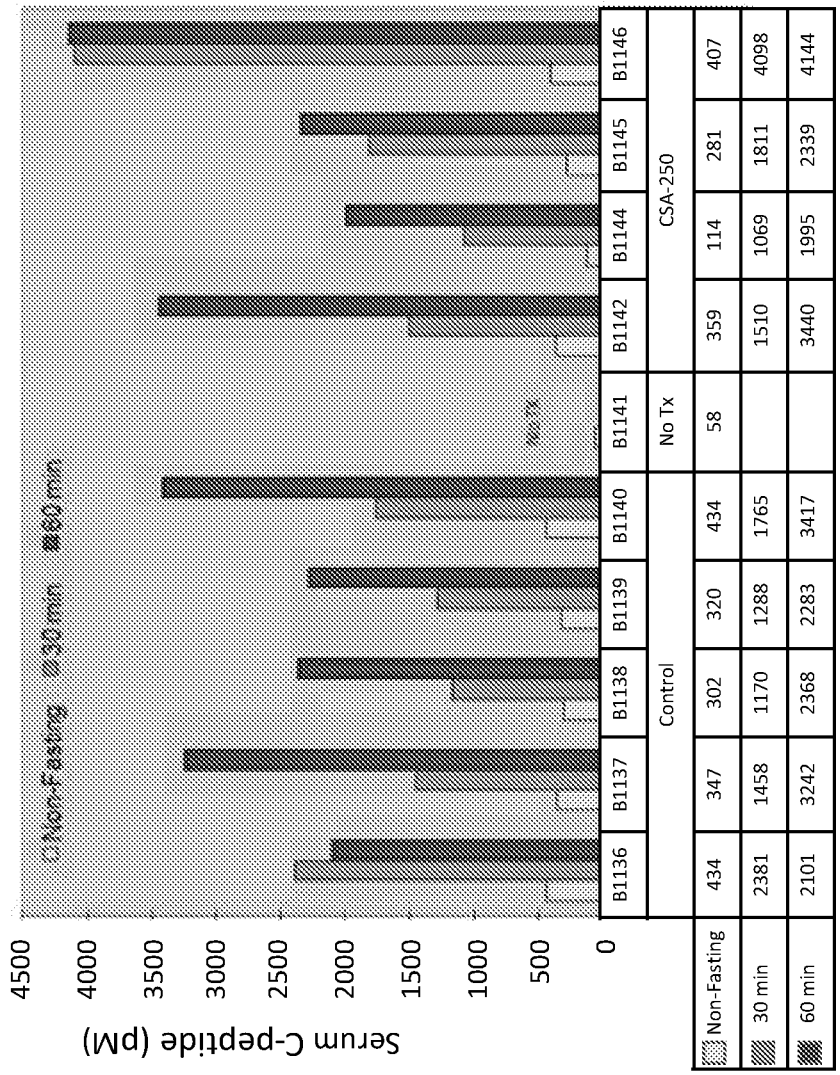

The rats were then implanted with perforated devices containing pancreatic progenitors (or PEC) in small EN20 devices as previously described. The devices did not contain any NWF layers. At 18 weeks post-implant, serum levels of human c-peptide in cyclosporine A treated animals was not substantially different than in untreated control rats (FIG. 10B). All CsA-treated animals produced robust levels of insulin as observed by 1069 to 4098 pM human sera c-peptide at 30 minutes and 1995 to 4144 pM human sera c-peptide at 60 minutes. Importantly, the animals were no longer hyperglycemic or requiring exogenous insulin. For example, at 15 weeks the mean blood glucose was 283 mg/dL (hyperglycemic), at 20 weeks it was 128 mg/dL (normoglycemic). This indicated that the grafts from the perforated devices were now regulating normal blood glucose. This data demonstrates that PEC in perforated devices continued to differentiate and function in rats administered CsA. This remained true for at least 36 weeks after implant (data not shown), indicating a lack of PEC and graft sensitivity to supra-therapeutic levels of calcineurin inhibition through cyclosporine A.

The above demonstrates that even in diabetic (hyperglycemic) rats treated with calcineurin inhibition, pancreatic endoderm transplanted in perforated devices is still able to mature and produced insulin-producing cells and reverse the diabetic condition.

Example 6: Pancreatic Endoderm can Mature in Nude Rats Treated with Calcineurin Inhibitors and Anti-Metabolite Immunosuppressive Agents The ability of pancreatic endoderm encapsulated in perforated devices to mature to insulin-producing cells when exposed to both a calcineurin inhibitor and anti-metabolite immunosuppressive agents was evaluated. Table 12 outlines the study protocol. Nude rats were fed each of normal food chow (Control), chow containing 250 mg/kg cyclosporine A (CsA-250), chow containing 250 mg/kg cyclosporine A and 500 mg/kg Mycophenolate Mofetil (CsA-250+MMF500), or chow containing 150 mg/kg Tacrolimus and 500 mg/kg Mycophenolate Mofetil (TAC-150+MMF500). After two weeks of diet acclimation animals were implanted with PEC delivered in perforated devices as described above in Examples 1-4.

Chow reformulation with desired ISD content was performed at Bio-Sery (Remington, N.J.). Grain-based PicoLab 5053 diet, ½" pellets, is the chow base, identical to the control diet, and was provided to rats ad libitum.

TABLE 11

Various Chow Formulations

| Chow formulation name | CsA-250 |
|---|---|
| Bio-Serve Diet Code | F7043 |
| ISD content | 250 mg CsA per kg chow |
| ISD source information | CycloSPORINE ORAL SOLUTION USP MODIFIED. 100 mg/mL. NDC 0172-7313-20 |
| * Estimated daily dose administration | 17.5 mg CsA/kg body weight |
| Chow formulation name | CsA-250/MMF-500 |
| Bio-Serve Diet Code | F7131 |
| ISD content | 250 mg CsA AND 500 mg MMF per kg chow |
| ISD source information | CycloSPORINE ORAL SOLUTION USP MODIFIED. 100 mg/mL. NDC 0172-7313-20 Mycophenolate Mofetil Tablets USP. 500 mg/Tablet NDC 16729-019-01 |
| * Estimated daily dose administration | 17.5 mg CsA/kg body weight 35 mg MMF/kg body weight |
| Chow formulation name | TAC-150/MMF-500 |
| Bio-Serve Diet Code | F7120 |
| ISD content | 150 mg TAC AND 500 mg MMF per kg chow |
| ISD source information | Mycophenolate Mofetil Tablets USP. 500 mg/Tablet NDC 16729-019-01 PROGRAF (tacrolimus) capsules USP. 5 mg/Tablet NDC 55111-527-01 |
| * Estimated daily dose administration | 10.5 mg TAC/kg body weight 35 mg MMF/kg body weight |

The estimated ISD dose administration is based on typical rat daily food consumption rates of approximately 70 g chow per kg body weight. Actual food consumption rates and ISD dose administrations were measured.

TABLE 12

Pancreatic Endoderm Encapsulated In Perforated Devices In Nude Rats Treated with Immunosuppressive Drugs, CsA, MMF, and TAC

| Species | Diet | Group Number | In-Life Period (Weeks) | Number of Animals | *Number of Implants |
|---|---|---|---|---|---|
| RAT | CONTROL | 1 | 39 | 5 | 10 |
| | CsA-250 | 2 | 39 | 8 | 16 |
| | CsA-250 + MMF-500 | 3 | 39 | 8 | 16 |

TABLE 12-continued

Pancreatic Endoderm Encapsulated In Perforated Devices In Nude Rats Treated with Immunosuppressive Drugs, CsA, MMF, and TAC

| Species | Diet | Group Number | In-Life Period (Weeks) | Number of Animals | *Number of Implants |
|---|---|---|---|---|---|
| | TAC-150 + MMF-500 | 4 | 39 | 8 | 16 |
| MOUSE | CONTROL | 5 | 26 | 12 | 12 |
| | | | TOTAL | 41 | 70 |

*All animals received subcutaneous grafts (one per mouse or two per nude rat) of approximately $7 \times 10^6$ pancreatic endoderm cells delivered in a device perforated manually with needles.
Note
delivery devices do not contain NWF layer(s).

Figure 11:
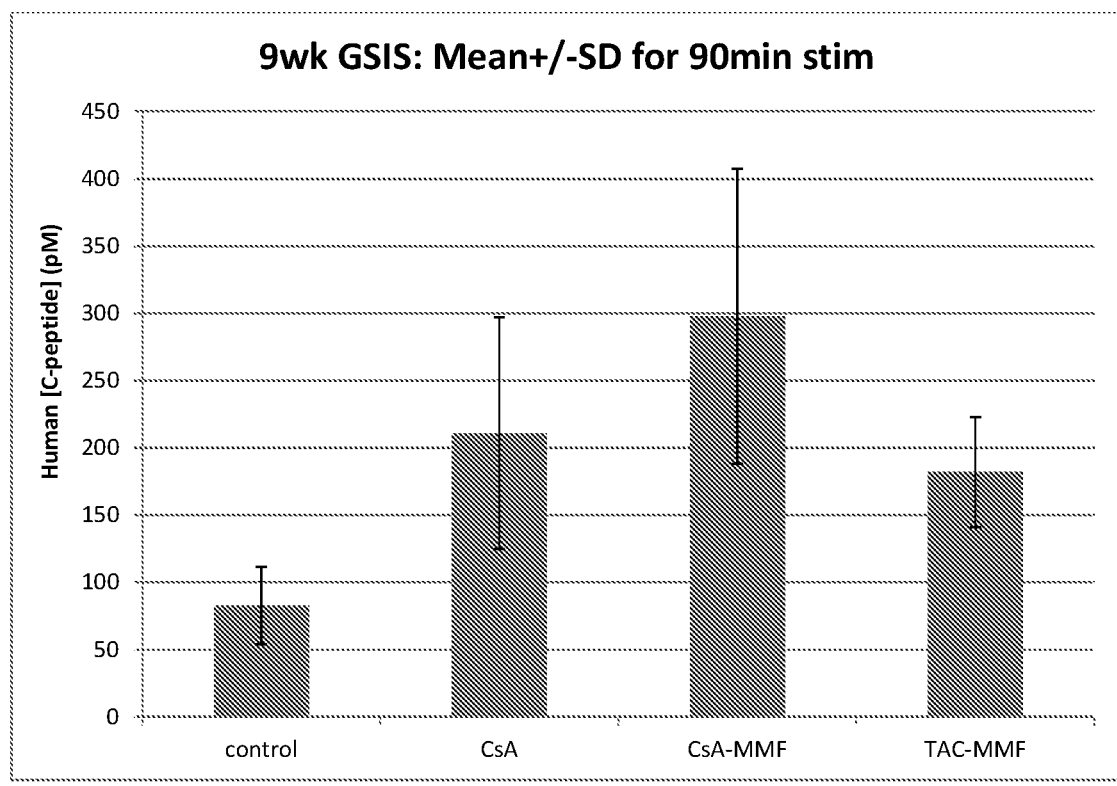
FIG. 11 is a graph showing the concentrations of human c-peptide in sera of rats fed normal chow (Control) or chow containing 250 mg/kg cyclosporine A (CsA-250) or chow containing 250 mg/kg cyclosporine A and 500 mg/kg Mycophenolate Mofetil (CsA-250+MMF500) or chow containing 150 mg/kg Tacrolimus and 500 mg/kg Mycophenolate Mofetil (TAC-150+MMF500) implanted with pancreatic endoderm in a perforated delivery device. The CsA treated rats have slightly elevated blood glucose levels due to the ISD toxicity of endogenous beta cells.

Nine weeks post implant, rats treated with ISDs (either CsA-MMF or TAC-MMF) had higher human c-peptide levels than the control (no ISD). See FIG. 11. This transient higher human c-peptide level is due, in part, because these animals were made diabetic as a consequence of the ISD treatment, making their blood glucose levels higher than control animals due to a lack of endogenous insulin secretion. Presented in another way, rats treated with ISDs are expected to have lower levels of rat c-peptide as compared to controls.

Example 7: Non-Woven Polyester Layers in Perforated Cell Delivery Devices Improve Pancreatic Progenitor Development and Function Examples 1-4 demonstrated that incorporation of NWF provides increased structure and function for the cell encapsulating and delivery devices, independent of whether the NWF was laminated or not to the cell-excluding membrane layer and independent of the hole density (number of holes) per device. Example 5 demonstrated that pancreatic progenitors derived from human pluripotent stems could in fact survive, develop and mature into functioning pancreatic endocrine cells when the host is treated with an immune-suppression regimen of calcineurin inhibitors (e.g. CsA), which had previously not been described and was unknown until Applicant's disclosure. Example 6 further demonstrated that not only could the pancreatic progenitors survive an immune-suppression regimen of calcineurin inhibitors but also anti-metabolite immunosuppressive agents as well.

In this study, the teachings of Examples 1-6 were combined to determine the function of the pancreatic progenitors in perforated delivery devices and non-perforated delivery devices incorporating at least one NWF layer (per wall or side of the device) and treated with the combination of calcineurin inhibitor and anti-metabolite immune-suppression regimen.

Figure 12:
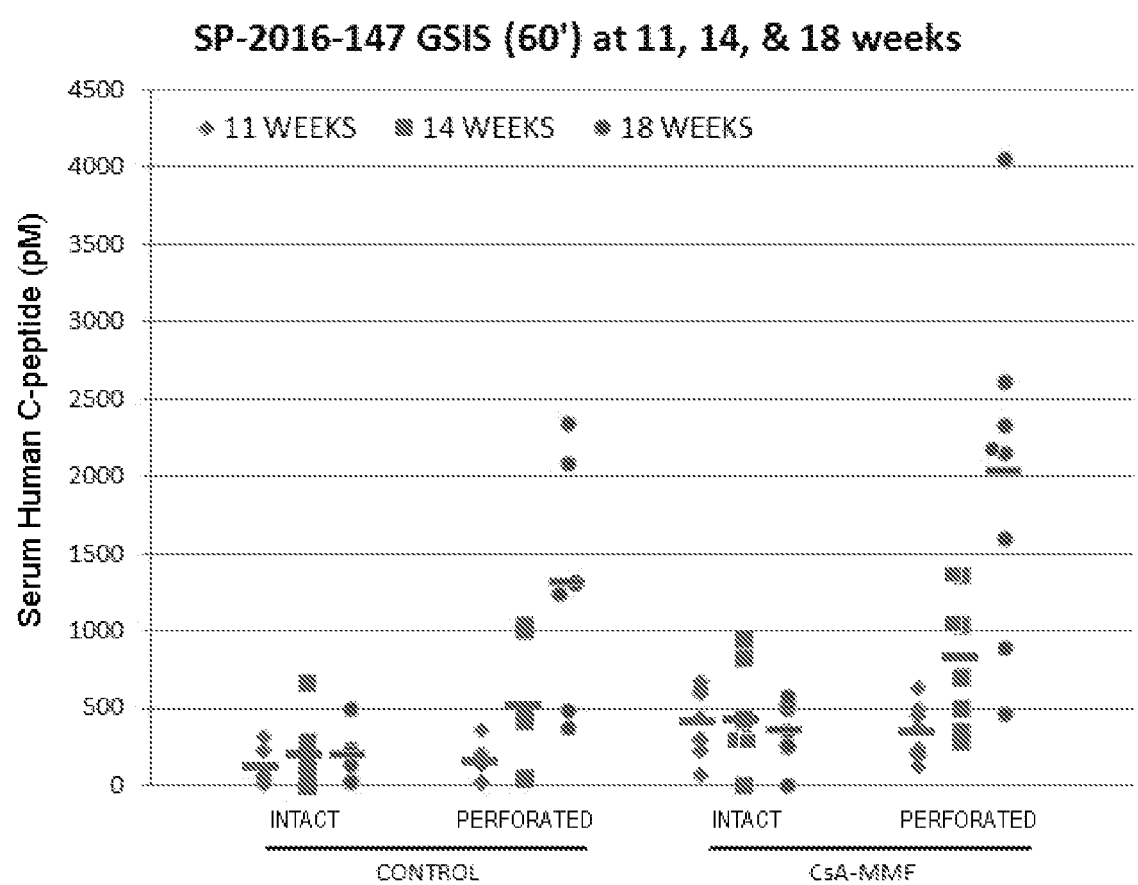
FIG. 12 is a graph showing the concentrations of human c-peptide in sera of nude rats fed normal chow (Control) or chow containing CsA-MMF implanted with pancreatic endoderm delivered in either a perforated or non-perforated (intact) delivery device at 11 weeks (♦), 14 weeks (■) and 18 weeks (●).

In general, control rats implanted with perforated NWF delivery devices had greater human c-peptide levels than rats implanted with cells in a non-perforated NWF encapsulation device. See FIG. 12 (Control, comparing intact and perforated, no treatment with CsA-MMF). This is due to the direct vascularization of host blood vessels with the implanted cells through the perforations (holes) in the perforated devices, which improves cell survival. Further, in rats treated with an ISD, animals implanted with perforated NWF delivery devices also had greater human C-peptide levels than animals implanted with non-perforated NWF devices. See FIG. 12 (comparing intact and perforated, treated with CsA-MMF). Interestingly, the human c-peptide levels of those animals receiving CsA-MMF and perforated NWF delivery devices was about twice (1.6-fold) as high as those animals receiving the same type of perforated NWF delivery device but without CsA-MMF immune-suppression. See FIG. 12. This increase in human c-peptide may be the result of a synergistic effect of the combination of a NWF delivery device and CsA-MMF immune-suppression regimen. This improved human c-peptide levels maybe the result of improved host vascularization mitigated by the NWF alone and/or in combination with the ISD.

What is claimed is:

1. A cell encapsulation device, comprising: at least one chamber, wherein the at least one chamber comprises a cell-excluding membrane wherein the cell-excluding membrane comprises an inner surface in contact with definitive endoderm lineage cells, and an external surface in contact with a non-woven fabric layer, wherein the definitive endoderm lineage cells are contained within the cell-excluding membrane, and wherein at least a portion of an outer surface of the cell encapsulation device is configured to be placed in direct contact with host tissue upon implantation of the cell encapsulation device into a mammalian host.

2. The cell encapsulation device of claim 1, wherein the non-woven fabric layer is not laminated to the cell-excluding membrane in the cell delivery device.

3. The cell encapsulation device of claim 1, wherein the non-woven fabric layer and cell-excluding membrane are laminated together.

4. The cell encapsulation device of claim 1, wherein the non-woven fabric layer and cell-excluding membrane comprise perforations.

5. The cell encapsulation device of claim 4, wherein the non-woven fabric layer and cell-excluding membrane comprise a) less than 40 perforations, b) less than 20 perforations, c) 5 perforations to 200 perforations, or d) 20 perforations to 100 perforations.

6. The cell encapsulation device of claim 4, wherein each perforation in the non-woven fabric layer and the cell-excluding membrane has a diameter of a) no greater than 150 microns, b) no greater than 100 microns, c) no greater than 75 microns, d) no greater than 50 microns, e) 50 microns to 300 microns, f) 50 microns to 200 microns, g) 75 microns to 200 microns, h) 200 microns to 400 microns, i) 70 microns to 80 microns, j) less than 100 microns, or k) 40 microns to 150 microns.

7. The cell encapsulation device of claim 4, wherein each perforation in the non-woven fabric layer and the cell-excluding membrane is separated by a) about 0.5 mm, b) about 1.0 mm, c) about 1.5 mm, d) about 2 mm, e) about 4 mm, f) about 8 mm, g) about 0.5 mm to about 4 mm, h) about 0.5 mm to about 2 mm, or i) about 1.0 mm to about 2 mm, as measured from the center of one perforation to the center of another perforation.

8. The cell encapsulation device of claim 1, wherein the cell-excluding membrane comprises perforations.

9. The cell encapsulation device of claim 8, wherein the cell-excluding membrane comprises a) less than 40 perforations, b) less than 20 perforations, c) 5 perforations to 200 perforations, or d) 20 perforations to 100 perforations.

10. The cell encapsulation device of claim 8, wherein each perforation in the cell-excluding membrane has a diameter of a) no greater than 150 microns, b) no greater than 100 microns, c) no greater than 75 microns, d) no greater than 50 microns, e) 50 microns to 300 microns, f) 50 microns to 200 microns, g) 75 microns to 200 microns, h) 200 microns to 400 microns, i) 70 microns to 80 microns, j) less than 100 microns, or k) 40 microns to 150 microns.

11. The cell encapsulation device of claim 8, wherein each perforation in the cell-excluding membrane is separated by a) about 0.5 mm, b) about 1.0 mm, c) about 1.5 mm, d) about 2 mm, e) about 4 mm, f) about 8 mm, g) about 0.5 mm to about 4 mm, h) about 0.5 mm to about 2 mm, or i) about 1.0 mm to about 2 mm, as measured from the center of one perforation to the center of another perforation.

12. The cell encapsulation device of claim 1, wherein the definitive endoderm lineage cells are pancreatic progenitor cells, endocrine precursor cells, pancreatic endocrine cells, or pancreatic beta cells.

13. The cell encapsulation device of claim 1, wherein the non-woven fabric layer comprises a filament cross section that is trilobal.

14. The cell encapsulation device of claim 1, wherein the definitive endoderm lineage cells express at least one marker selected from the group consisting of neurogenin 3 (NEUROG3), PDX1, PTF1A, SOX9, NKX6.1, HNF1b, GATA4, HNF6, FOXA1, FOXA2, GATA6, MYT1, ISLET1, NEUROD, SNAIL2, MNX1, IA1, RFX6, PAX4, PAX6, NKX2.2, and MAFB.

15. A cell encapsulation device, comprising; at least one chamber, wherein the at least one chamber comprises a cell-excluding membrane, wherein the cell-excluding membrane comprises an inner surface in contact with definitive endoderm lineage cells and an external surface in contact with a non-woven fabric layer, and a mesh layer external to the non-woven fabric layer, wherein the non-woven fabric layer protects the cell-excluding membrane from direct contact with the mesh layer, wherein the definitive endoderm lineage cells are contained within the cell-excluding membrane, and wherein at least a portion of an outer surface of the cell encapsulation device is configured to be placed in direct contact with host tissue upon implantation of the cell encapsulation device into a mammalian host.

16. The cell encapsulation device of claim 15, wherein the definitive endoderm lineage cells are pancreatic progenitor cells, endocrine precursor cells, immature endocrine cells, endocrine cells or pancreatic islet cells.

17. The cell encapsulation device of claim 15, wherein the non-woven fabric layer comprises a filament cross section that is trilobal.

18. The cell encapsulation device of claim 15, wherein the definitive endoderm lineage cells express at least one marker selected from the group consisting of neurogenin 3 (NEUROG3), PDX1, PTF1A, SOX9, NKX6.1, HNF1b, GATA4, HNF6, FOXA1, FOXA2, GATA6, MYT1, ISLET1, NEUROD, SNAIL2, MNX1, IA1, RFX6, PAX4, PAX6, NKX2.2, and MAFB.

* * * * *